(12) United States Patent
Burgo

(10) Patent No.: US 8,105,569 B2
(45) Date of Patent: Jan. 31, 2012

(54) NON-PETROCHEMICALLY DERIVED CATIONIC EMULSIFIERS THAT ARE NEUTRALIZED AMINO ACID ESTERS AND RELATED COMPOSITIONS AND METHODS

(75) Inventor: Rocco Burgo, Mullica Hill, NJ (US)

(73) Assignee: Inolex Investment Corporation, Wilmington, DE (US)

( * ) Notice: Subject to any disclaimer, the term of this patent is extended or adjusted under 35 U.S.C. 154(b) by 0 days.

(21) Appl. No.: 12/825,555

(22) Filed: Jun. 29, 2010

(65) Prior Publication Data

US 2010/0330004 A1    Dec. 30, 2010

Related U.S. Application Data

(60) Provisional application No. 61/221,154, filed on Jun. 29, 2009.

(51) Int. Cl.
    *A61K 8/00*     (2006.01)
    *A61K 8/18*     (2006.01)
    *A61Q 5/02*     (2006.01)
    *A61Q 5/12*     (2006.01)

(52) U.S. Cl. ....... 424/70.122; 424/59; 424/63; 424/401; 514/506

(58) Field of Classification Search .......... None
See application file for complete search history.

(56) References Cited

U.S. PATENT DOCUMENTS

| | | | | |
|---|---|---|---|---|
| 3,907,580 | A * | 9/1975 | Van Ham | 106/124.3 |
| 6,149,924 | A * | 11/2000 | Paul | 424/401 |
| 6,287,547 | B1 * | 9/2001 | Oota et al. | 424/70.28 |
| 6,379,719 | B1 | 4/2002 | Gilles | |
| 6,528,068 | B1 * | 3/2003 | Yumioka et al. | 424/401 |
| 7,671,082 | B2 * | 3/2010 | Moher et al. | 514/443 |
| 2006/0239952 | A1 * | 10/2006 | Hattori | 424/70.14 |
| 2008/0108709 | A1 * | 5/2008 | Meyer et al. | 514/777 |
| 2008/0280865 | A1 * | 11/2008 | Tobita | 514/182 |

FOREIGN PATENT DOCUMENTS

EP      1314717 A1 *    5/2003

* cited by examiner

*Primary Examiner* — Robert A Wax
*Assistant Examiner* — Olga V Tcherkasskaya
(74) *Attorney, Agent, or Firm* — Flaster/Greenberg PC

(57) ABSTRACT

The invention includes a method of increasing the substantivity of a personal care composition to hair, skin or nails by preparing a composition of an aqueous phase, a non-aqueous phase and a neutralized amino acid ester that is a reaction product of a neutral amino acid having a non-polar side chain with a long chain fatty alcohol and is represented by formula (I):

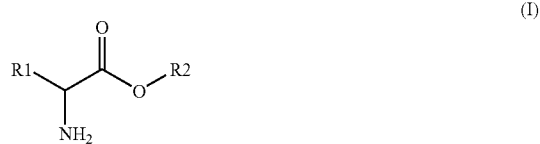

(I)

wherein $R^1$ is an alkyl group; $R^2$ is a linear or branched carbon chain; and the amine group of the amino acid is neutralized with an acid. The composition is substantially free of petrochemicals and/or derivatives of petrochemical materials. The aqueous phase and the non-aqueous phase are emulsified by the neutralized amino acid ester. Other methods and an emulsifiers that is the neutralized amino acid ester are included. Because the neutralized amino acid ester and the compositions do not contain petrochemical-derived ingredient, the products are natural.

13 Claims, 47 Drawing Sheets

FIG. 14

Sample 1-4 / 0% arginine

| Ingredients | 1 %wt/wt | 2 %wt/wt | 3 %wt/wt | 4 %wt/wt |
|---|---|---|---|---|
| Deionized Water | 88.2 | 86.2 | 84.2 | 82.2 |
| Base II | 8 | 10 | 12 | 14 |
| Natural Oil | 3 | 3 | 3 | 3 |
| Spectrastat | 0.8 | 0.8 | 0.8 | 0.8 |
|  | 100 | 100 | 100 | 100 |

Sample 5-8 / 100% arginine

| Ingredients | 5 %wt/wt | 6 %wt/wt | 7 %wt/wt | 8 %wt/wt |
|---|---|---|---|---|
| Deionized Water | 88.03 | 85.99 | 83.95 | 81.9 |
| Arginine | 0.17 | 0.21 | 0.25 | 0.3 |
| Base II | 8 | 10 | 12 | 14 |
| Natural Oil | 3 | 3 | 3 | 3 |
| Spectrastat | 0.8 | 0.8 | 0.8 | 0.8 |
|  | 100 | 100 | 100 | 100 |

Sample 9-16 / 100% arginine

| Ingredients | 9 %wt/wt | 10 %wt/wt | 11 %wt/wt | 12 %wt/wt | 13 %wt/wt | 14 %wt/wt | 15 %wt/wt | 16 %wt/wt |
|---|---|---|---|---|---|---|---|---|
| Deionized Water | 88.02 | 88.01 | 88.01 | 87.98 | 85.93 | 87.96 | 85.95 | 85.93 |
| Arginine | 0.178 | 0.19 | 0.202 | 0.216 | 0.22 | 0.235 | 0.25 | 0.267 |
| Base I | 2.79 | 2.98 | 3.17 | 3.39 | 3.49 | 3.73 | 3.97 | 4.24 |
| Cetyl Alcohol | 2.605 | 2.51 | 2.41 | 2.305 | 3.255 | 2.135 | 3.015 | 2.88 |
| Stearyl Alcohol | 2.605 | 2.51 | 2.41 | 2.305 | 3.255 | 2.135 | 3.015 | 2.88 |
| Natural Oil | 3 | 3 | 3 | 3 | 3 | 3 | 3 | 3 |
| Spectrastat | 0.8 | 0.8 | 0.8 | 0.8 | 0.8 | 0.8 | 0.8 | 0.8 |
|  | 100 | 100 | 100 | 100 | 100 | 100 | 100 | 100 |

Sample 17-24 / 100% arginine

| Ingredients | 17 %wt/wt | 18 %wt/wt | 19 %wt/wt | 20 %wt/wt | 21 %wt/wt | 22 %wt/wt | 23 %wt/wt | 24 %wt/wt |
|---|---|---|---|---|---|---|---|---|
| Deionized Water | 83.938 | 83.92 | 83.902 | 83.883 | 81.886 | 81.864 | 81.843 | 81.818 |
| Arginine | 0.262 | 0.28 | 0.298 | 0.317 | 0.314 | 0.336 | 0.357 | 0.382 |
| Base I | 4.19 | 4.48 | 4.76 | 5.09 | 4.89 | 5.22 | 5.56 | 5.93 |
| Cetyl Alcohol | 3.905 | 3.76 | 3.62 | 3.455 | 4.55 | 4.39 | 4.22 | 4.035 |
| Stearyl Alcohol | 3.905 | 3.76 | 3.62 | 3.455 | 4.55 | 4.39 | 4.22 | 4.035 |
| Natural Oil | 3 | 3 | 3 | 3 | 3 | 3 | 3 | 3 |
| Spectrastat | 0.8 | 0.8 | 0.8 | 0.8 | 0.8 | 0.8 | 0.8 | 0.8 |
|  | 100 | 100 | 100 | 100 | 100 | 100 | 100 | 100 |

Sample 25-28 with 50% arginine

| Ingredients | 25 %wt/wt | 26 %wt/wt | 27 %wt/wt | 28 %wt/wt |
|---|---|---|---|---|
| Deionized Water | 88.11 | 86.09 | 84.08 | 82.05 |
| Arginine | 0.085 | 0.105 | 0.124 | 0.147 |
| Base II | 8 | 10 | 12 | 14 |
| Natural Oil | 3.00 | 3.00 | 3.00 | 3.00 |
| Spectrastat | 0.8 | 0.8 | 0.8 | 0.8 |
|  | 100 | 100 | 100 | 100 |

Sample 29-36 / half arginine

| Ingredients | 29 %wt/wt | 30 %wt/wt | 31 %wt/wt | 32 %wt/wt | 33 %wt/wt | 34 %wt/wt | 35 %wt/wt | 36 %wt/wt |
|---|---|---|---|---|---|---|---|---|
| Deionized Water | 88.09 | 88.09 | 88.09 | 88.07 | 86.07 | 88.06 | 86.05 | 86.04 |
| Arginine | 0.1068 | 0.114 | 0.1212 | 0.1296 | 0.132 | 0.141 | 0.15 | 0.1602 |
| Base I | 2.79 | 2.98 | 3.17 | 3.39 | 3.49 | 3.73 | 3.97 | 4.24 |
| Cetyl Alcohol | 2.605 | 2.51 | 2.41 | 2.305 | 3.255 | 2.135 | 3.015 | 2.88 |
| Stearyl Alcohol | 2.605 | 2.51 | 2.41 | 2.305 | 3.255 | 2.135 | 3.015 | 2.88 |
| Natural Oil | 3 | 3 | 3 | 3 | 3 | 3 | 3 | 3 |
| Spectrastat | 0.8 | 0.8 | 0.8 | 0.8 | 0.8 | 0.8 | 0.8 | 0.8 |
|  | 100 | 100 | 100 | 100 | 100 | 100 | 100 | 100 |

Sample 37-44 / half arginine

| Ingredients | 37 %wt/wt | 38 %wt/wt | 39 %wt/wt | 40 %wt/wt | 41 %wt/wt | 42 %wt/wt | 43 %wt/wt | 44 %wt/wt |
|---|---|---|---|---|---|---|---|---|
| Deionized Water | 84.07 | 84.06 | 84.051 | 84.041 | 81.42 | 82.032 | 82.022 | 82.01 |
| Arginine | 0.131 | 0.14 | 0.149 | 0.159 | 0.785 | 0.168 | 0.178 | 0.191 |
| Base I | 4.19 | 4.48 | 4.76 | 5.09 | 4.89 | 5.22 | 5.56 | 5.93 |
| Cetyl Alcohol | 3.905 | 3.76 | 3.62 | 3.455 | 4.55 | 4.39 | 4.22 | 4.035 |
| Stearyl Alcohol | 3.905 | 3.76 | 3.62 | 3.455 | 4.55 | 4.39 | 4.22 | 4.035 |
| Natural Oil | 3 | 3 | 3 | 3 | 3 | 3 | 3 | 3 |
| Spectrastat | 0.8 | 0.8 | 0.8 | 0.8 | 0.8 | 0.8 | 0.8 | 0.8 |
|  | 100 | 100 | 100 | 100 | 100 | 100 | 100 | 100 |

Sample 1-4 / 0% arginine

|      | 1     | 2     | 3     | 4     |
|------|-------|-------|-------|-------|
| pH   | 4.25  | 4.35  | 4.4   | 4.48  |
| Visc | 18500 | 20000 | 22800 | 66500 |

Sample 5-24 / 100% arginine

|      | 5     | 6     | 7     | 8     |
|------|-------|-------|-------|-------|
| pH   | 5.38  | 5.66  | 5.73  | 5.78  |
| Visc | 41000 | 54000 | 69000 | 75500 |
|      | 9     | 13    | 17    | 21    |
| pH   | 4.92  | 5.15  | 5.16  | 5.24  |
| Visc | 4000  | 35500 | 57000 | 51000 |
|      | 10    | 14    | 18    | 22    |
| pH   | 4.97  | 4.94  | 5.23  | 5.33  |
| Visc | 6000  | 9000  | 61000 | 77000 |
|      | 11    | 15    | 19    | 23    |
| pH   | 5.02  | 5.39  | 5.22  | 5.55  |
| Visc | 7000  | 56000 | 47000 | 69000 |
|      | 12    | 16    | 20    | 24    |
| pH   | 4.98  | 5.33  | 5.16  | 5.54  |
| Visc | 11500 | 43500 | 54000 | 80000 |

Sample 25-44 / half arginine

|      | 25    | 26    | 27    | 28        |
|------|-------|-------|-------|-----------|
| pH   | 5.09  | 5.26  | 5.27  | 5.49      |
| Visc | 35000 | 59000 | 73000 | 83000     |
|      | 29    | 33    | 37    | 41        |
| pH   | 5.05  | 5.17  | 5.11  | 5.3       |
| Visc | 23000 | 46000 | 91000 | 92000     |
|      | 30    | 34    | 38    | 42        |
| pH   | 5.16  | 4.99  | 5.14  | 5.17      |
| Visc | 16000 | 24000 | 65000 | Too thick |
|      | 31    | 35    | 39    | 43        |
| pH   | 4.99  | 5.05  | 4.87  | 5.08      |
| Visc | 25000 | 42000 | 18000 | Too thick |
|      | 32    | 36    | 40    | 44        |
| pH   | 4.98  | 5.07  | 4.84  | 5.07      |
| Visc | 27000 | 47500 | 72000 | 81000     |

FIG. 15

NON-PETROCHEMICALLY DERIVED CATIONIC EMULSIFIERS THAT ARE NEUTRALIZED AMINO ACID ESTERS AND RELATED COMPOSITIONS AND METHODS

CROSS REFERENCE TO RELATED APPLICATION

This application claims the benefit under 35 U.S.C. §119(e) of U.S. provisional patent application No. 61/221,154, filed Jun. 29, 2009, the entire disclosure of which is incorporated herein by reference.

BACKGROUND OF THE INVENTION

Sales of "natural" products within the personal care industry continue to show significant growth. Popular culture has driven this growth by popularizing the idea that there may be potential adverse effects to the body (toxicity) and to the environment (pollution, hastening of climate change, and environmental toxicity) associated with the use of ingredients derived from fossil fuels. The personal care industry has rapidly advanced its attempts to identify ingredients described as "renewable" and "sustainable," that is, ingredients of non-fossil fuel origin for use in the formulation of virtually all cosmetic product types and forms.

In many instances, the industry has successfully identified replacements for many ingredients that are historically of fossil fuel origin. Examples of this are the replacement of mineral oils, silicones, and petrochemically-derived synthetic esters with vegetable oils and natural esters, synthetic fragrances with essential oils, and petrochemical preservatives with certain extracts.

Although used in marketing materials, the term "natural" has not yet been completely defined. However, efforts are underway by industry trade organizations to give the term a more concise and consistent meaning Historically, it has been generally recognized that materials derived from renewable and/or sustainable, or otherwise non-fossil fuel sources are considered to be "natural" by the marketplace. More recently the definition of "natural" has been further refined. For example, there is a trend within the trade to prohibit animal-derived materials and plant-derived materials that are obtained from the use of genetically-modified organisms (GMO) from use in natural products.

Also, certain chemical processes used in the manufacture of ingredients, especially those processes that employ petrochemical solvents, generate unrecoverable waste, and/or consume excessive resources, are frowned upon or may otherwise be prohibited. The use of "Green Chemistry" principles in the production of cosmetic and personal care ingredients is rapidly becoming a positive benefit that can be exploited in the marketing of products produced using those principles. Thus, the evolving definition of "natural" currently includes products that are not petrochemically derived. However, the other concepts discussed above (non-animal, non-GMO, Green Chemistry) may be taken into consideration when creating "natural" products, and to satisfy market demands.

One particular challenge facing formulators of natural products relates to the identification of suitable emulsifiers. An emulsifier is a type of surfactant typically used to keep emulsions (metastable mixtures of immiscible fluids) well dispersed. Emulsifiers typically have a hydrophobic (water-fearing) and a hydrophilic (water-loving) moiety. In an emulsion involving an oil and water, emulsifiers will surround the oil with their hydrophobic moiety oriented toward the oil, thus forming a protective layer so that the oil molecules cannot coalesce. This action helps keep the dispersed phase in small droplets (micelles) and preserves the emulsion. Emulsifiers may be anionic, nonionic, or cationic. A good emulsifier for use in a personal care product is one that will maintain consistent emulsion characteristics such as particle size, appearance, texture, and viscosity, substantially constant for as long a period as possible since by their very nature, all emulsions due to their metastable nature will eventually separate into their constituent oil soluble and water soluble components. Stability of the emulsion is highly desirable in most products, since among other advantages, this stability contributes to an extended shelf life of the product and the maintenance of its initial aesthetic properties over time.

Although the vast majority of emulsifiers currently used personal care products are wholly or partially petrochemically derived such as polyethylene glycol (PEG) derivatives and amine quaternaries, a limited number of known emulsifiers may meet the current definition of natural. However, presently available natural emulsifiers fall only within the classes of nonionic and anionic emulsifiers.

The natural nonionic emulsifiers are typically partial esters of long chain fatty acids with a polyol. Examples are long chain partial esters of sugars, of alkylglucosides, and of polyglycerols. Although these nonionic emulsifiers can be effective in building stable emulsions, they do little or nothing to provide any conditioning and/or aesthetic benefits to the hair or skin because they are not substantive to these substrates, which are negatively charged.

The natural anionic emulsifiers are typically the long chain fatty acid soaps of fatty acids and sulfuric acid esters (sulfates) of fatty alcohols. These tend to be drying to the skin and provide no aesthetic or conditioning benefits because, like the hair and skin, they are negatively charged and therefore tend to be repelled by these substrates.

Currently there are no known natural cationic emulsifiers. Many personal care applications require or are greatly improved by the use of cationic emulsifiers. Owing to the fact that typical cationic emulsifiers are built from a long chain (hydrophobic) alkyl group attached to a hydrophilic moiety, they act as emulsifiers much the same way as the nonionic and anionic emulsifiers previously described. However, in a cationic emulsifier, the hydrophilic portion of the molecule is positively charged. This cationic moiety will electrostatically bind to (be substantive to) negatively charged substrates such as the hair and skin. The hydrophobic moiety, which is non-ionic, has no affinity for the substrate, and will orient away from the substrate creating a protective layer of fatty material that can provide enhanced sensory properties. The property of substantivity differentiates the cationic emulsifiers from anionic and/or nonionic emulsifiers. It is substantivity that facilitates the conditioning benefits of the end product. Therefore, in addition to being excellent emulsifiers, cationic emulsifiers also deliver the benefits of improving the aesthetics of formulations that include them, and allowing the formulation of personal care products that can condition, moisturize, and repair the skin, hair, or nails. Cationic emulsifiers, unlike anionic and nonionic materials are therefore multifunctional.

Cationic emulsifiers, when used in hair care applications such as cream conditioners, provide excellent conditioning benefits such as improvement in application aesthetics, creaminess and richness of the conditioner, and improvements in such application properties as softening, anti-static behavior, fly-away, wet combing, and dry combing. When cationic emulsifiers, are used in skin care preparations, they are known to provide what is known in the industry as a "dry, light, powdery" skin feel that is a distinct advantage in many skin care products. Exemplary traditional cationic emulsifiers include quaternized cationic emulsifiers such as cetrimonium chloride, behentrimonium chloride and distearyldimonium chloride, and amidoamines such as stearamidopropyl dimethylamine and behenamidopropyl dimethylamine.

All of the traditional cationic emulsifiers are petrochemically derived; therefore, all of these cationic emulsifiers are not considered to be natural and therefore cannot be used in the formulation of natural products. Accordingly, there is a need in the art for natural cationic emulsifiers that have performance and use characteristics and substantivity similar to the traditional cationic emulsifiers.

BRIEF SUMMARY OF THE INVENTION

The invention includes personal care compositions containing a cationic neutralized amino acid ester emulsifier but that is substantially free of petrochemicals and/or derivatives of petrochemical materials and which exhibits performance characteristics (such as substantivity to skin and hair, shelf stability and conditioning/lubrication capabilities) comparable to compositions containing petrochemicals and/or derivatives of petrochemicals, and/or superior to those exhibited by other non-petrochemical containing compositions.

Specifically, the invention may include a method of increasing the substantivity of a personal care composition to hair, skin or nails. The method includes preparing a composition that comprises an aqueous phase, a non-aqueous phase and a neutralized amino acid ester that is a reaction product of a neutral amino acid having a non-polar side chain with a long chain fatty alcohol and is represented by formula (I):

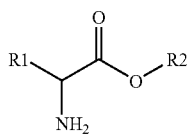

wherein $R^1$ is a linear or branched alkyl group; $R^2$ is a linear or branched carbon chain; and the amine group of the amino acid is neutralized with an acid. The composition is substantially free of petrochemicals and/or derivatives of petrochemical materials. The aqueous phase and the non-aqueous phase are emulsified by the neutralized amino acid ester. The method also includes applying the personal care composition to a surface of hair, skin or nails, wherein the composition exhibits increased substantivity on the surface relative to the substantivity of a composition that does not contain the neutralized amino acid ester and which is substantially free of petrochemicals and/or derivatives of petrochemical materials.

Also included is a method of emulsifying a personal care composition having an aqueous phase and an non-aqueous phase that includes preparing a composition that comprises an aqueous phase, a non-aqueous phase and a neutralized amino acid ester that is a reaction product of a neutral amino acid having a non-polar side chain with a long chain fatty alcohol and is represented by formula (I):

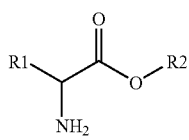

wherein $R^1$ is a linear or branched alkyl group; $R^2$ is a linear or branched carbon chain; and the amine group of the amino acid is neutralized with an acid. The composition is substantially free of petrochemicals and/or derivatives of petrochemical materials.

The invention provides additionally a method of conditioning, lubricating, or repairing the skin, hair or nails comprising applying a neutralized amino acid ester to a surface of skin, hair or nails, wherein the neutralized amino acid ester is a product of a reaction of a neutral amino acid having a non-polar side chain with a long chain fatty alcohol represented by the structure of formula (I):

wherein $R^1$ is a linear or branched alkyl group; $R^2$ is a linear or branched carbon chain; and the amine group of the amino acid is neutralized with an acid.

A cationic emulsifier is provided. The emulsifier includes a neutralized amino acid ester derived from the reaction of a neutral amino acid having a non-polar side chain with a long chain fatty alcohol (such as the ester represented by formula I) wherein the emulsifier is substantially free of petrochemicals and/or derivatives of petrochemical materials.

The invention includes a neutralized amino acid ester emulsifier that is obtained from the reaction of a neutral amino acid having a non-polar side chain with a long chain fatty alcohol. The ester of the invention may have a structure represented by formula (I):

wherein $R^1$ is a linear or branched alkyl group; $R^2$ is a linear or branched carbon chain; and the amine group of the amino acid is neutralized with an acid. Also included is a personal care composition comprising the ester described above. Methods provided by the invention include methods of conditioning the hair or skin, comprising topical application of the personal care composition containing the ester and methods of forming an emulsion comprising the incorporation of the neutralized amino acid ester of the invention, and methods of stabilizing and improving the texture of an emulsion comprising incorporation of a neutralized amino acid ester of the invention with other neutralized amino acid ester(s) of the invention.

BRIEF DESCRIPTION OF THE DRAWINGS

The foregoing summary, as well as the following detailed description of preferred embodiments of the invention, will be better understood when read in conjunction with the appended drawings. It should be understood that the invention is not limited to the precise arrangements and instrumentalities shown. In the drawings:

FIG. 14 is a chart showing several formulations of the invention;

FIG. 15 is a chart showing the initial pH values and viscosities of the formulations of FIG. 14.

DETAILED DESCRIPTION OF THE INVENTION

Figure 1:
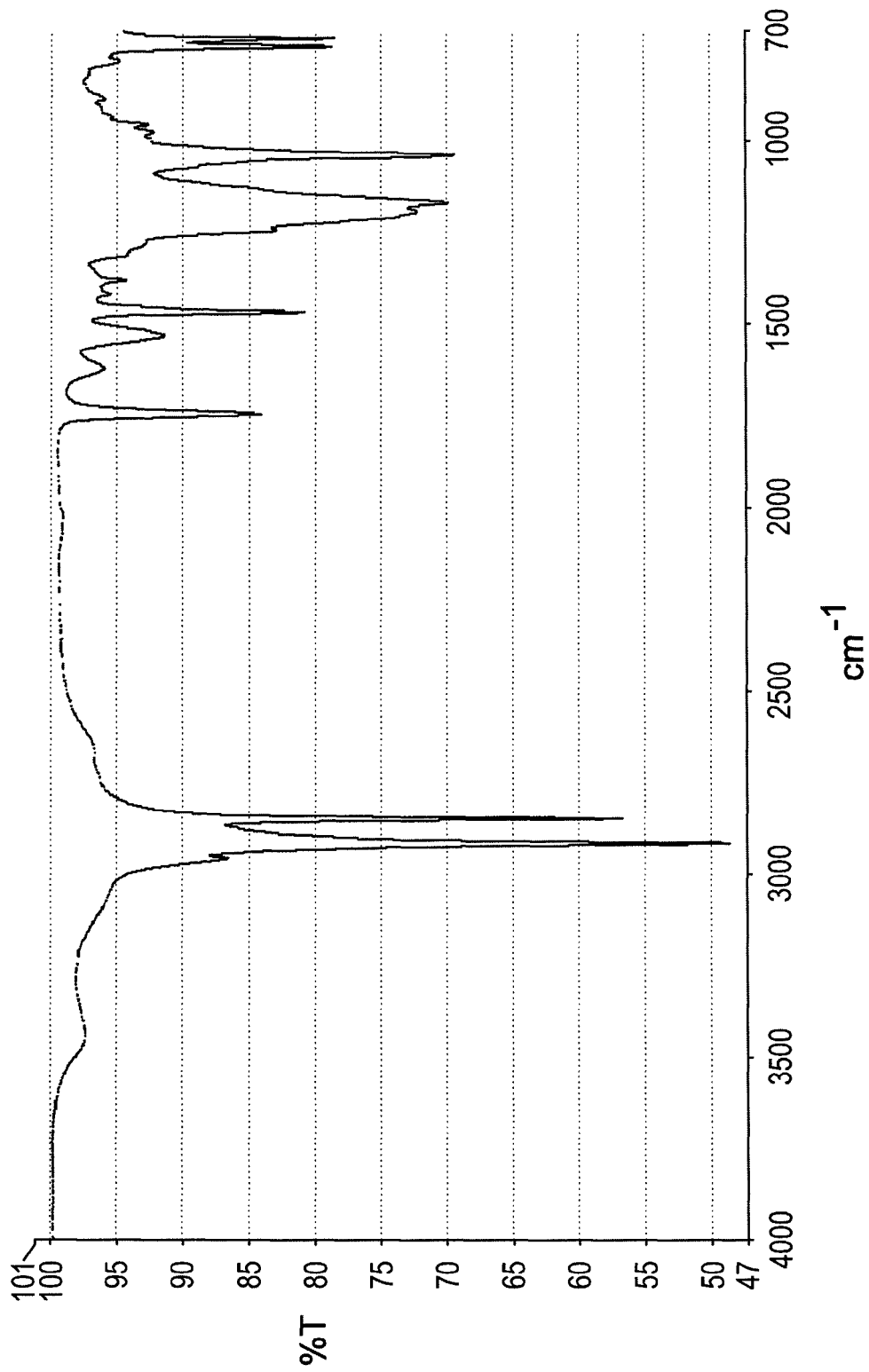
FIG. 1 shows an infrared spectrum of Brassicyl L-isoleucinate esylate (BLIE)
Figure 2:
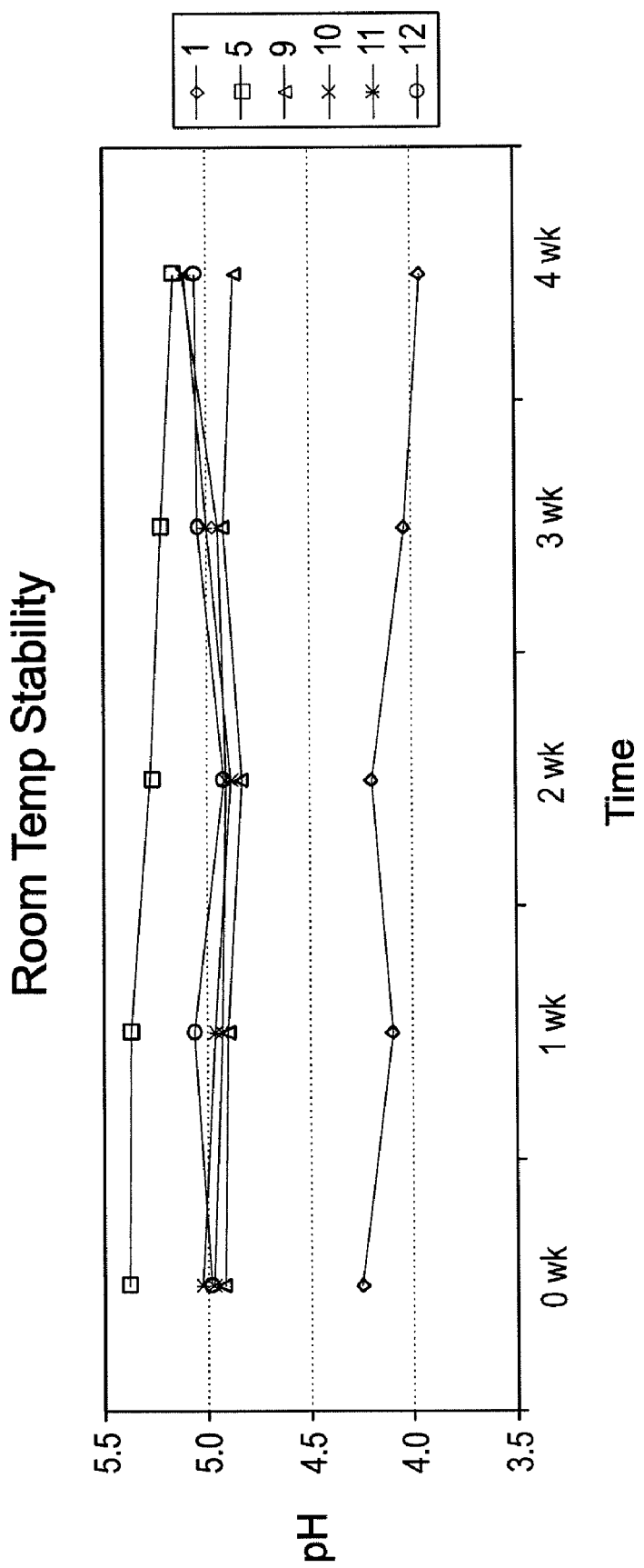
FIGS. 2-9 are graphical representations of the pH of various inventive formulations and control formulations over time at room temperature.
Figure 3:
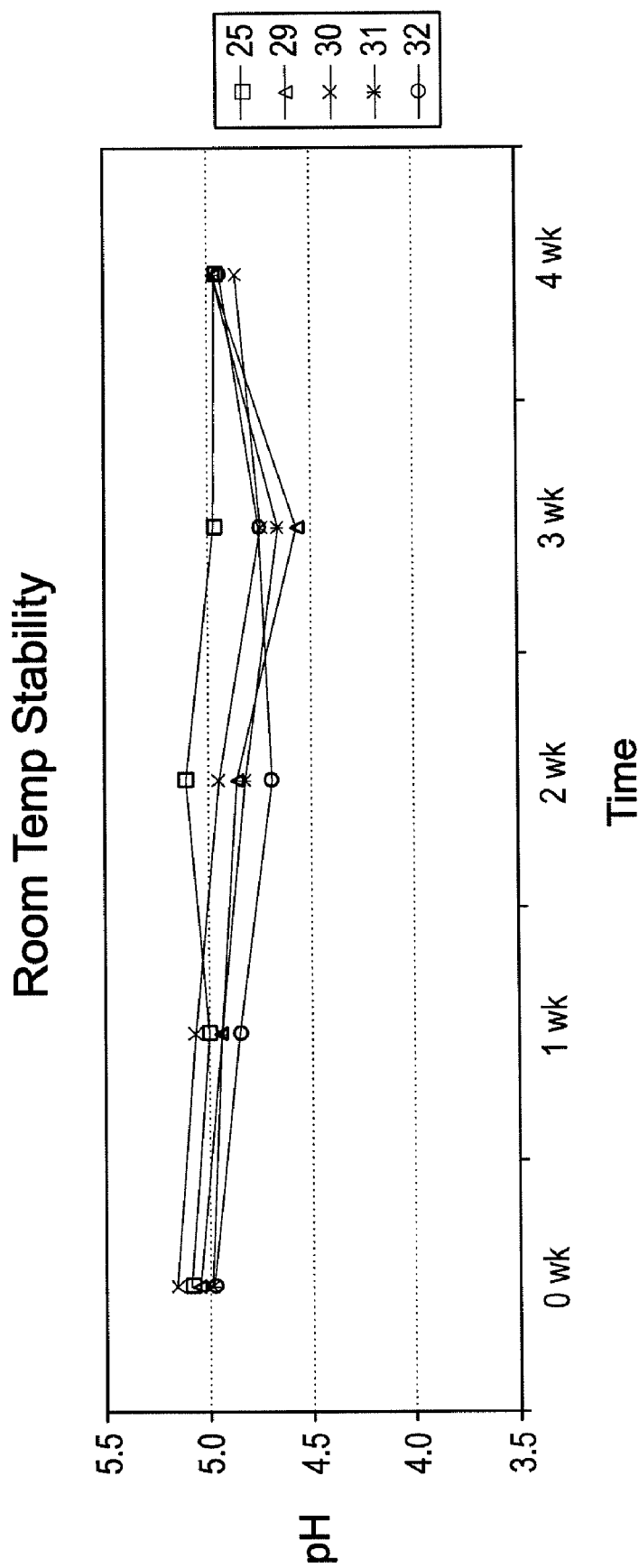
Figure 4:
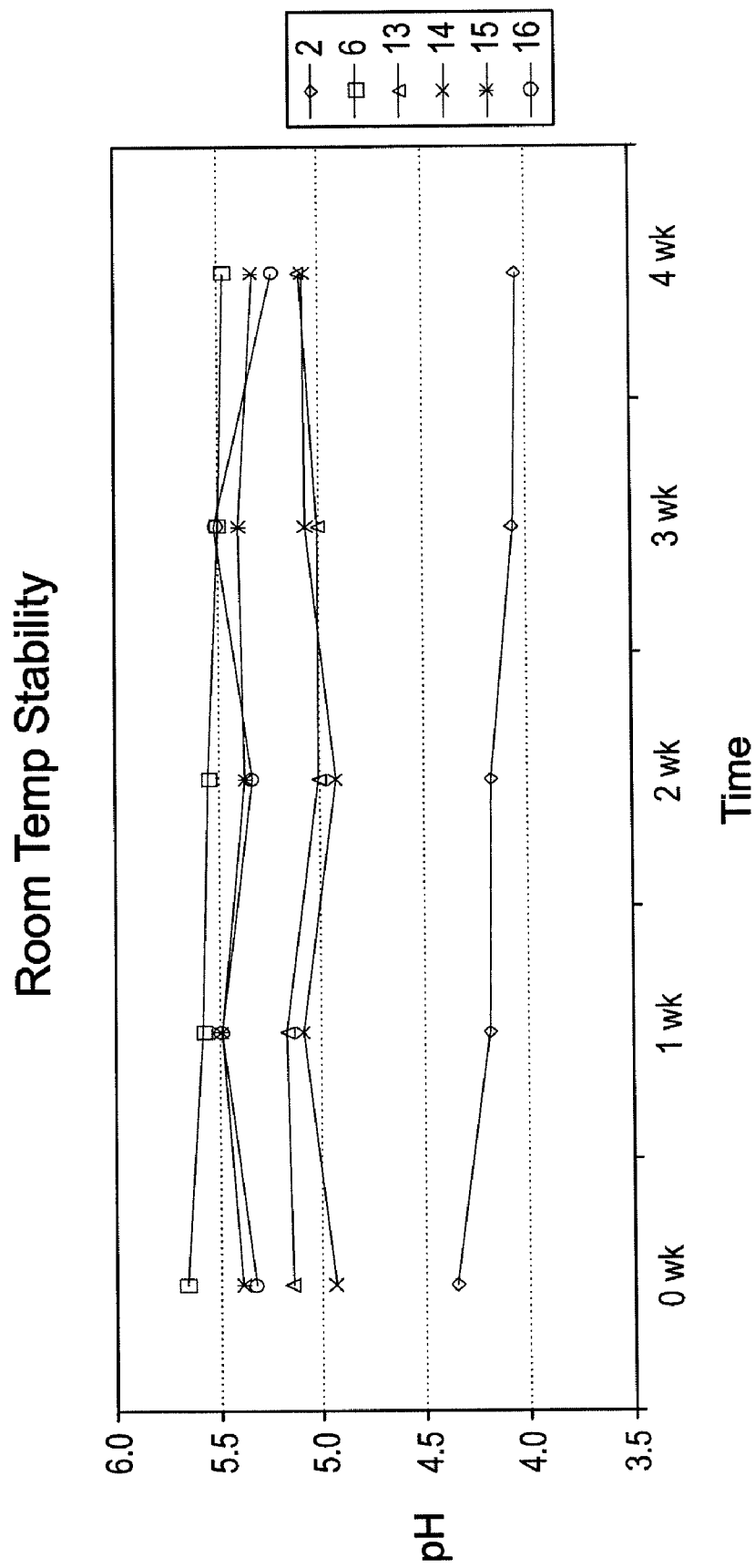
Figure 5:
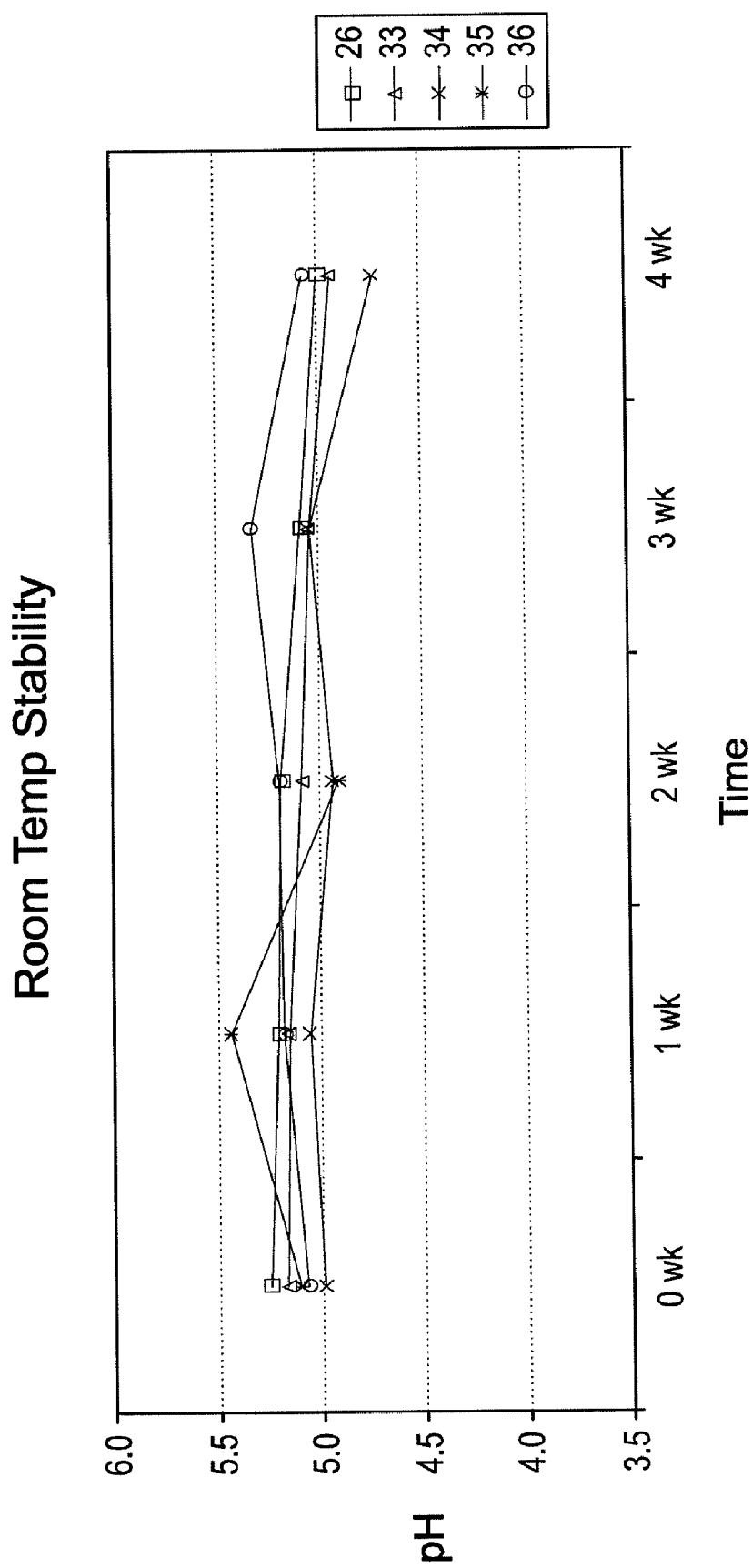
Figure 6:
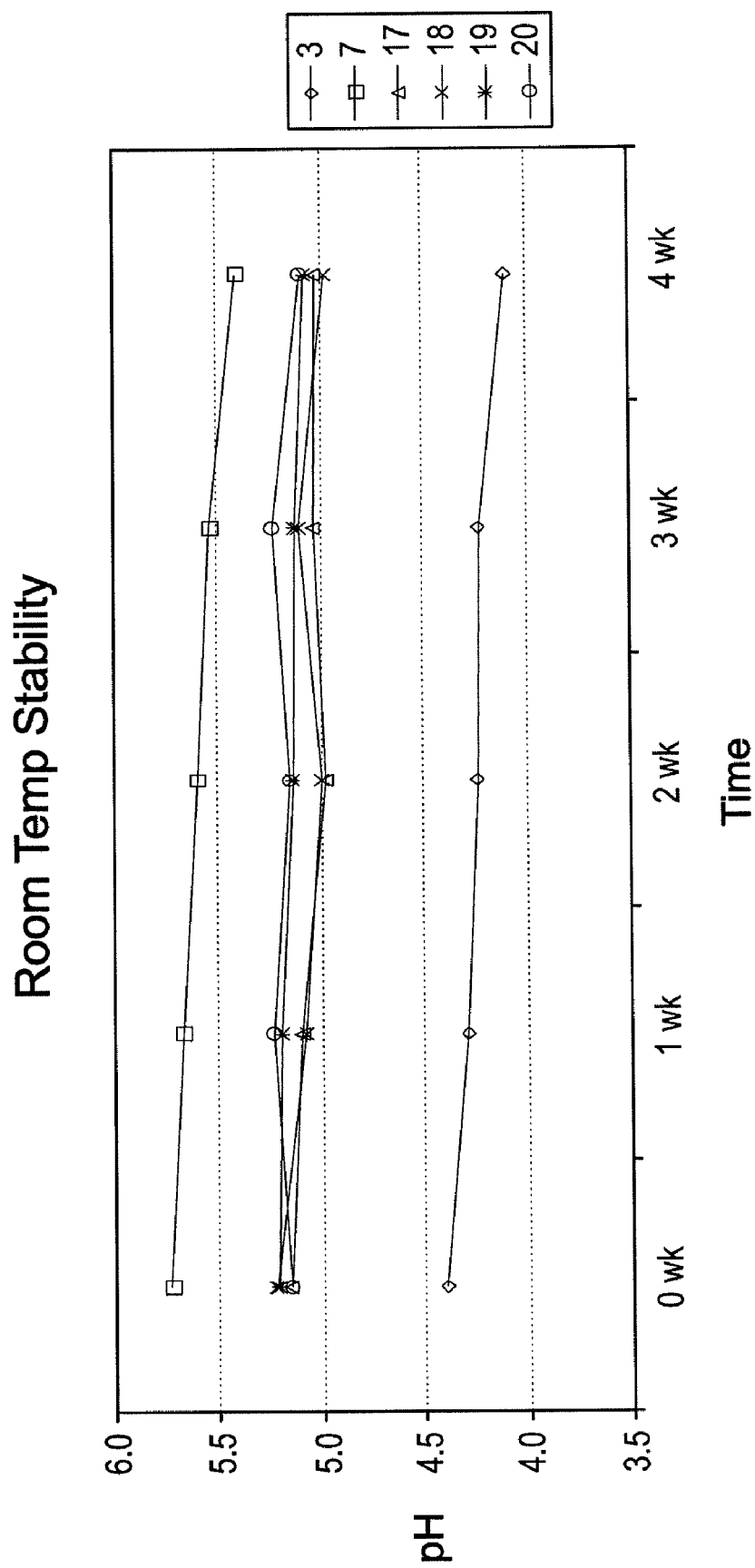
Figure 7:
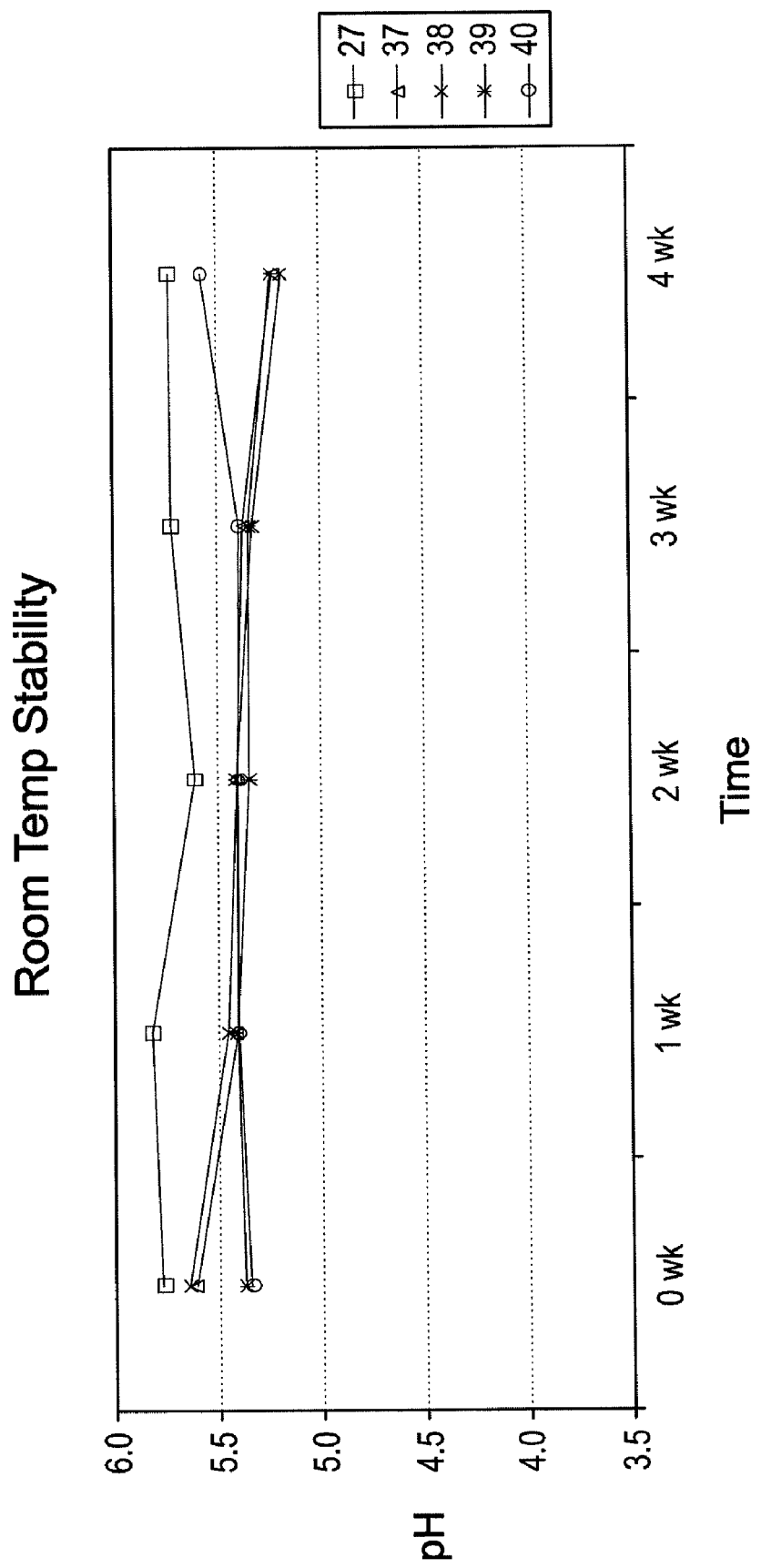
Figure 8:
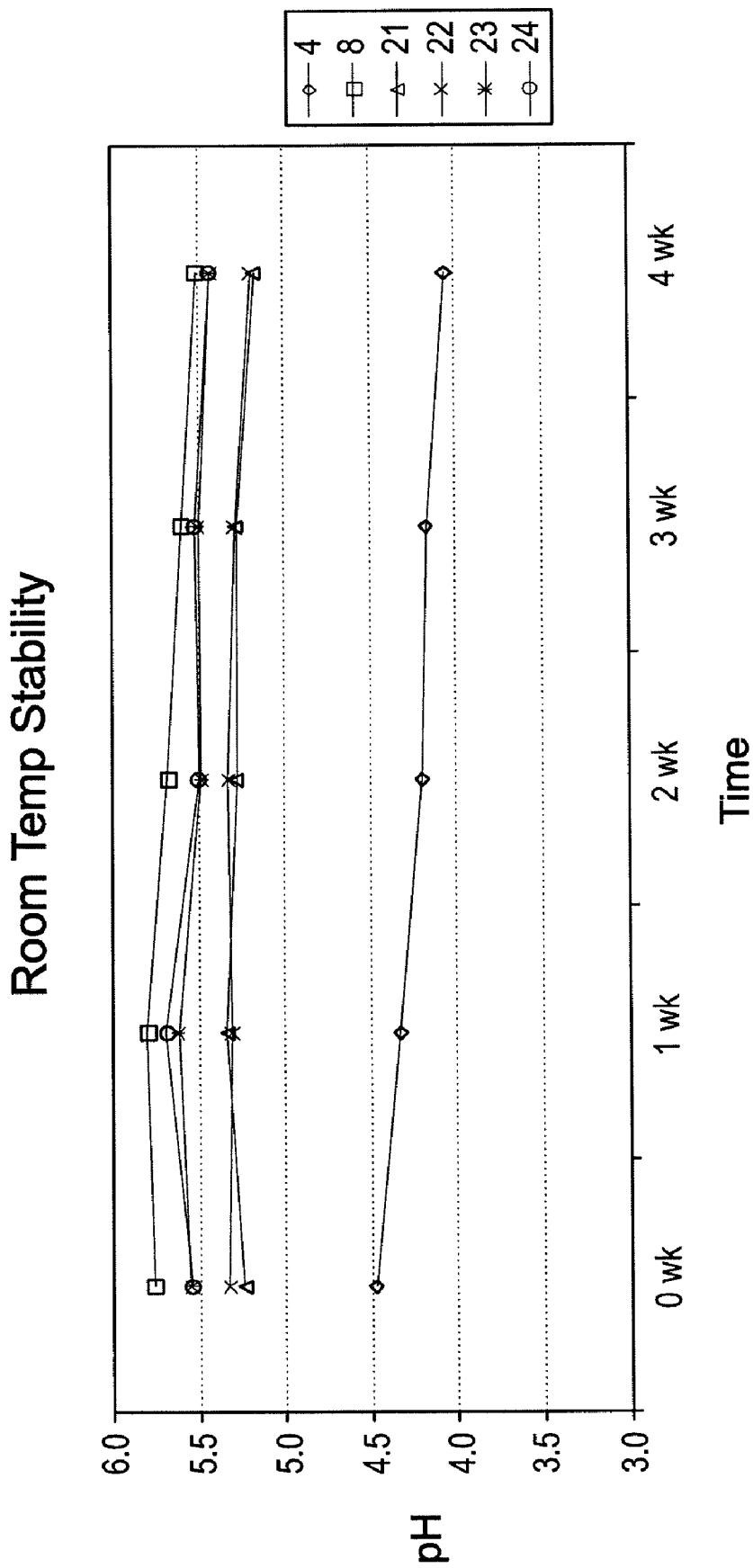
Figure 9:
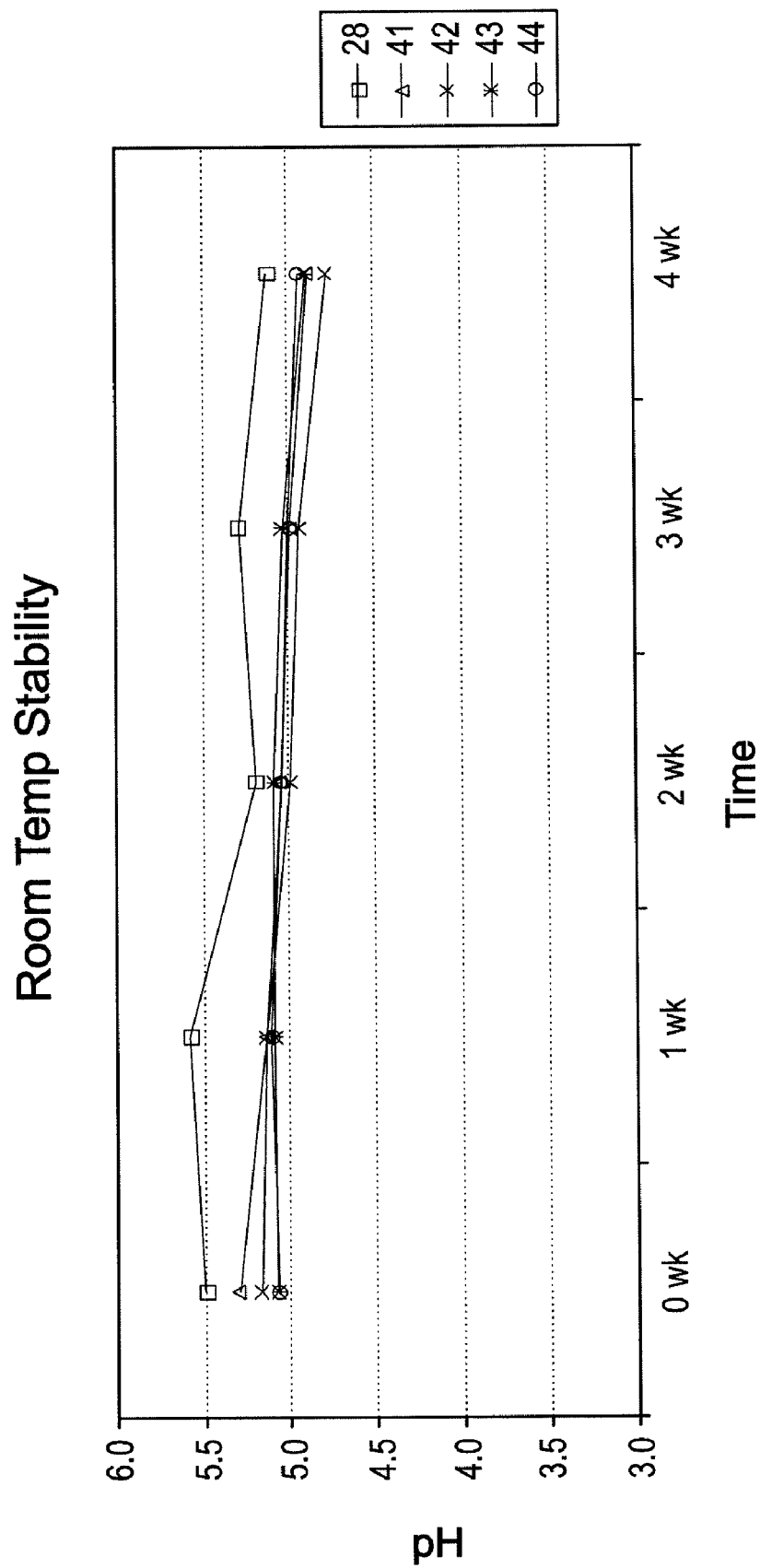

This invention includes neutralized amino acid ester cationic emulsifiers and compositions that are natural, as they are not derived from petrochemical materials, and also may be produced from non-animal derived and non-GMO reactants, and prepared by processes that utilize Green Chemistry principles. Because of the ester's cationic structure, it is well suited for personal care applications, particularly for compositions used in the conditioning of hair and skin. At the time of the invention, no other personal care compositions containing a cationic emulsifier that was not petrochemically-derived were known. Accordingly, up to the time of discovery of the invention, no natural personal care compositions exhibited the performance characteristics provided by a cationic emulsifier and expected by the consumer, particularly with respect to substantivity, skin feel, and shelf stability.

The invention encompasses personal care compositions that contain this emulsifying ester, particularly hair and skin conditioning compositions. Such natural compositions may be substantially free of petrochemicals, petrochemical derivatives, materials derived from genetically modified organisms (such as GMO plant materials), and/or any animal materials or derivatives.

In addition, the neutralized amino acid ester has been found to be non-toxic to animals (including humans) and plants, unlike some cationic emulsifiers which may harm wildlife and/or plants when discharged into the environment.

The invention includes methods of increasing the substantivity (absorbance to a negatively charged substrate, such as hair, skin and nails) of a personal care composition that is substantially free of petrochemicals, petrochemical derivatives, and/or materials derived from genetically modified organisms (such as GMO plant materials), and/or any animal materials or derivatives; therefore the composition itself is natural.

The neutralized amino acid ester of the invention is derived from the esterification of (i) an amino acid having a non-polar side chain wherein the amine group of the amino acid has been neutralized with an acid; with (ii) a long chain fatty alcohol. In particular, suitable amino acid esters are derived from the esterification of a neutral amino acid with a non-polar side chain with a long chain fatty alcohol.

The amino acid ester of the invention may be represented by the structure of formula (I):

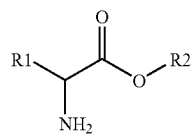

In (I), R¹ represents an alkyl group, which may be branched or linear. It may have one to ten carbon atoms or two to six carbon atoms.

$R^2$ represents a carbon chain that may be linear or branched. It may contain ten to fifty carbon atoms or twenty-four to thirty-two carbon atoms. The chain of $R^2$ may contain at least one unsaturated carbon atom. In an embodiment, $R^2$ is an alkyl group having eight to twenty four carbon atoms.

Amino acids for the formation of the ester include any that are neutral. In an embodiment, one may select L-alanine, L-valine, L-leucine and L-isoleucine. Particularly preferred, in some embodiments of the invention, is L-isoleucine.

It is preferred that the selected neutral amino acid is not derived from animal sources or GMO sources. In an embodiment, it may be preferred that the amino acid(s) are synthetic and/or derived from plants, algae, or other non-animal organisms. They may be obtained, for example, from vegetable matter by a fermentation process.

To obtain the ester of the invention, the amine group of the amino acid is neutralized with an acid, and is reacted with a long chain fatty alcohol. Suitable fatty alcohols may be linear and/or branched and may additionally be saturated and/or unsaturated. It may be preferred that the fatty alcohol contains about ten to about fifty or about twenty-four to about thirty-two carbon atoms. In an embodiment, linear and/or branched fatty alcohols containing from about twelve to about twenty-two carbon atoms may be preferred.

Examples of suitable fatty alcohols include lauryl alcohol, myristyl alcohol, palmityl alcohol, stearyl alcohol, oleyl alcohol, isostearyl alcohol, arachidyl alcohol, behenyl alcohol and mixtures or combinations thereof. It is advisable that the fatty alcohols are derived from non-petrochemical sources.

The amine group of the amino acid ester may be fully or partially neutralized by an acid, to facilitate its cationic behavior. Any acid may be used, including organic and inorganic acids. Suitable acids include, without limitation, mineral acids, amino acids, hydrochloric acid, phosphoric acid, sulfuric acid, boric acid, and nitric acid. Suitable organic acids may be citric acid, ethanesulfonic acid, acetic acid, formic acid, and oxalic acid. Suitable amino acids may include glutamic acid and aspartic acid. In an embodiment, one may prefer ethanesulfonic acid that is derived from non-GMO ethanol.

An exemplary preferred neutralized amino acid ester may be Brassicyl L-isoleucine esylate (BLIE) or leucine isostearyl ester esylate (LIEE). Brassicyl L-isoleucine esylate (BLIE) may be derived from the esterification of Brassica alcohol with L-isoleucine esylate. L-isoleucine esylate may be prepared by reacting the amine group on isoleucine with ethanesulfonic acid. Brassica alcohol is a fatty alcohol that is derived from the splitting of high erucic acid rapeseed oil obtained from the Brassica genus of plants followed by hydrogenation. Brassica alcohol consists predominantly of stearyl ($C_{18}$), arachidyl ($C_{20}$) and behenyl ($C_{22}$) alcohols with minor quantities of lower and higher alkyl chain length alcohols.

The neutralized amino acid ester of the invention may be synthesized by methods commonly known in the art.

The invention also includes personal care compositions that contain the neutralized amino acid ester; such compositions may contain a non-aqueous phase and an aqueous phase that are emulsified by the ester. The compositions are preferably substantially free of petrochemical or petrochemical derivatives. To form such compositions, an exemplary process may be mixing or otherwise incorporating the neutralized amino acid ester with other ingredients of the composition to formulate the finished product.

In an exemplary hair conditioner base formulation, the neutralized amino acid ester is mixed with fatty alcohol and an emollient and is warmed to about 75° C. to about 85° C. This mixture is then added to hot water and allowed to cool slowly with agitation. In such compositions, the neutralized amino acid ester of the invention serves multiple roles—it emulsifies the aqueous and non-aqueous phases of the invention, it increases the substantively of the personal care composition to skin, hair or nails, and it conditions/lubricates the surfaces of the hair, skin or nail substrates to which it is applied.

The composition of the invention may be formulated to be any type of personal care composition, cosmetic, or pharmaceutical delivery formulation (for example, to deliver therapeutic agents to the skin or gums).

Other suitable compositions may include a hair detergent, hair cream conditioner, shampoo, rinse, conditioning shampoo, hair lotions, hair treatment, hair cream, hair spray, hair liquid, hair wax, hair-styling preparation, permanent wave liquids, hair colorant, acidic hair colorant, hair manicure, glaze, skin lotion, milky lotion, face wash, makeup remover, cleansing lotion, emollient lotion, nourishing cream, emollient cream, massage cream, cleansing cream, body shampoo, hand soap, bar soap, shaving creams, sunscreen, sunburn treatment, deodorants, makeup removing gel, moisture gel, moisture essence, UV exposure-preventing essence, shaving foam, face powder, foundation, lipstick, blush, eyeliner, wrinkle and anti-aging cream, eye shadow, eyebrow pencils, mascara, mouthwash, toothpaste, an oral care composition, a skin cleansing composition, a textile cleansing compositions, a dish cleaning composition, a hair or fur cleansing composition, a deodorant or antiperspirant, a cosmetic, a hair styling composition, a skin moisturizer, a skin conditioner, a hair conditioner and a nail conditioner.

The compositions may include various additives, as are known in the personal care composition art. Suitable additives include various anionic surfactants, cationic surfactants, amphoteric surfactants, nonionic surfactants, waxes, other oils and fats and derivatives thereof, fatty acid esters of varying chain lengths, synthetic oils and fats, polymers, alcohols, polyhydric alcohols, extracts useful for providing fragrance, amino acids, nucleic acids, vitamins, hydrolyzed proteins and derivatives thereof, glycerine and derivates thereof, enzymes, anti-inflammatory and other medicaments, microbiocides, antifungals, antiseptics, antioxidants, UV absorbers, dyes and pigments, sunscreen active agents, chelating agents, sweat retardants, oxidizers, pH balancing agents, glyceryl monoesters, moisturizers, peptides and derivatives thereof, anti-aging actives, hair growth promoters, anti-cellulite actives and the like acceptable for use in formulations for human use. Others include EDTA, glutamic acid, glycerine, panthenol, stearyl alcohol, cetyl alcohol, cyclomethicone, dimethicone, pH adjustment additives, and preferably a water base.

Methods that are included within the scope of the invention include methods of conditioning the hair and/or skin by applying the personal care compositions described above. It may be desirable that the composition is in the form of an oil-in-water emulsion, but can also be in a form of, for example, creams, lotions, solutions, gels, pastes, mousses, sprays and combinations thereof. The proportion of the neutralized amino acid ester used in the hair condition composition is preferably from about 0.1 to about 10.0 weight percent, and more preferably from about 0.25 to about 5.0 weight percent.

The compositions may contain a single neutralized amino acid ester or more than one. In an embodiment, the preferred neutralized amino acid ester may be leucine isostearyl ester esylate (LIEE) or Brassicyl L-isoleucinate esylate (BLIE). In some embodiments, it may be preferred to include a mixture of LIEE and BLIE. LIEE and BLIE may be included in any proportion, including, for example, in parts by weight, 1:1, 1:2, 1:3, 1:4, 1:5; 1:6; 1:7; 1:8; 1:9; and 1:10.

Also included are methods of forming an emulsion that includes incorporating the amino acid ester of the invention into a mixture containing at least an aqueous phase and non-aqueous phase.

EXAMPLES

Example 1

Synthesis of Brassicyl L-Isoleucinate Esylate (BLIE)

To a one liter round bottom flask affixed with vapor column, total condenser, nitrogen sparge and agitator, 508.5 grams (1.629 moles) of Brassicyl alcohol and 106.9 grams (0.8147 moles) of L-isoleucine were charged. The mixture was warmed to 90° C. with stirring, and 134.5 grams (0.8551 moles) of a 70% solution of ethanesulfonic acid was added dropwise over about a twenty-minute period. The mixture was then heated to 140° C. and was held for about 16 hours. The mixture was then cooled to 90° C. and the excess of ethanesulfonic acid was neutralized with 1.8 grams of sodium carbonate dissolved in 5.6 grams of water. The mixture was then dried under hard vacuum for about one hour. The mixture was then cooled to about 70° C. and flaked off, yielding a pale yellow solid product.

Acid value was determined on the product using ASTM (American Society of Testing and Materials, West Conshohocken, Pa.) official method number D-972, the contents of which are incorporated herein by reference, and was found to be 2.67 mg KOH/g (95.9% conversion.) The amine value was determined through the use of multi-endpoint titration with base using a modern automatic titrator. In the method, a sample is weighed and dissolved in un-neutralized denatured ethanol. The mixture is then titrated with dilute sodium hydroxide to the appearance of two endpoints, the first being related to the consumption of carboxylate, and the second being related to the titration of the amine salt. The value found was 64.3 mg KOH/g. The infrared spectrum was determined using a Perkin-Elmer (Waltham, Mass.) Spectrum 100 FT-IR spectrophotometer fitted with a Pike (Madison, Wis.) MIRacle ATR (Attenuated Total Reflectance) accessory with ZnSe crystal. The spectrum is displayed in FIG. 1, and shows a prominent peak at 1745 $cm^{-1}$ indicative of ester and the absence of any peak at 1670-1640 $cm^{-1}$ indicative of the absence of amide. The melting point was determined using an SRS (Stanford Research Systems, Inc. Sunnyvale, Calif.) EZMelt automated melting point apparatus and was found to be 55° C.

Example 2

Additional analogs of BLIE were prepared and analyzed using the general methods described in Example 1, and the properties are summarized in Table 1.

TABLE 1

| Amino Acid | Fatty Alcohol | Acid Value (mg KOH/g) | Amine Value (mg KOH/g) | Melting Point (° C.) |
|---|---|---|---|---|
| L-Alanine | Coconut | 0.0 | 106.6 | 78 |
| L-Alanine | Brassicyl (Hyd.) | 3.4 | 71.9 | 99 |
| L-Alanine | Stearyl | 5.5 | 114.6 | 114 |
| L-Alanine | Isostearyl | 1.7 | 76.9 | Paste at R.T. |
| L-Valine | Coconut | 2.5 | 109.0 | Paste at R.T. |
| L-Valine | Brassicyl (Hyd.) | 0.4 | 67.2 | 60 |
| L-Valine | Stearyl | 0.0 | 75.6 | 62 |
| L-Valine | Isostearyl | 1.2 | 73.7 | Liquid at R.T. |
| L-Leucine | Coconut | 2.0 | 97.7 | Liquid at R.T. |
| Leucine | Brassicyl (Hyd.) | 3.5 | 65.4 | 62 |
| L-Leucine | Stearyl | 2.1 | 73.0 | 59 |
| L-Leucine | Isostearyl | 1.8 | 72.1 | Liquid at R.T. |
| L-Isoeucine | Coconut | 5.3 | 103.1 | Liquid at R.T. |
| L-Isoeucine | Stearyl | 1.1 | 72.8 | 53 |

Example 3

To demonstrate the emulsification behavior achieved by the present invention, an exemplary hair conditioning base formulation was prepared. The composition of the formulation is shown in Table 2.

TABLE 2

| Ingredients | % w/w |
|---|---|
| Part A | |
| Deionized water | 90.40 |
| L-Arginine | 0.20 |
| Part B | |
| Stearyl alcohol | 5.90 |
| Brassicyl L-Isoleucinate Esylate | 3.50 |
| Total | 100.00 |

The formulation was prepared using the following procedure. Part A, deionized water and L-arginine were combined in a vessel with propeller agitation and heated to about 70 to about 75° C. and agitated until a clear solution was obtained. In a separate vessel, stearyl alcohol, cetyl alcohol, and Brassicyl L-isoleucinate esylate (BLIE) were combined and heated to about 70° C. to about 75° C., then agitated until a uniform mixture was obtained. The contents of the second vessel were added to the first, and agitated at a temperature of about 70 to about 75° C. until a milky dispersion was obtained (about 10 minutes.) The mixture was then allowed to cool with sweep agitation to about 30° C. to about 35° C. Agitation was then stopped, and the completed conditioner formulation was poured off to containers. What resulted was a white, creamy emulsion that showed no signs of instability for 1 month at 45° C.

Example 4

To illustrate the ability of the invention to create stable emulsions, a stability study was performed. Forty-four formulations were prepared using the general method described in Example 3.

TABLE 3

| | Formula | | | | | | | |
|---|---|---|---|---|---|---|---|---|
| Ingredients | 1 % w/w | 2 % w/w | 3 % w/w | 4 % w/w | 5 % w/w | 6 % w/w | 7 % w/w | 8 % w/w |
| Deionized Water | 88.20 | 86.20 | 84.20 | 82.20 | 88.03 | 85.99 | 83.95 | 81.90 |
| L-Arginine | 0.00 | 0.00 | 0.00 | 0.00 | 0.17 | 0.21 | 0.25 | 0.30 |
| KB Natural | 8.00 | 10.00 | 12.00 | 14.00 | 8.00 | 10.00 | 12.00 | 14.00 |
| Natural Oil | 3.00 | 3.00 | 3.00 | 3.00 | 3.00 | 3.00 | 3.00 | 3.00 |
| Preservative | 0.80 | 0.80 | 0.80 | 0.80 | 0.80 | 0.80 | 0.80 | 0.80 |
| | 100.00 | 100 | 100 | 100 | 100.00 | 100.00 | 100.00 | 100.00 |

| | Formula | | | | | | | |
|---|---|---|---|---|---|---|---|---|
| Ingredients | 9 % wt/wt | 10 % wt/wt | 11 % wt/wt | 12 % wt/wt | 13 % wt/wt | 14 % wt/wt | 15 % wt/wt | 16 % wt/wt |
| Deionized Water | 88.02 | 88.01 | 88.01 | 87.98 | 85.98 | 87.96 | 85.95 | 85.93 |
| Arginine | 0.18 | 0.19 | 0.202 | 0.216 | 0.22 | 0.235 | 0.25 | 0.27 |
| BLIE | 2.79 | 2.98 | 3.17 | 3.39 | 3.49 | 3.73 | 3.97 | 4.24 |
| Cetyl Alcohol | 2.60 | 2.51 | 2.41 | 2.305 | 3.255 | 2.135 | 3.015 | 2.88 |
| Stearyl Alcohol | 2.60 | 2.51 | 2.41 | 2.305 | 3.255 | 2.135 | 3.015 | 2.88 |
| Natural Oil | 3.00 | 3.00 | 3.00 | 3.00 | 3.00 | 3.00 | 3.00 | 3.00 |
| Preservative | 0.80 | 0.80 | 0.80 | 0.80 | 0.80 | 0.80 | 0.80 | 0.80 |
| | 100.00 | 100.00 | 100.00 | 100.00 | 100.00 | 100.00 | 100.00 | 100.00 |

| | Formula | | | | | | | |
|---|---|---|---|---|---|---|---|---|
| Ingredients | 17 % wt/wt | 18 % wt/wt | 19 % wt/wt | 20 % wt/wt | 21 % wt/wt | 22 % wt/wt | 23 % wt/wt | 24 % wt/wt |
| Deionized Water | 83.938 | 83.92 | 83.902 | 83.883 | 81.886 | 81.864 | 81.843 | 81.818 |
| Arginine | 0.262 | 0.28 | 0.298 | 0.317 | 0.314 | 0.336 | 0.357 | 0.382 |

TABLE 3-continued

| Ingredients | | | | | | | | |
|---|---|---|---|---|---|---|---|---|
| BLIE | 4.19 | 4.48 | 4.76 | 5.09 | 4.89 | 5.22 | 5.56 | 5.93 |
| Cetyl Alcohol | 3.905 | 3.76 | 3.62 | 3.455 | 4.55 | 4.39 | 4.22 | 4.035 |
| Stearyl Alcohol | 3.905 | 3.76 | 3.62 | 3.455 | 4.55 | 4.39 | 4.22 | 4.035 |
| Natural Oil | 3.00 | 3.00 | 3.00 | 3.00 | 3.00 | 3.00 | 3.00 | 3.00 |
| Preservative | 0.80 | 0.80 | 0.80 | 0.80 | 0.80 | 0.80 | 0.80 | 0.80 |
| | 100.00 | 100.00 | 100.00 | 100.00 | 100.00 | 100.00 | 100.00 | 100.00 |

| | Formula | | | | | | | |
|---|---|---|---|---|---|---|---|---|
| Ingredients | 25 % wt/wt | 26 % wt/wt | 27 % wt/wt | 28 % wt/wt | 29 % wt/wt | 30 % wt/wt | 31 % wt/wt | 32 % wt/wt |
| Deionized Water | 88.11 | 86.09 | 84.08 | 82.05 | 88.09 | 88.09 | 88.09 | 88.07 |
| Arginine | 0.085 | 0.105 | 0.124 | 0.147 | 0.1068 | 0.114 | 0.1212 | 0.1296 |
| BLIE | 2.67 | 3.33 | 4.00 | 4.67 | 2.79 | 2.98 | 3.17 | 3.39 |
| Cetyl Alcohol | 2.67 | 3.33 | 4.00 | 4.67 | 2.605 | 2.51 | 2.41 | 2.305 |
| Stearyl Alcohol | 2.67 | 3.33 | 4.00 | 4.67 | 2.605 | 2.51 | 2.41 | 2.305 |
| Natural Oil | 3.00 | 3.00 | 3.00 | 3.00 | 3.00 | 3.00 | 3.00 | 3.00 |
| Preservative | 0.80 | 0.80 | 0.80 | 0.80 | 0.80 | 0.80 | 0.80 | 0.80 |
| | 100.00 | 100.00 | 100.00 | 100.00 | 100.00 | 100.00 | 100.00 | 100.00 |

| | Formula | | | | | | | |
|---|---|---|---|---|---|---|---|---|
| Ingredients | 33 % wt/wt | 34 % wt/wt | 35 % wt/wt | 36 % wt/wt | 37 % wt/wt | 38 % wt/wt | 39 % wt/wt | 40 % wt/wt |
| Deionized Water | 86.07 | 88.06 | 86.05 | 86.04 | 84.07 | 84.06 | 84.051 | 84.041 |
| Arginine | 0.132 | 0.141 | 0.15 | 0.1602 | 0.131 | 0.14 | 0.149 | 0.159 |
| BLIE | 3.49 | 3.73 | 3.97 | 4.24 | 4.19 | 4.48 | 4.76 | 5.09 |
| Cetyl Alcohol | 3.255 | 2.135 | 3.015 | 2.88 | 3.905 | 3.76 | 3.62 | 3.455 |
| Stearyl Alcohol | 3.255 | 2.135 | 3.015 | 2.88 | 3.905 | 3.76 | 3.62 | 3.455 |
| Natural Oil | 3.00 | 3.00 | 3.00 | 3.00 | 3.00 | 3.00 | 3.00 | 3.00 |
| Preservative | 0.80 | 0.80 | 0.80 | 0.80 | 0.80 | 0.80 | 0.80 | 0.80 |
| | 100.00 | 100.00 | 100.00 | 100.00 | 100.00 | 100.00 | 100.00 | 100.00 |

| | Formula | | | |
|---|---|---|---|---|
| Ingredients | 41 % wt/wt | 42 % wt/wt | 43 % wt/wt | 44 % wt/wt |
| Deionized Water | 81.42 | 82.032 | 82.022 | 82.01 |
| Arginine | 0.785 | 0.168 | 0.178 | 0.191 |
| BLIE | 4.89 | 5.22 | 5.56 | 5.93 |
| Cetyl Alcohol | 4.55 | 4.39 | 4.22 | 4.035 |
| Stearyl Alcohol | 4.55 | 4.39 | 4.22 | 4.035 |
| Natural Oil | 3.00 | 3.00 | 3.00 | 3.00 |
| Preservative | 0.80 | 0.80 | 0.80 | 0.80 |
| | 100.00 | 100.00 | 100.00 | 100.00 |

The pH and viscosity at 25° C. were performed on each of the formulations, and the results are found in Table 4. The pH was measured using an Orion 420A pH meter with a glass electrode that was calibrated using aqueous buffer solutions. The clean, dry electrode was placed in each sample at 25° C. for approximately 1 minute and the pH was recorded directly from the meter display. The viscosity was determined using a Brookfield RVT dial viscometer with helipath stand and T-bar spindles. The test emulsion was equilibrated at 25° C. before taking each measurement. The spindle was attached to the instrument and lowered into the test formula. The viscometer and helipath stand were turned on and the viscosity measurement was recorded after a period of 60 seconds.

TABLE 4

| | Formula | | | | | | | | | |
|---|---|---|---|---|---|---|---|---|---|---|
| | 1 | 2 | 3 | 4 | 5 | 6 | 7 | 8 | 9 | 10 |
| pH | 4.25 | 4.35 | 4.4 | 4.48 | 5.38 | 5.66 | 5.73 | 5.76 | 4.92 | 4.97 |
| Viscosity | 18500 | 20000 | 22800 | 66500 | 41000 | 54000 | 69000 | 75500 | 4000 | 6000 |

| | Formula | | | | | | | | | |
|---|---|---|---|---|---|---|---|---|---|---|
| | 11 | 12 | 13 | 14 | 15 | 16 | 17 | 18 | 19 | 20 |
| pH | 5.02 | 4.98 | 5.15 | 4.94 | 5.39 | 5.33 | 5.16 | 5.23 | 5.22 | 5.16 |
| Viscosity | 7000 | 11500 | 35500 | 9000 | 56000 | 43500 | 57000 | 61000 | 47000 | 54000 |

TABLE 4-continued

| | Formula | | | | | | | | | |
|---|---|---|---|---|---|---|---|---|---|---|
| | 21 | 22 | 23 | 24 | 25 | 26 | 27 | 28 | 29 | 30 |
| pH | 5.24 | 5.33 | 5.55 | 5.54 | 5.09 | 5.26 | 5.27 | 5.49 | 5.05 | 5.16 |
| Viscosity | 51000 | 77000 | 69000 | 80000 | 35000 | 59000 | 73000 | 83000 | 23000 | 16000 |

| | Formula | | | | | | | | | |
|---|---|---|---|---|---|---|---|---|---|---|
| | 31 | 32 | 33 | 34 | 35 | 36 | 37 | 38 | 39 | 40 |
| pH | 4.99 | 4.98 | 5.17 | 4.99 | 5.05 | 5.07 | 5.11 | 5.14 | 4.87 | 4.84 |
| Viscosity | 25000 | 27000 | 46000 | 24000 | 42000 | 47500 | 91000 | 65000 | 18000 | 72000 |

| | Formula | | | |
|---|---|---|---|---|
| | 41 | 42 | 43 | 44 |
| pH | 5.3 | 5.17 | 5.08 | 5.07 |
| Viscosity | 92000 | Too thick | Too thick | 81000 |

All formulations were transferred to canisters to test for stability. Stability is defined as the ability of the emulsion to retain its initial, creamy uniform texture, and to not separate. The test was performed at room temperature for a period of four weeks. Formulation pH was monitored weekly. FIGS. 2 through 9 show the pH as a function of storage time. In each case, pH changed very little over the entire course of the study for all formulations, and all formulations retained their initial physical form and characteristics.

Example 5

To demonstrate the conditioning properties of the inventive cationic emulsifiers, a model hair conditioning formulation was prepared to test for the reduction in flyaway hair. The composition of the inventive formulation (Inventive Formulation A) is shown in Table 5 below:

TABLE 5

| Inventive Formulation A | |
|---|---|
| Ingredients | % w/w |
| Part A | |
| Deionized water | 88.060 |
| L-Arginine | 0.141 |
| BLIE | 3.730 |
| Part B | |
| Stearyl alcohol | 2.135 |
| Cetyl Alcohol | 2.135 |
| Almond Oil | 3.000 |
| Part C | |
| Preservative | 0.800 |
| Total | 100.000 |

The Inventive Formulation A was tested against industry leader commercial products Pantene Pro-V Daily Moisture Renewal and Garnier Fructis Fortifying Cream Conditioner. The cationic emulsifier utilized in Pantene Pro-V Daily Moisture Renewal is stearamidopropyl dimethylamine, while the Garnier Fructis Fortifying Cream Conditioner utilizes behentrimonium chloride.

Ten tresses of hair were washed with Pantene clarifying shampoo and rinsed under deionized water for 1 minute. The tresses were combed, and were immersed in conditioner for 1 minute, then rinsed under deionized water for 1 minute and hung to dry for 2 hours. The tresses were then dried with a hair dryer on low for 5 minutes and hung to dry another 15 minutes. The width at the bottom of the tress was recorded, it was combed 20 times, and the width was recorded again. The data obtained are recorded in Tables 6, 7, and 8.

TABLE 6

| Inventive Formulation A | Pre comb width (cm) | Post-comb width (cm) | Difference | % Fly Away |
|---|---|---|---|---|
| 1 | 5.0 | 7.3 | 2.3 | 31.51 |
| 2 | 4.3 | 5.4 | 1.1 | 20.37 |
| 3 | 5.7 | 5.8 | 0.1 | 1.72 |
| 4 | 4.8 | 6.2 | 1.4 | 22.58 |
| 5 | 5.2 | 6.8 | 1.6 | 23.53 |
| 6 | 5.3 | 5.9 | 0.6 | 10.17 |
| 7 | 5.2 | 4.4 | −0.8 | −18.18 |
| 8 | 4.3 | 4.8 | 0.5 | 10.42 |
| 9 | 4.5 | 6.2 | 1.7 | 27.42 |
| 10 | 4.9 | 5.1 | 0.2 | 3.92 |
| Average | 4.92 | 5.79 | 0.87 | 13.35 |

TABLE 7

| Pantene | Pre comb width (cm) | Post-comb width (cm) | Difference | % Fly Away |
|---|---|---|---|---|
| 1 | 4.1 | 5.5 | 1.4 | 25.45 |
| 2 | 4.5 | 5.1 | 0.6 | 11.76 |
| 3 | 3.9 | 4.2 | 0.3 | 7.14 |
| 4 | 2.9 | 4.5 | 1.6 | 35.56 |
| 5 | 4.5 | 5.3 | 0.8 | 15.09 |
| 6 | 3.9 | 4.2 | 0.3 | 7.14 |
| 7 | 4.1 | 5.3 | 1.2 | 22.64 |
| 8 | 4.5 | 5.5 | 1.0 | 18.18 |
| 9 | 4.1 | 4.1 | 0.0 | 0.00 |
| 10 | 3.2 | 4.3 | 1.1 | 25.58 |
| Average | 4.0 | 4.8 | 0.8 | 16.86 |

TABLE 8

| Garnier | Pre comb width (cm) | Post-comb width (cm) | Difference | % Fly Away |
|---|---|---|---|---|
| 1 | 3.0 | 4.3 | 1.3 | 30.23 |
| 2 | 2.9 | 4.8 | 1.9 | 39.58 |
| 3 | 3.7 | 4.4 | 0.7 | 15.91 |
| 4 | 3.1 | 4.3 | 1.2 | 27.91 |

TABLE 8-continued

| Garnier | Pre comb width (cm) | Post-comb width (cm) | Difference | % Fly Away |
|---|---|---|---|---|
| 5 | 2.1 | 3.2 | 1.1 | 34.38 |
| 6 | 3.0 | 3.9 | 0.9 | 23.08 |
| 7 | 2.9 | 3.3 | 0.4 | 12.12 |
| 8 | 3.2 | 4.2 | 1.0 | 23.81 |
| 9 | 2.2 | 3.3 | 1.1 | 33.33 |
| 10 | 3.0 | 4.1 | 1.1 | 26.83 |
| Average | 2.9 | 4.0 | 1.1 | 26.72 |

The results show that there was less fly-away using Inventive Formulation A when compared with Pantene and Garnier conditioners. Therefore, the Inventive Formulation A is just as effective, if not more effective, than Pantene and Garnier (both of which contain petrochemicals and/or petrochemical-derived materials) at conditioning hair.

Example 6

The Rubine Dye Test was used to evaluate the substantivity of Inventive Formulation A versus market standards Pantene and Garnier as in Example 5. Rubine Dye is an anionic dye which will readily react with cationic materials. When light blonde hair or wool is treated with a cationic conditioner and rinsed, the hair or wool turns reddish pink when dipped into a dilute solution of Rubine Dye. This study was performed to evaluate the deposition of Direct Red, an anionic dye solution, onto conditioned hair to measure the degree of cationic charge due to substantivity of the conditioner to the hair.

Figure 10:
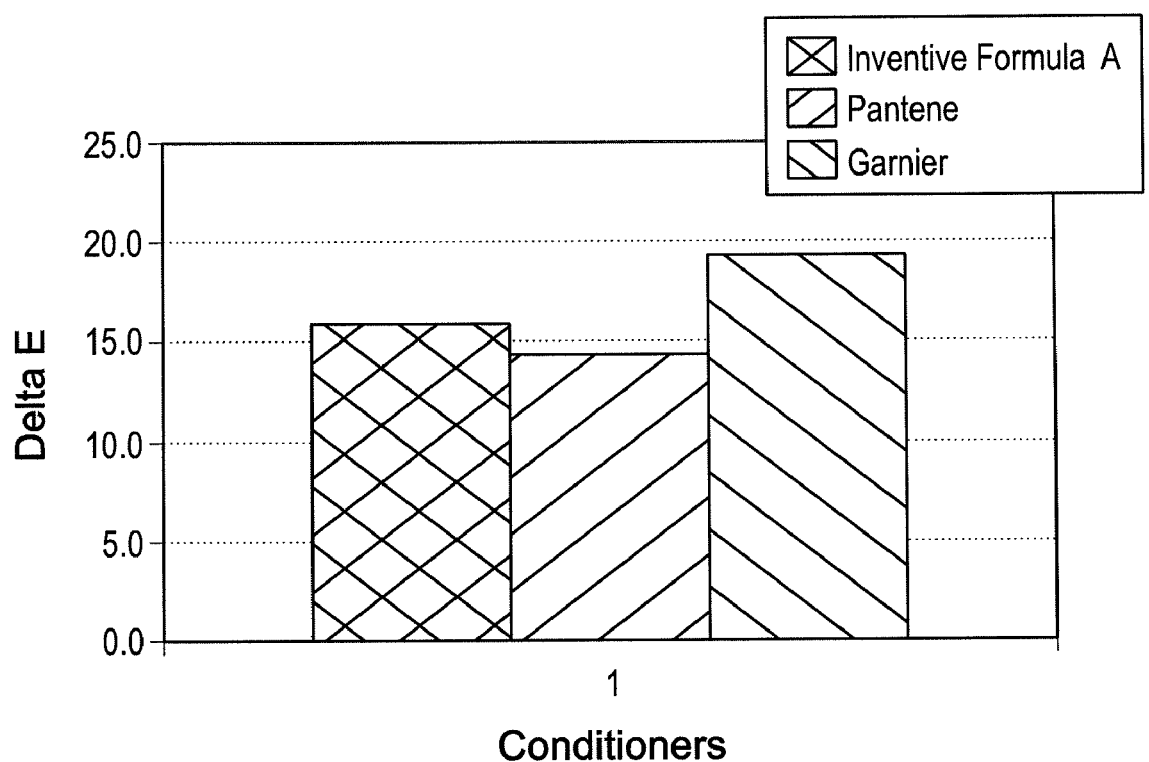
FIG. 10 is a graph showing the results of a colorimetric analysis of sample hair, untreated and treated with the inventive and commercially available, non-natural control compositions.

A stock dye solution was prepared by combining deionized water (99.37%) Direct Red 80 dye (0.50%) and glacial acetic acid (0.13%) until a uniform solution was obtained. This solution was further diluted by mixing the stock dye solution with deionized water at a ratio of one to four to create the Test Dye Solution. Prebleached hair was glued to plastic strips weighing 0.60+/−0.02 grams each. Ten swatches were prepared for each conditioner to be tested. Each swatch was individually wet under warm running water, then washed with two grams of cationic conditioner for one minute. Each sample was then rinsed under warm running water for two minutes and excess water was removed by blotting with a paper towel. Each hair sample was then immersed in 200 ml if Test Dye Solution for 10 seconds, then rinsed under running water for 5 seconds. Excess water was removed by blotting between two paper towels and then hung to dry. Qualitative and quantitative comparisons of dye uptake and relative substantivity of each cationic conditioner was evaluated using a digital camera and Minolta Chroma Meter. FIG. 10 shows the level of color as determined by the Minolta Chroma Meter in terms of delta E. The Minolta Chroma Meter measures chromaticity, tristimulus values, color difference, correlated color temperature and the illuminance of light sources. The delta E value is given by equation below. Higher delta E relates to higher color.

$$\Delta E = \Delta L^2 + \Delta a^2 + \Delta b^2$$

The results of this study indicate that Formulation A performs comparably to behentrimonium chloride (Garnier) and stearamidopropl dimethylamine (Pantene) based conditioners. The Formulation A conditioner was slightly more substantive than the Pantene, but less than Garnier, and well within commercially acceptable parameters. The results are expressed as $\Delta E$, which accounts for variations in tone and hue versus the unconditioned tresses.

Example 7

Exemplary formulations for hair and skin care compositions are shown below (formulations A to M). None contains petrochemicals and/or petrochemical-derived materials.

| Ingredients | % w/w |
|---|---|
| A. Daily Conditioner for Normal Hair | |
| Part A | |
| Deionized water | 84.05 |
| L-Arginine | 0.15 |
| BLIE | 4.50 |
| Part B | |
| Stearyl alcohol | 3.75 |
| Cetyl Alcohol | 3.75 |
| Caprylic/Capric Triglycerides | 3.00 |
| Part C | |
| Preservative | 0.80 |
| Total | 100.00 |
| B. Intense Moisturizing Hair Conditioner | |
| Part A | |
| Deionized water | 74.34 |
| L-Arginine | 0.16 |
| BLIE | 5.20 |
| Glycerine | 5.00 |
| Part B | |
| Cetearyl Alcohol | 7.50 |
| *Helianthus Annuus* (Sunflower) Seed Oil | 6.50 |
| Hydrolyzed Silk Protein | 0.50 |
| Part C | |
| Preservative | 0.80 |
| Total | 100.00 |
| C. Leave-In Hair Conditioning Treatment | |
| Part A | |
| Deionized water | 89.11 |
| L-Arginine | 0.14 |
| BLIE | 3.75 |
| Part B | |
| Cetyl Alcohol | 2.10 |
| Stearyl Alcohol | 2.10 |
| *Olea Europaea* (Olive) Fruit Oil | 2.00 |
| Part C | |
| Preservative | 0.80 |
| Total | 100.00 |
| D. Rich Conditioning Treatment (Hair) | |
| Part A | |
| Deionized water | 81.05 |
| L-Arginine | 0.15 |
| BLIE | 4.50 |
| Part B | |
| Cetyl Alcohol | 3.75 |
| Stearyl Alcohol | 3.75 |
| *Olea Europaea* (Olive) Fruit Oil | 2.00 |
| Part C | |
| Preservative | 0.80 |
| Total | 100.00 |

| Ingredients | % w/w |
|---|---|
| E. Baby Lotion (Skin) | |
| Part A | |
| Deionized water | 80.25 |
| L-Arginine | 00.25 |
| Glycerin | 2.00 |
| Part B | |
| BLIE | 3.00 |
| *Brassica* Alcohol | 3.00 |
| *Brassica* Glycerides | 2.00 |
| Heptyl Undecylenate | 4.00 |
| *Helianthus Annuus* (Sunflower) Seed Oil | 4.00 |
| Glyceryl Monocaprylate | 1.00 |
| Part C | |
| Natural Fragrance | 0.30 |
| Total | 100.00 |
| F. Rich Body Butter (Skin) | |
| Part A | |
| Deionized water | 68.04 |
| L-Arginine | 0.16 |
| Glycerine | 4.00 |
| *Aloe Barbadensis* Leaf Juice | 1.00 |
| Part B | |
| BLIE | 5.20 |
| Cetyl Alcohol | 3.50 |
| Behenyl Alcohol | 3.50 |
| Heptyl Undecylenate | 5.00 |
| *Olea Europaea* (Olive) Fruit Oil | 7.00 |
| *Butyrospermum Parkii* (Shea) Butter | 1.50 |
| Part C | |
| Preservative | 0.80 |
| Natural Fragrance | 0.30 |
| Total | 100.00 |
| G. Conditioning Cream (Hair) | |
| Part A | |
| Deionized water | 85.30 |
| L-Arginine | 0.15 |
| Glycerine | 0.50 |
| Part B | |
| BLIE | 3.70 |
| *Brassica* Alcohol | 6.55 |
| *Helianthus Annuus* (Sunflower) Seed Oil | 3.00 |
| Part C | |
| Preservative | 0.80 |
| Total | 100.00 |
| H. Deep Conditioning Treatment (Hair) | |
| Part A | |
| Deionized water | 76.55 |
| L-Arginine | 0.25 |
| Glycerine | 0.50 |
| Part B | |
| BLIE | 4.00 |
| *Brassica* Alcohol | 7.00 |
| Heptyl Undecylenate | 3.00 |
| Caprylic/Capric Triglyceride | 1.00 |
| Cetyl Alcohol | 5.00 |
| Polyester-11 | 0.50 |
| Part C | |
| Keratin Amino Acids | 1.00 |
| Glyceryl Monocaprylate | 1.20 |
| Total | 100.00 |
| I. Moisturizing Conditioner for Curly Hair | |
| Part A | |
| Deionized water | 75.05 |
| L-Arginine | 0.25 |
| Sorbitol | 2.00 |
| Glyceryl Monocaprylate | 1.00 |
| Panthenol | 0.50 |
| Glycerine | 2.50 |
| Polyester-11 | 0.50 |
| Part B | |
| BLIE | 4.00 |
| Cetearyl Alcohol | 10.00 |
| Caprylic/Capric Triglyceride | 1.00 |
| *Olea Europaea* (Olive) Oil | 2.00 |
| Part C | |
| Hydrolyzed Wheat Protein | 1.00 |
| Total | 100.00 |
| J. Light Daily Conditioner (Hair) | |
| Part A | |
| Deionized water | 89.20 |
| L-Arginine | 0.20 |
| Glycerine | 0.50 |
| Glyceryl Monocaprylate | 1.00 |
| Part B | |
| BLIE | 1.80 |
| *Brassica* Alcohol | 3.20 |
| Heptyl Undecylenate | 1.00 |
| Cetyl Alcohol | 3.00 |
| Part C | |
| Natural Fragrance | 0.10 |
| Total | 100.00 |
| K. Leave-In Conditioning Spray (Hair) | |
| Part A | |
| Deionized water | 91.25 |
| L-Arginine | 0.15 |
| Glycerine | 0.50 |
| Glyceryl Monocaprylate | 1.00 |
| Part B | |
| BLIE | 1.25 |
| *Brassica* Alcohol | 2.25 |
| Heptyl Undecylenate | 1.00 |
| Cetyl Alcohol | 1.50 |
| *Olea Europaea* (Olive) Oil | 0.50 |
| Part C | |
| Hydrolyzed Silk Protein | 0.50 |
| Natural Fragrance | 0.10 |
| Total | 100.00 |
| L. Deluxe Moisturizer | |
| Part A | |
| Deionized water | 56.85 |
| L-Arginine | 0.15 |
| Glycerine | 5.00 |

-continued

| Ingredients | % w/w |
|---|---|
| Part B | |
| BLIE | 4.50 |
| Brassica Alcohol | 4.50 |
| Brassica Glycerides | 3.00 |
| Caprylic/Capric Triglyceride | 25.00 |
| Glyceryl Monocaprylate | 1.00 |
| Total | 100.00 |
| M. Sprayable Hydrating Lotion (Skin) | |
| Part A | |
| Deionized water | 84.30 |
| L-Arginine | 0.20 |
| Glycerine | 5.00 |
| Glyceryl Monocaprylate | 1.00 |
| Part B | |
| BLIE | 2.05 |
| Brassica Alcohol | 2.05 |
| Brassica Glycerides | 1.40 |
| Caprylic/Capric Triglyceride | 4.00 |
| Total | 100.00 |

Example 8

Two conditioning formulations in accordance with the invention were prepared specifically to evaluate the aesthetic characteristics of the formulations. Each was prepared with out any petrochemical materials. Formulation K included both leucine isostearyl ester esylate (LIEE) and Brassicyl L-isoleucinate esylate (BLIE). Formulation C included BLIE only.

The formulations were prepared simultaneously using the following procedure. With reference to Table 8 below, Part A, deionized water, glycerine and arginine were combined in a vessel with propeller agitation and heated to about 70 to about 75° C. and agitated until a clear solution was obtained. In a separate vessel, Brassica alcohol, cetyl alcohol, heptyl undecylenate, caprylic/capric triglyceride, glyceryl monocaprylate and Brassicyl L-isoleucinate esylate (BLIE) were combined and heated to about 70° C. to about 75° C., then agitated until a uniform mixture was obtained. The contents of the second vessel were added to the first, and agitated at a temperature of about 70 to about 75° C. until a milky dispersion was obtained (about 10 minutes.) The mixture was then allowed to cool with sweep agitation to about 30° C. to about 35° C. Agitation was then stopped, and the completed conditioner formulation was poured off to containers.

TABLE 8

| Ingredients | K % w/w | C % w/w |
|---|---|---|
| Part A | | |
| Deionized water | 77.05 | 78.05 |
| L-Arginine | 0.25 | 0.25 |
| Glycerine | 0.50 | 0.50 |
| Part B | | |
| BLIE | 4.00 | 4.00 |
| Brassica Alcohol | 7.00 | 7.00 |
| Heptyl Undecylenate | 3.00 | 3.00 |
| Caprylic/Capric Triglyceride | 1.00 | 1.00 |
| Cetyl Alcohol | 5.00 | 5.00 |

TABLE 8-continued

| Ingredients | K % w/w | C % w/w |
|---|---|---|
| Leucine Isostearyl Ester Esylate | 1.00 | 0 |
| Glyceryl Monocaprylate | 1.20 | 1.20 |
| Total | 100.00 | 100.00 |

Test formula K was a milky, creamy emulsion while hot and cooled to a smooth uniform emulsion with a glossy finish. Test formula C was thicker and the resulting emulsion was grainy and dull in appearance. Test formula C, without LIEE, was less stable at elevated temperature. Test formula K was stable for 90 days at 25° C. and 45° C.

Example 9

A conditioning cream in accordance with the invention was prepared by incorporating the ingredients of Part A (Table 9, below) and Part B (Table 9, below), and subsequently mixing Parts A and B together.

TABLE 9

Conditioning Cream

| Ingredients | % w/w |
|---|---|
| Part A | |
| Deionized water | 85.30 |
| L-Arginine | 0.15 |
| Glycerin | 0.50 |
| Part B | |
| BLIE | 3.70 |
| Brassica Alcohol | 6.55 |
| Helianthus Annuus (Sunflower) Seed Oil | 3.00 |
| Part C | |
| Preservative | 0.80 |
| Total | 100.00 |

The resulting conditioning cream was evaluated against commercially available products (containing petrochemical derivatives) for various performance characteristics in Examples 10-12.

Example 10

Wet Combing Evaluation

The primary technical function of most conditioning products is to lubricate the hair surface, and in doing so to facilitate manageability and mediate degrading feel properties. Thus, protection, conditioning, and manageability properties of a product may be evaluated through combing experiments that quantify the lubrication magnitude. Accordingly, the conditioning cream of Example 9 ("CC9") was evaluated for these properties in a wet combing study. Virgin (un-colored or unbleached) European medium brown hair test tresses (supplied by International Hair Importers) were prepared to be 1 inch wide, 8 inches long and contained 3 grams of hair.

To eliminate any structural differences in the hair, each tress was initially bleached using a 6% hydrogen peroxide solution at pH of 10.2. The tresses were left in contact with the bleach solution for 50 minutes under controlled temperature conditions (40° C.). At the end of this process, tresses were thoroughly rinsed under an Intellifaucet (Hass Mfg. Co., Averill Park, N.Y.) set at 37° C. with a flow rate of 1.0 GPM.

Internal control condition creams were selected from commercially available products that have previously been determined to represent performance extremes for different attributes. Comparative Conditioner 1 ("CC1") was a bargain brand product that previous studies have consistently shown to be a relatively poor at providing surface lubrication. Control Conditioner 2 ("CC2") was the moisturizing variant of a commercially successful hair care brand that has consistently shown high levels of surface lubrication. Each of CC1 and CC2 contains petrochemical materials.

Each tress was treated with one of the CC9, CC1 or CC2. All tress treatment was performed using an Intellifaucet set at 37° C. with a flow rate of 1.0 GPM. Tresses were first wetted for 30 seconds. Conditioner was syringe-applied to the hair at a dosage of 15% of the tress weight (i.e., 0.45 g product on a 3 gram tress). The product was massaged into the tress for 30 seconds, and then allowed to remain on the hair for additional 30 seconds. The product was then rinsed under the Intellifaucet for 30 seconds. A negative control consisting of a tress that was not treated with any conditioning cream was also evaluated.

Each tress was subjected to a wet combing evaluating performed in accordance with the widely used method first proposed by Garcia & Diaz (JSCC, 27, (1976) 379-398-Combability Measurements on Hair) the contents of which are incorporated here in by reference. Wet combing experiments were performed using an Instron 5500 series tensile tester equipped with Bluehill software. Eight replicate hair tresses are used for each sample to ensure statistical relevance.

Figure 11:
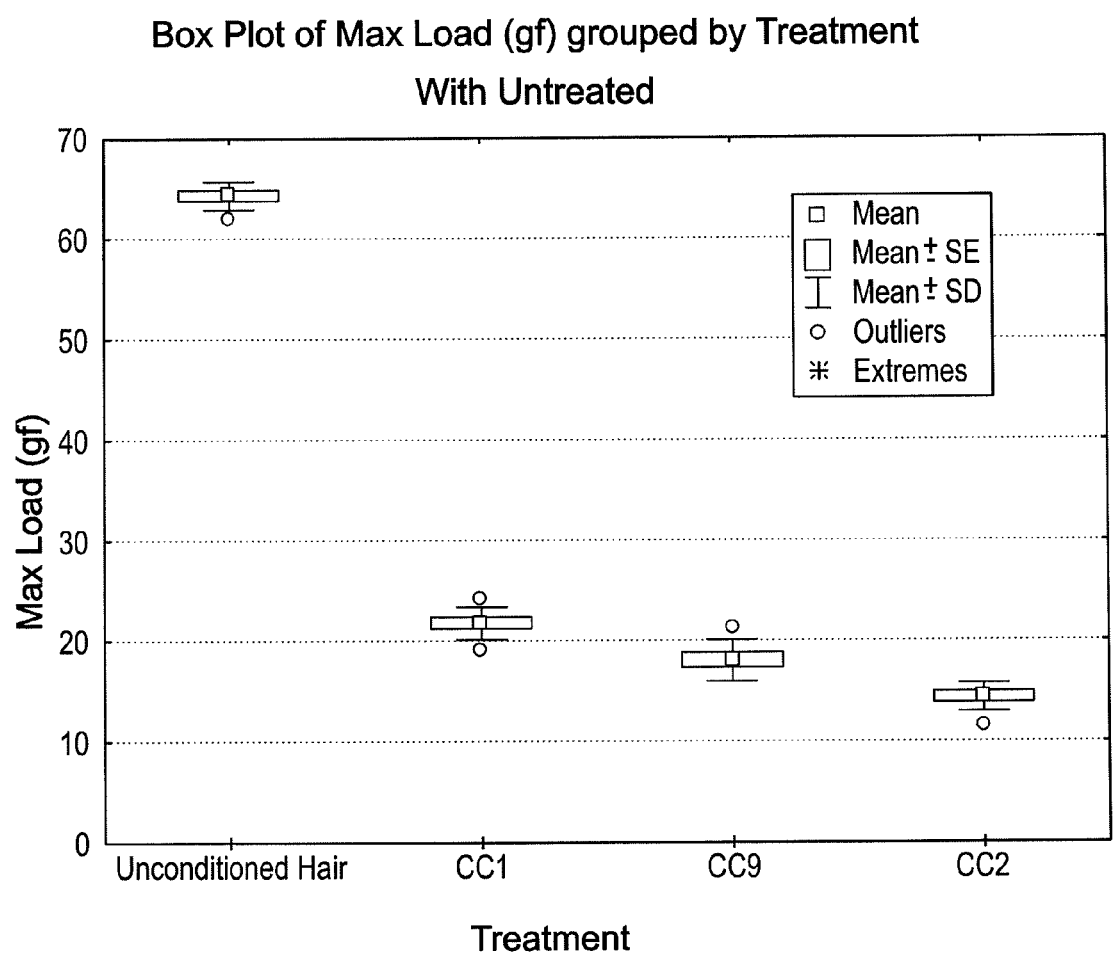
FIG. 11 is a graphical representation of the wet combing evaluations of untreated hair and hair treated with the inventive compositions and two commercially available, non-natural compositions.

The results of the wet combing evaluations are shown below, and are plotted graphically in FIG. 11.

| Results of Wet Combing Evaluation | | | | | |
|---|---|---|---|---|---|
| Treatment | N | Mean | Std Dev | Std Err Mean | |
| Unconditioned Hair | 8 | 64.3 | 1.40 | 0.50 | A |
| CC1 | 8 | 21.7 | 1.61 | 0.57 | B |
| CC9 | 8 | 18.0 | 2.06 | 0.73 | C |
| CC2 | 8 | 14.3 | 1.41 | 0.50 | D |

Levels not connected by same letter are significantly different.

As can be seen from the results, Conditioner of Example 9 (CC9) has properties about intermediate relative to the properties of the two commercial control formulations. Thus, CC9 provides a wet combing performance that is comparable to many commercially available bodifying/volumizing conditioners.

Example 11

Figure 12:
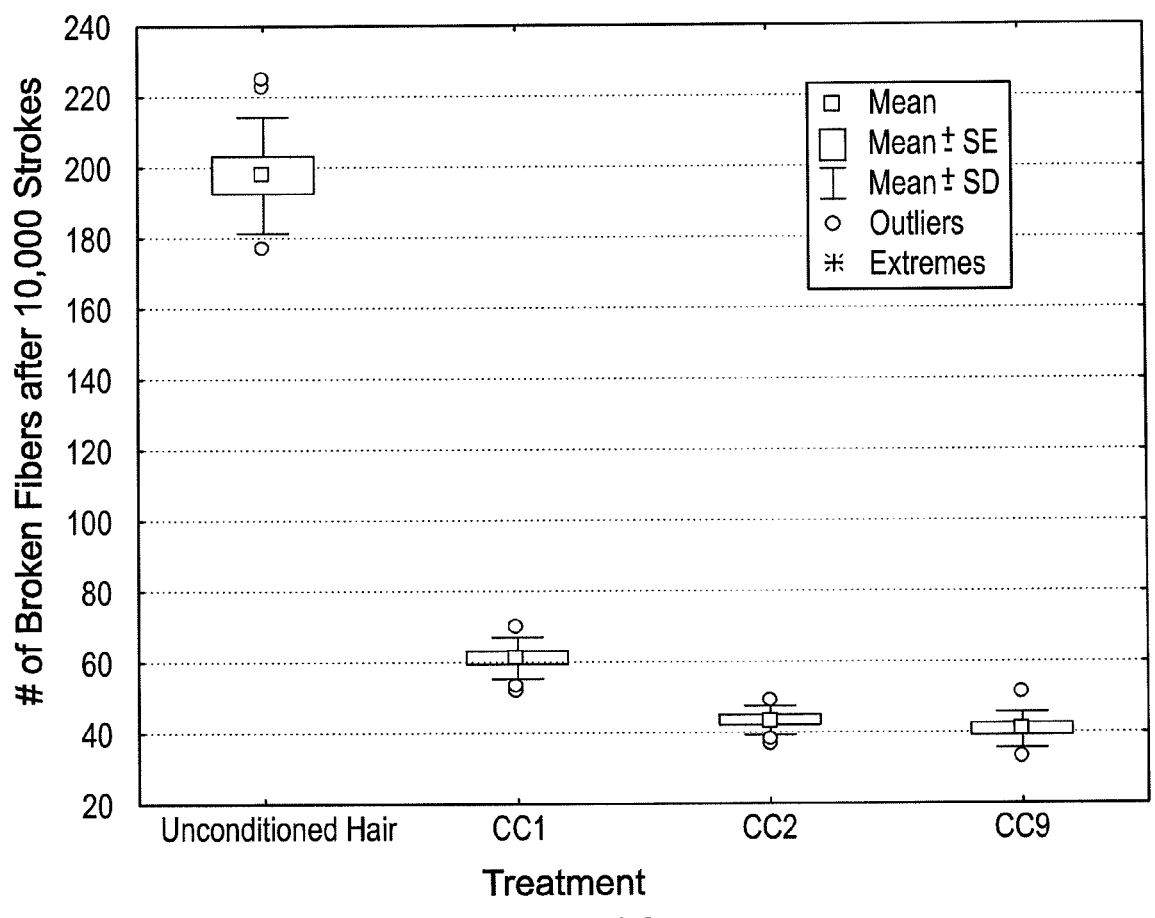
FIG. 12 is a graphical representation of data obtained from brushing experiments of human hair treated with a conditioner of the invention and comparative conditioners.

CC9 was evaluated for its surface lubrication properties. Repeated brushing experiments provide a means to evaluate a conditioning products' ability to provide surface lubrication, therefore reducing hair snags, entanglements and abrasion which in turn reduces fiber (hair) breakage. The results of such tests are expressed as a count of the number of broken fibers as a function of combing/brushing cycles. Tresses were bleached and treated with CC9, CC1 and CC2 as described in Example 10, above. Each tress was brushed 10,000 times with subsequent counting of broken fibers. Brushing was performed using a repeated combing/brushing device, to ensure uniform application of brushing force across all tress samples. Eight replicate tresses were used. The results are shown below and are plotted graphically in FIG. 12.

| Treatment | N | Mean | Std Dev | Std Err Mean | |
|---|---|---|---|---|---|
| Unconditioned Hair | 10 | 197.9 | 16.46 | 5.21 | A |
| CC1 | 10 | 61.3 | 5.87 | 1.86 | B |
| CC2 | 10 | 43.5 | 4.09 | 1.29 | C |
| CC9 | 10 | 40.7 | 5.03 | 1.59 | C |

Levels not connected by same letter are significantly different

The data demonstrate that CC9 protects against breakage at a level comparable to the positive control (CC2). Results suggest an approximate 80% reduction in the amount of breakage relative to Unconditioned Hair.

Example 12

CC9 was evaluated for its ability to reduce static electricity build up in hair. Under low humidity conditions, hair has an especially low conductivity and so charges resulting from standard grooming practices (such as heat styling and brushing) are not readily dissipated. Many conditioner products aim to reduce static electricity build-up, although the mechanism by which charge is reduces has not yet been definitively elucidated. It appears likely that there is a contribution from lubrication (which reduces the amount of charge build up), and also an increased surface conductivity arising from the deposition of cationic surfactants (which facilitates charge dissipation).

Figure 13:
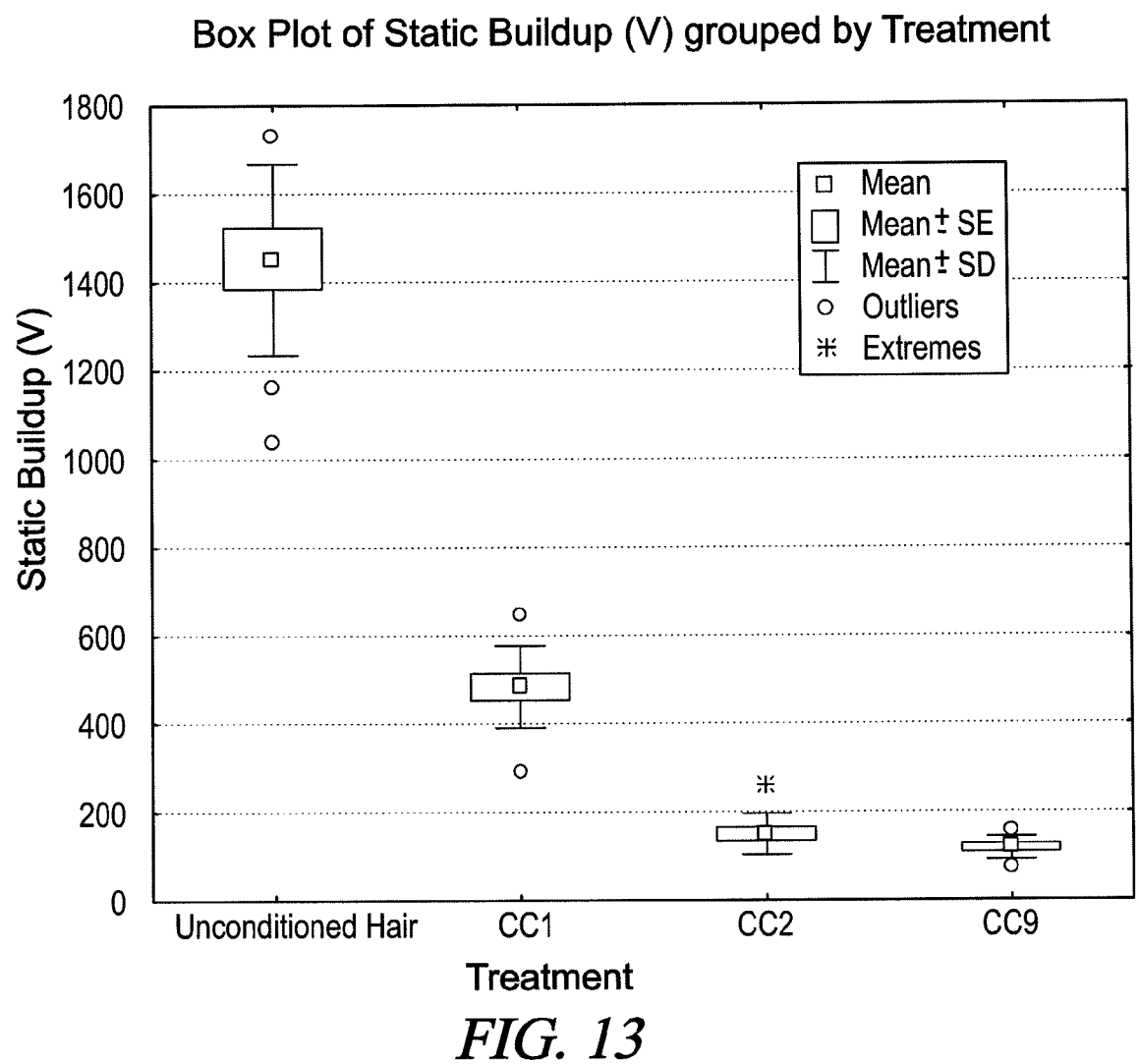
FIG. 13 is a graphical representation of data obtained from static electricity evaluation of human hair, untreated and treated with the inventive compositions and two commercially available, non-natural compositions.
Figure 16:
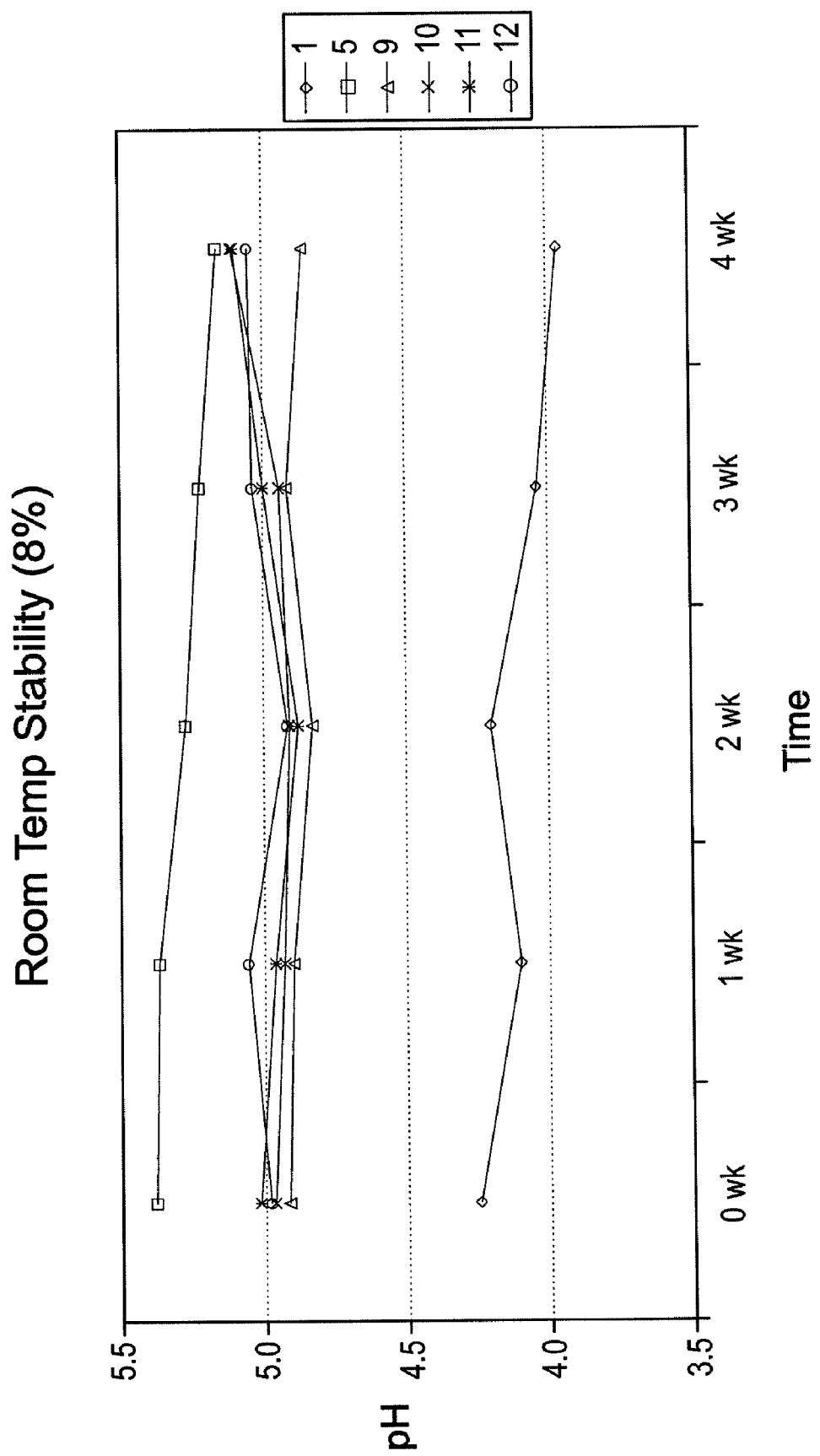
FIGS. 16-23 are graphical representations of the pH changes over time of the formulations of FIG. 14 as evaluated at room temperature.
Figure 17:
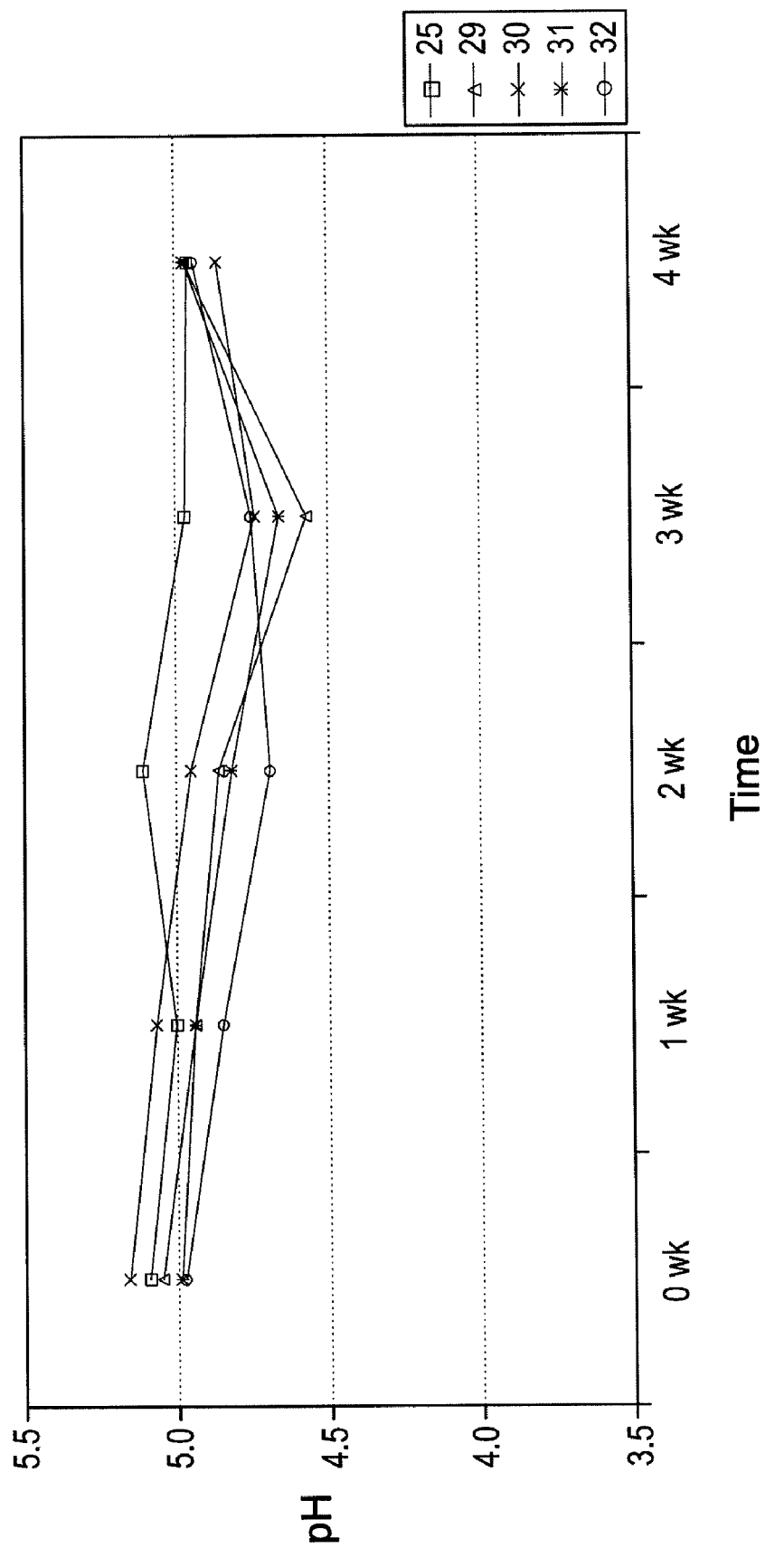
Figure 18:
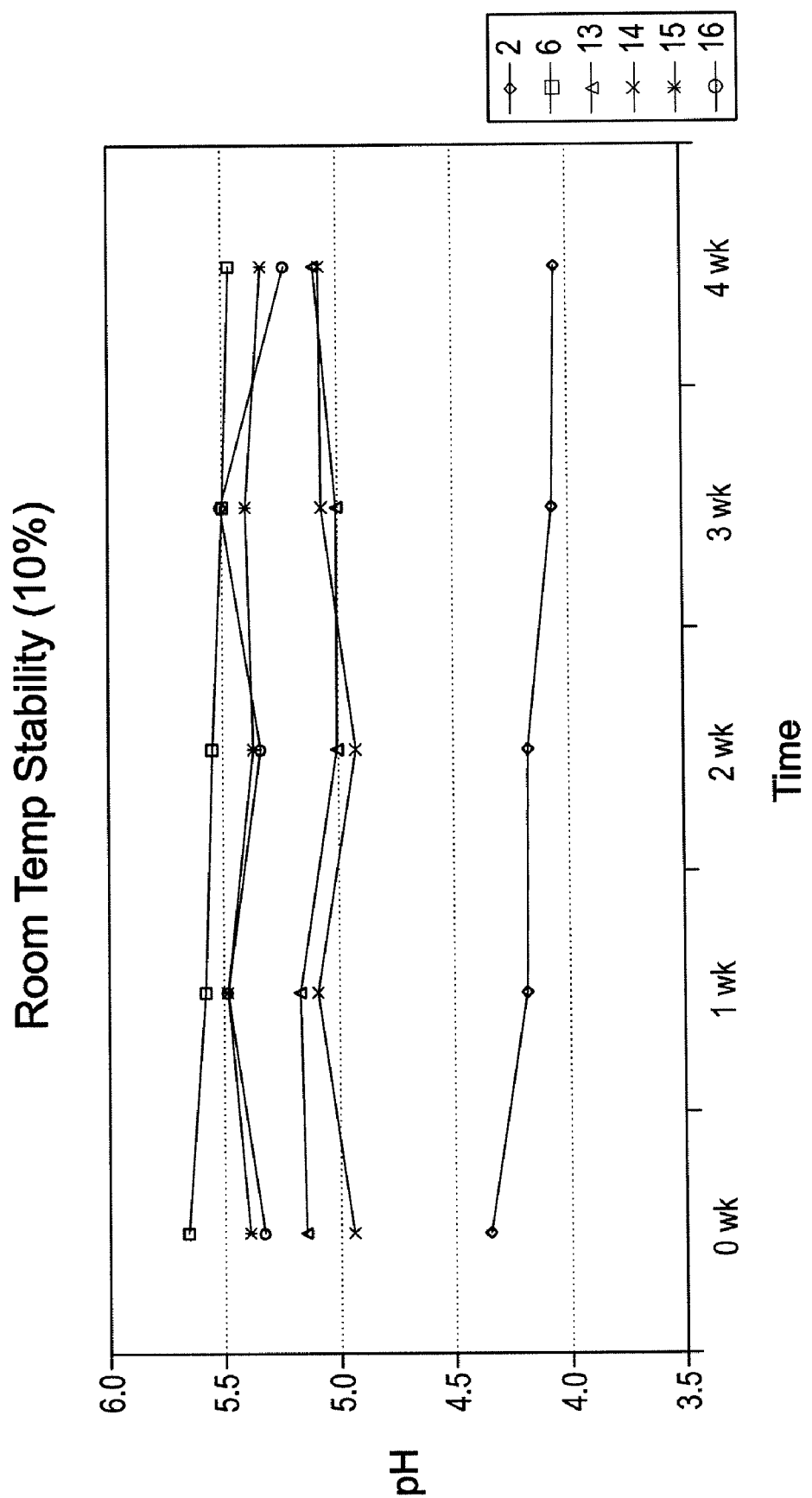
Figure 19:
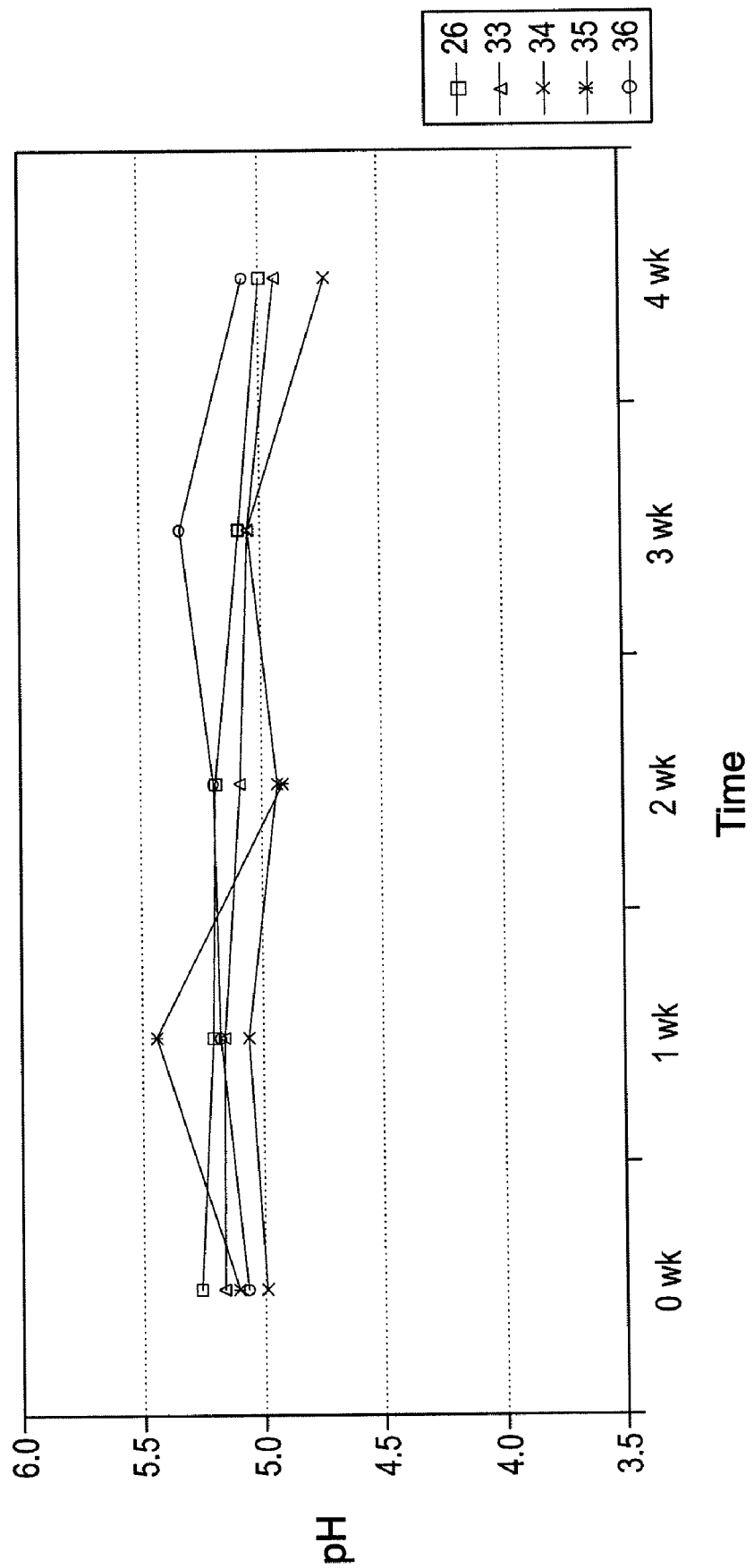
Figure 20:
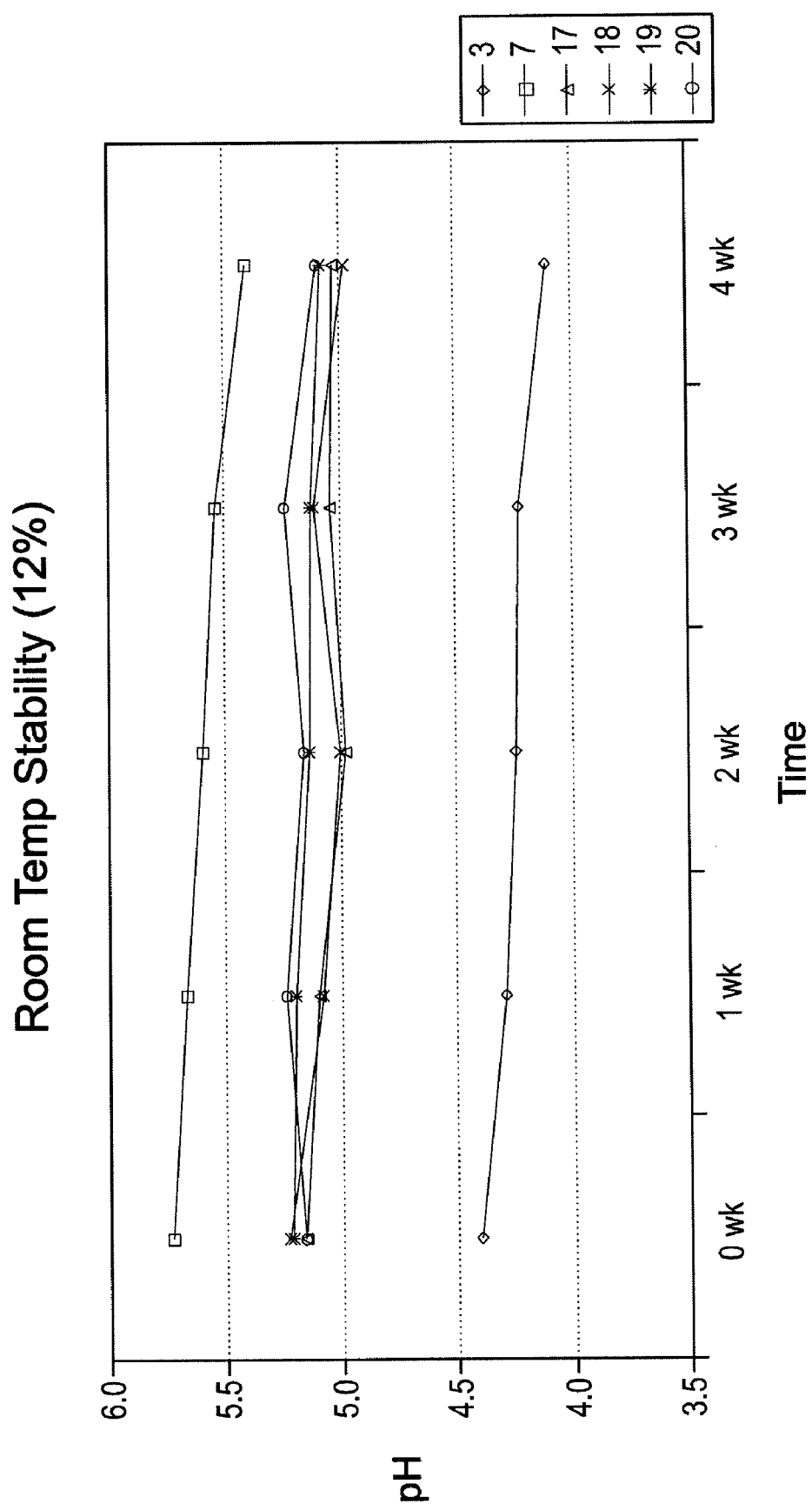
Figure 21:
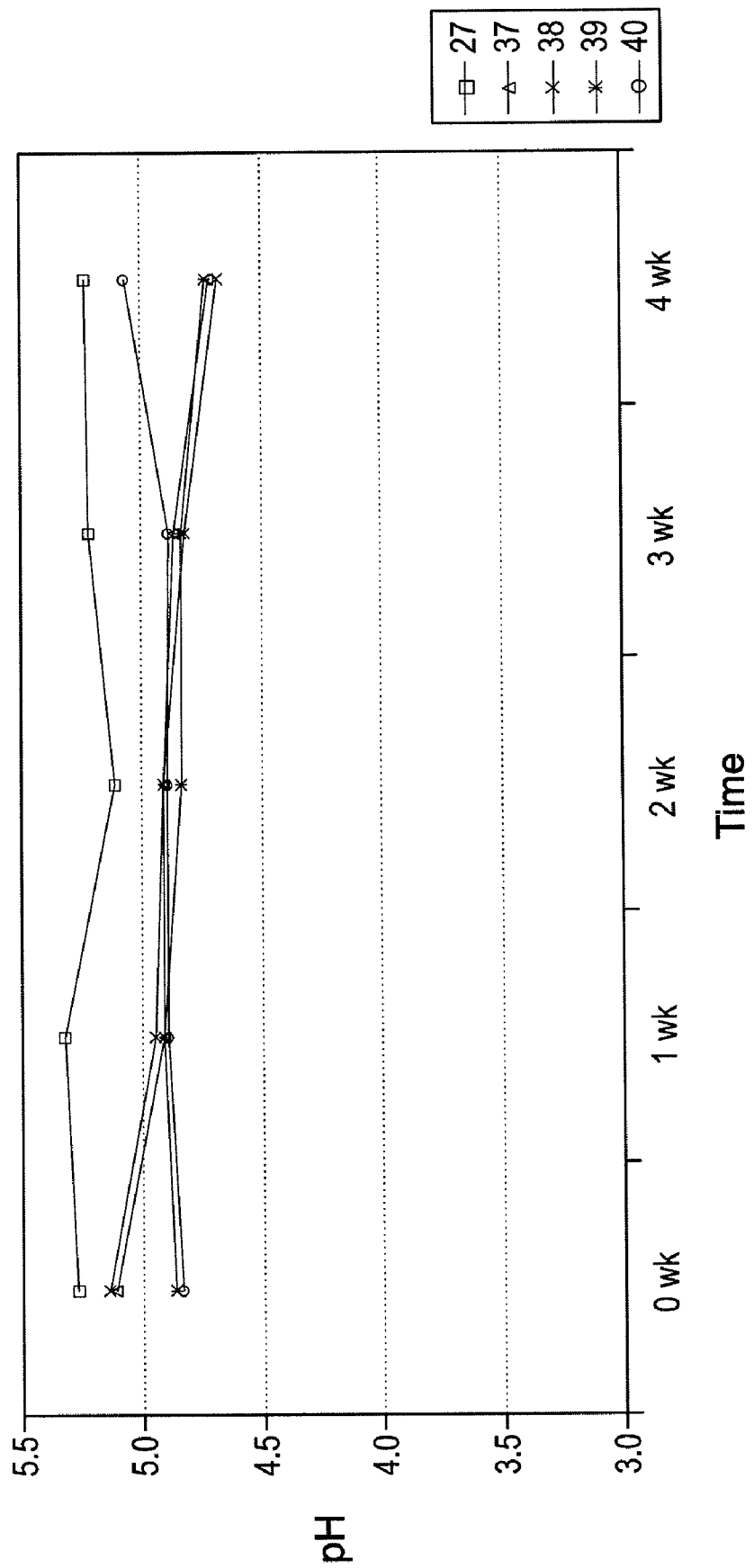
Figure 22:
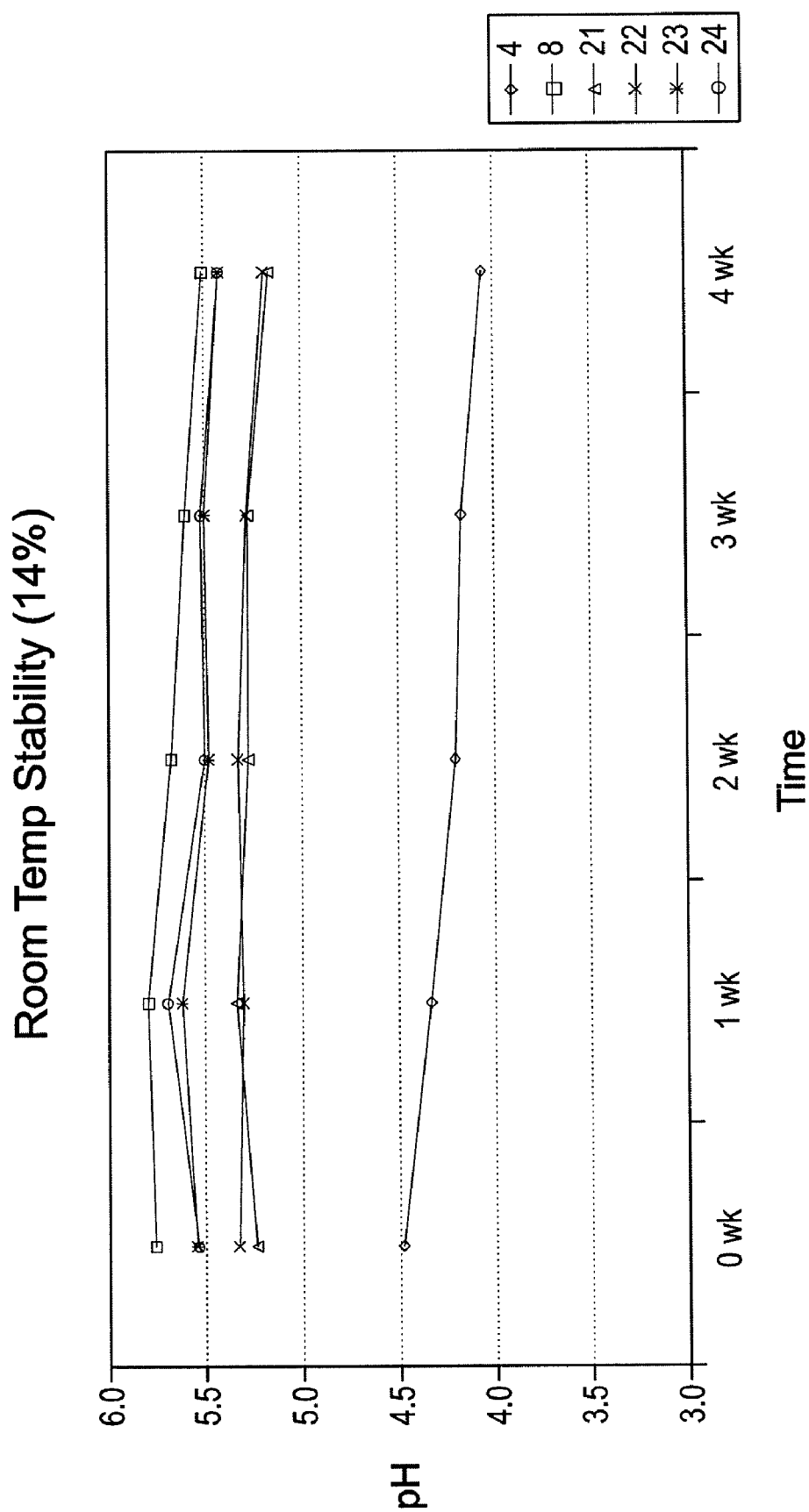
Figure 23:
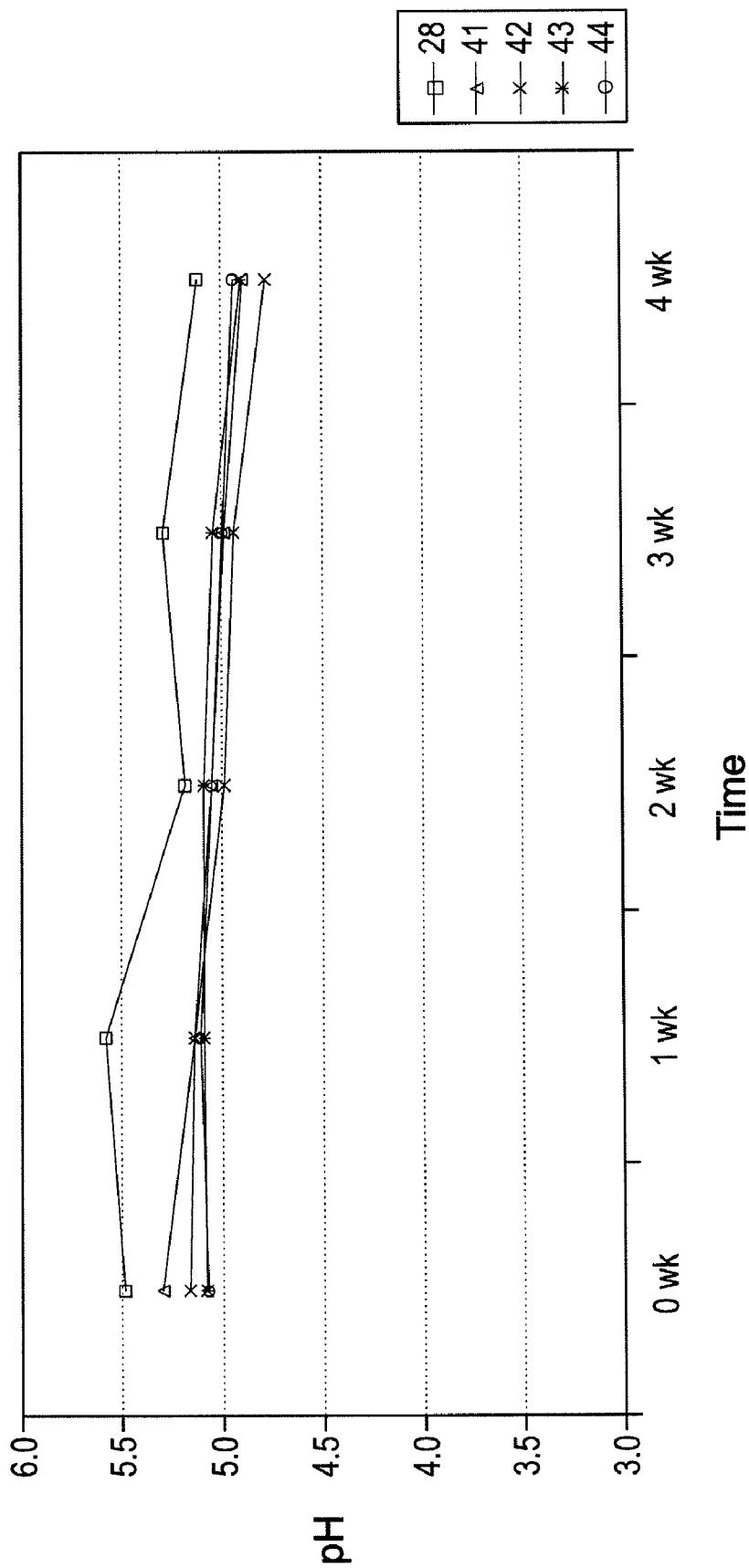
Figure 24:
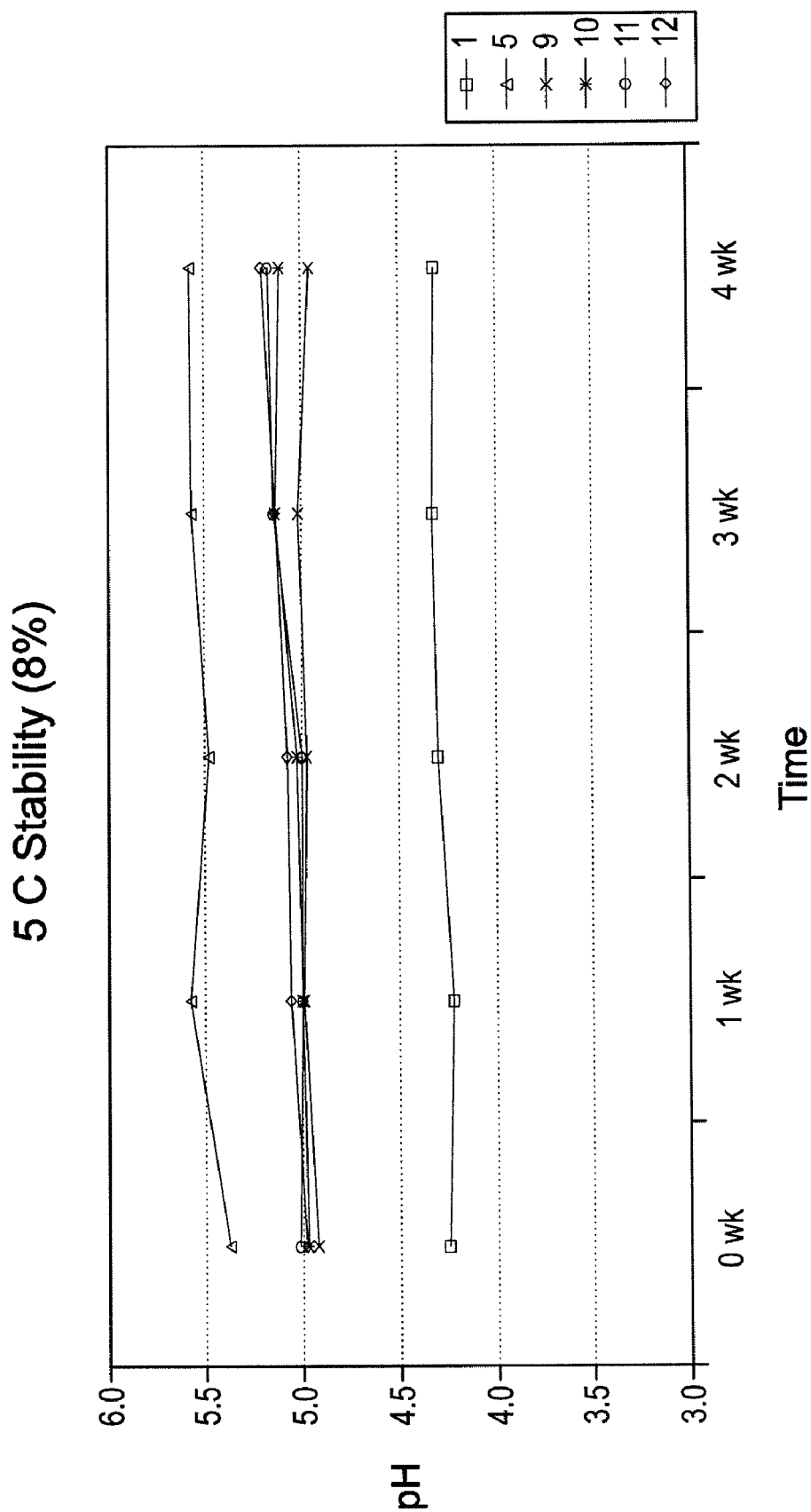
FIGS. 24-31 are graphical representations of the pH changes over time of the formulations of FIG. 14 as evaluated at 5° C.
Figure 25:
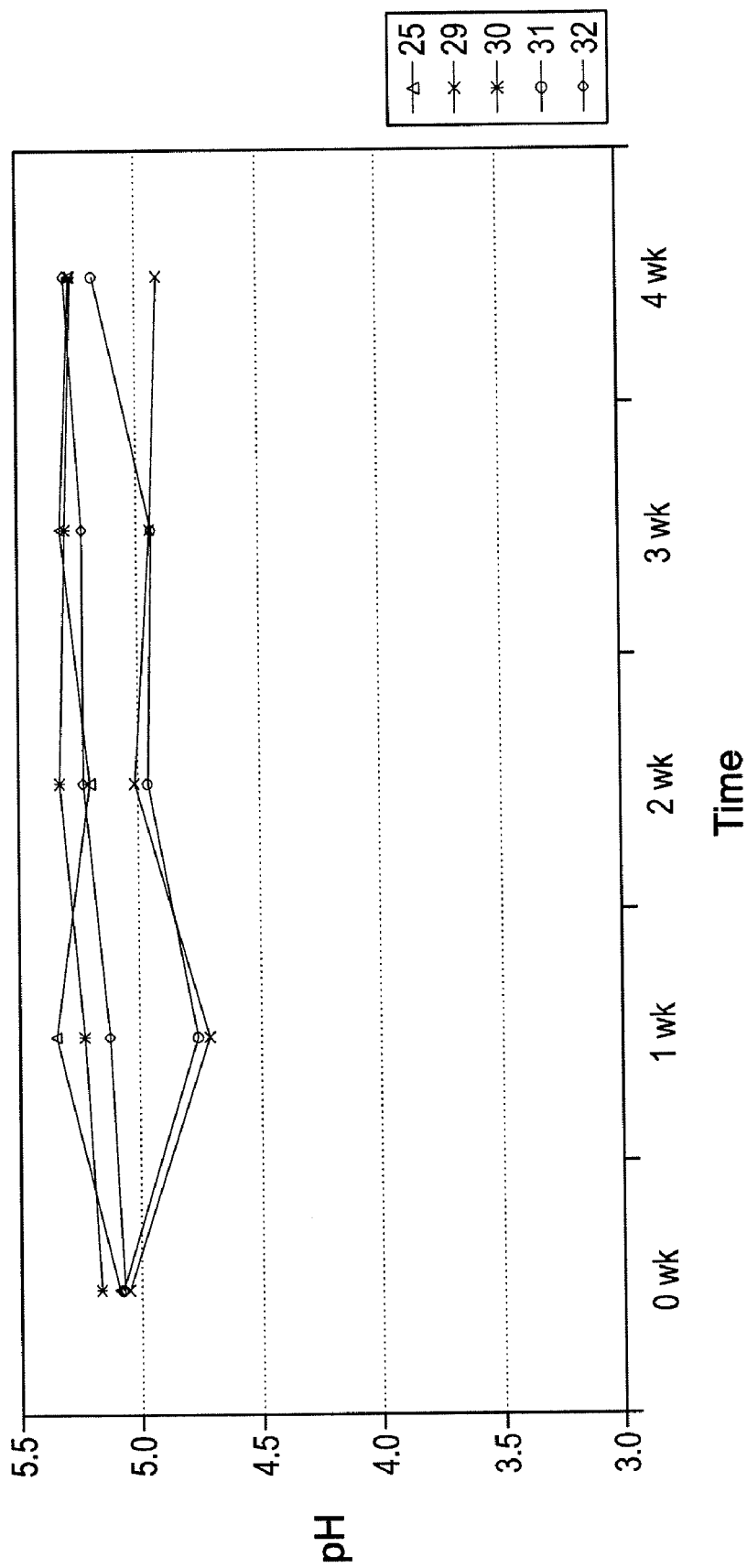
Figure 26:
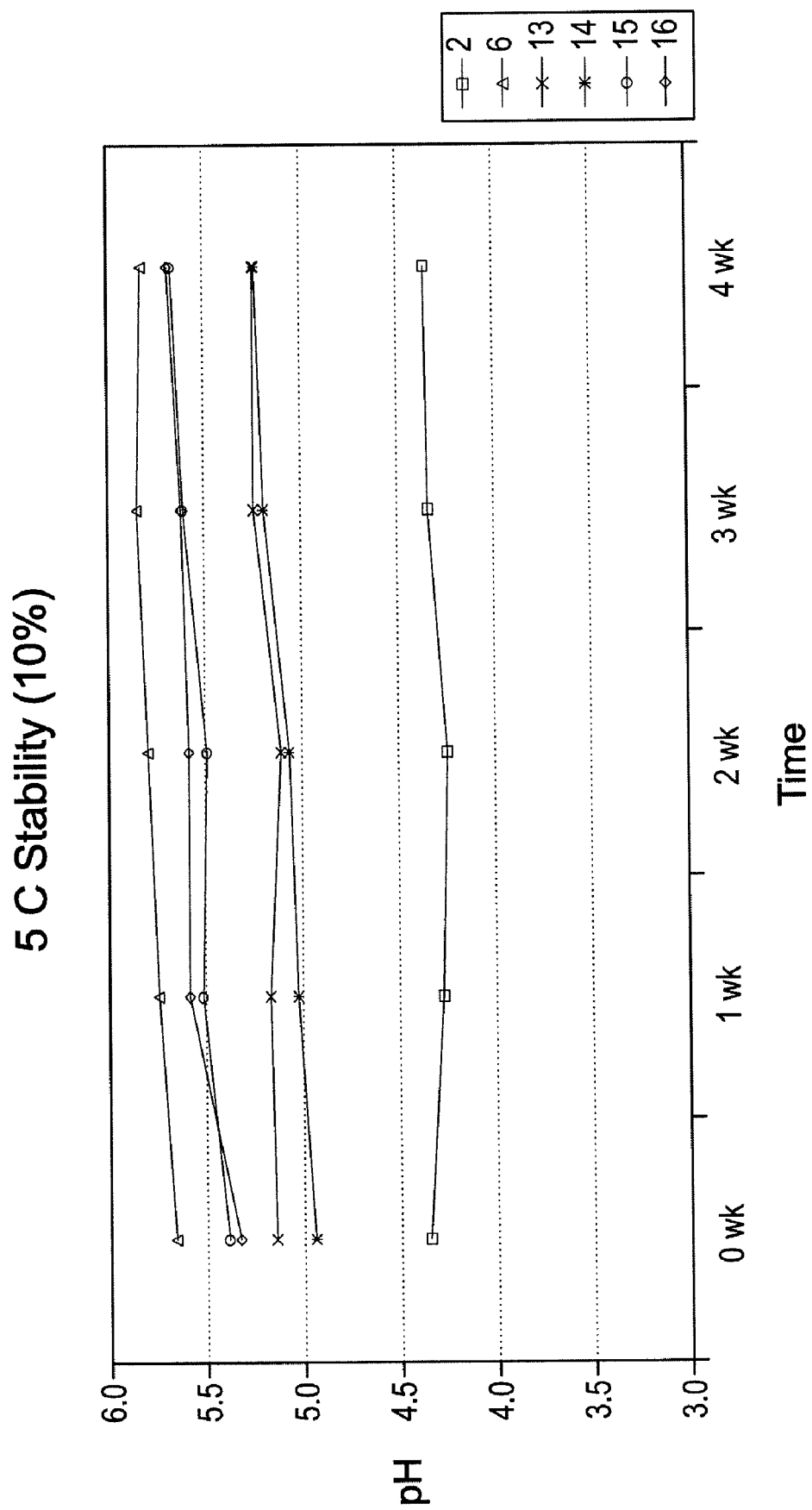
Figure 27:
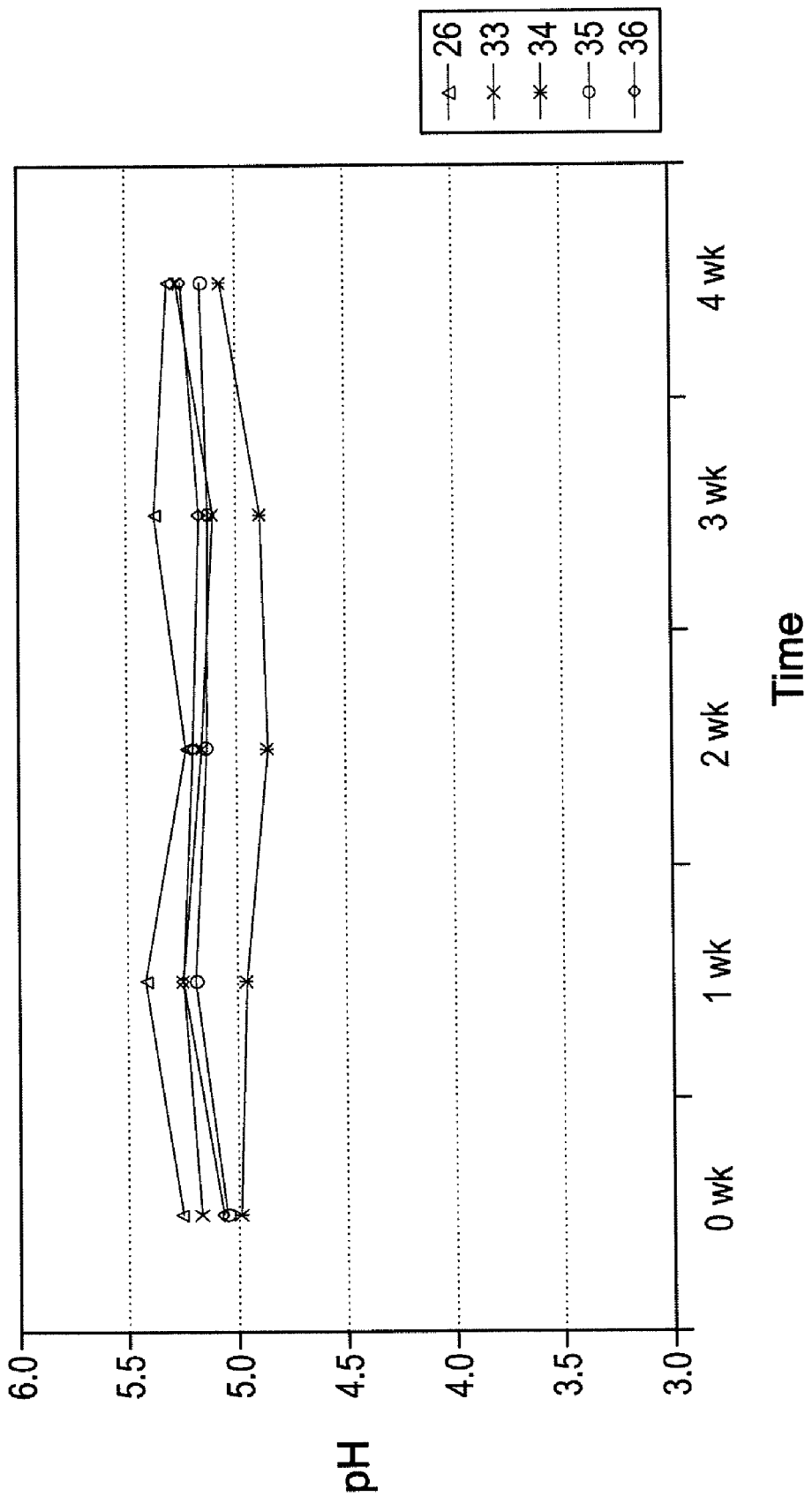
Figure 28:
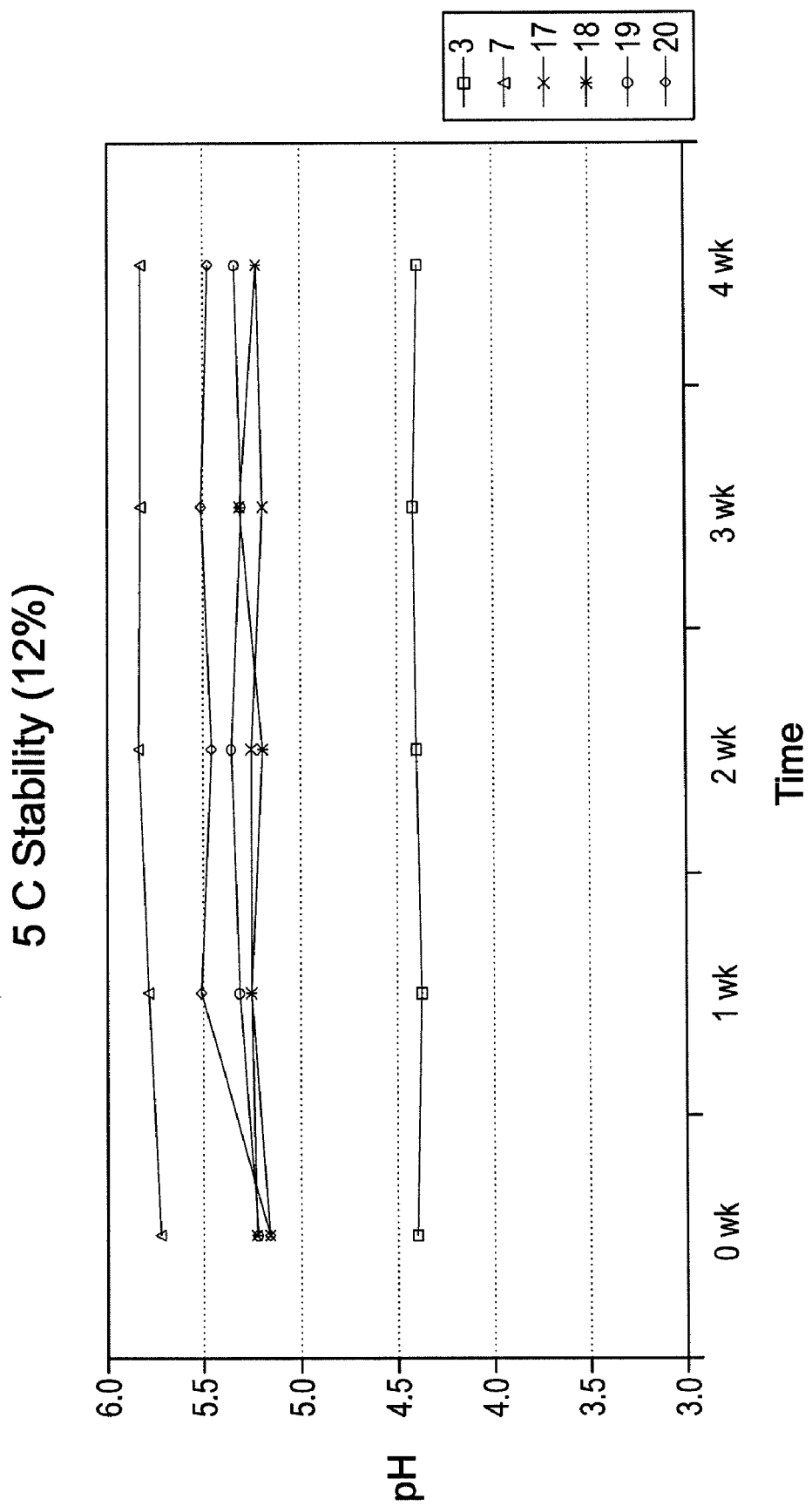
Figure 29:
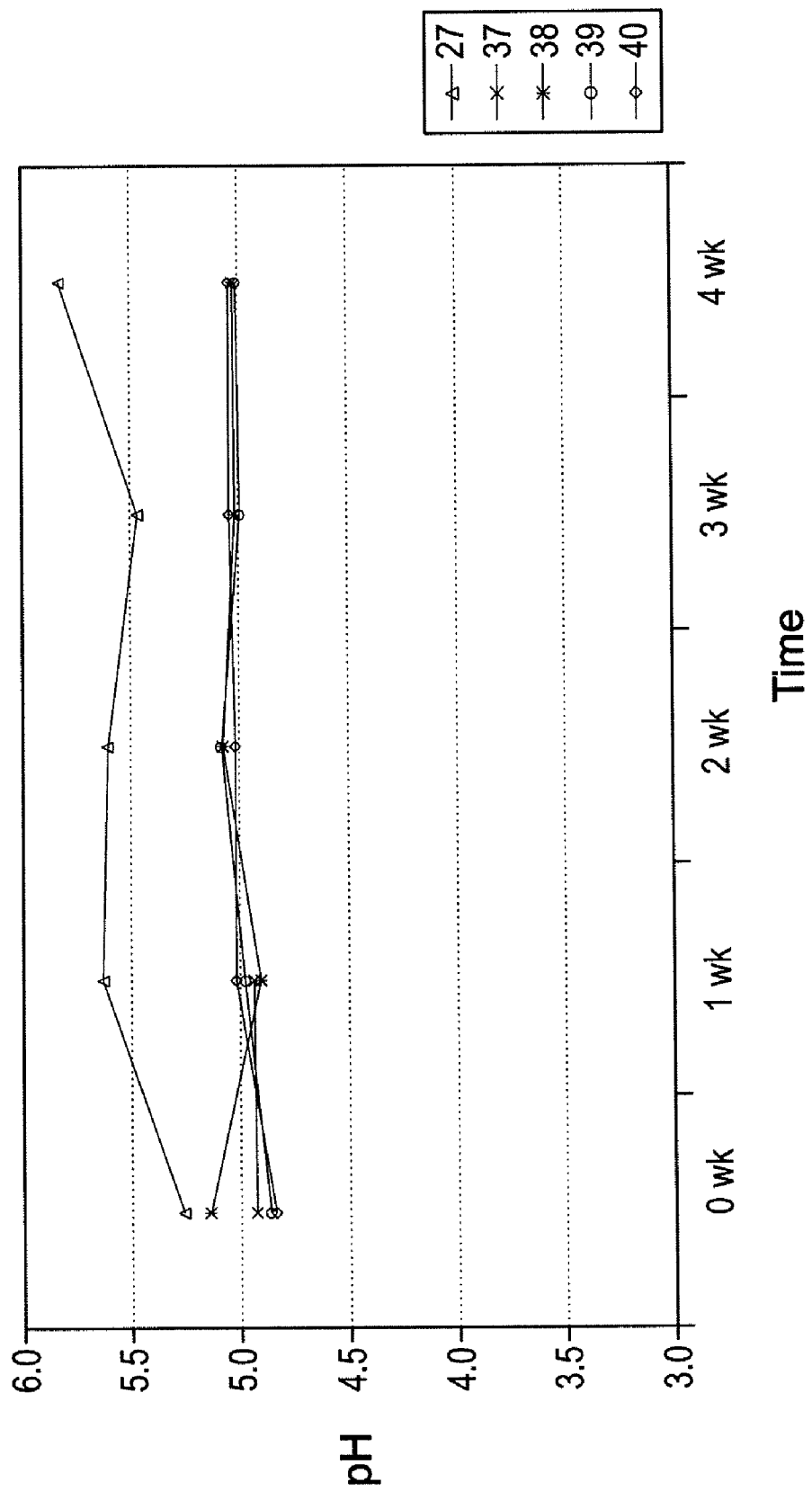
Figure 30:
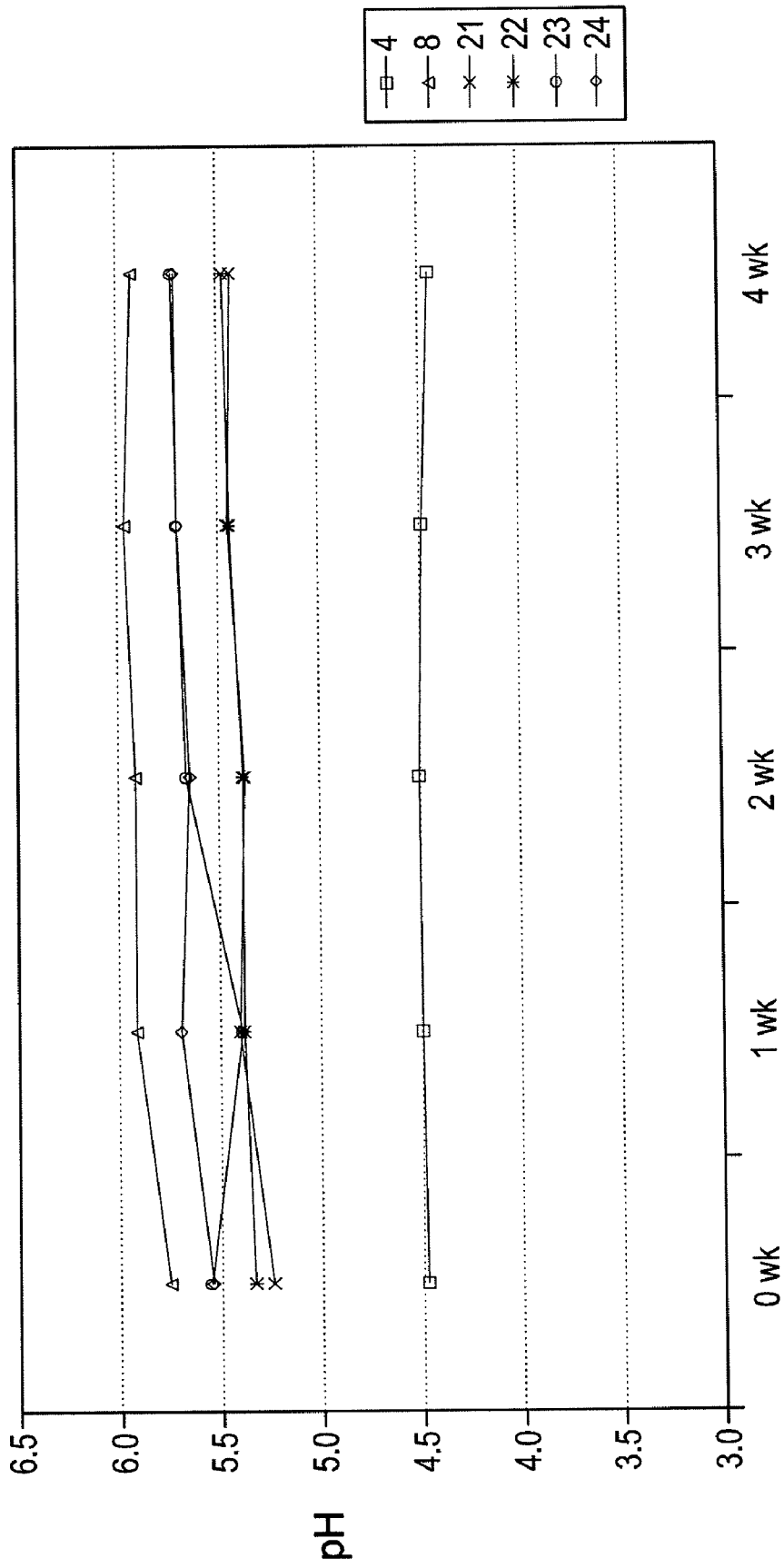
Figure 31:
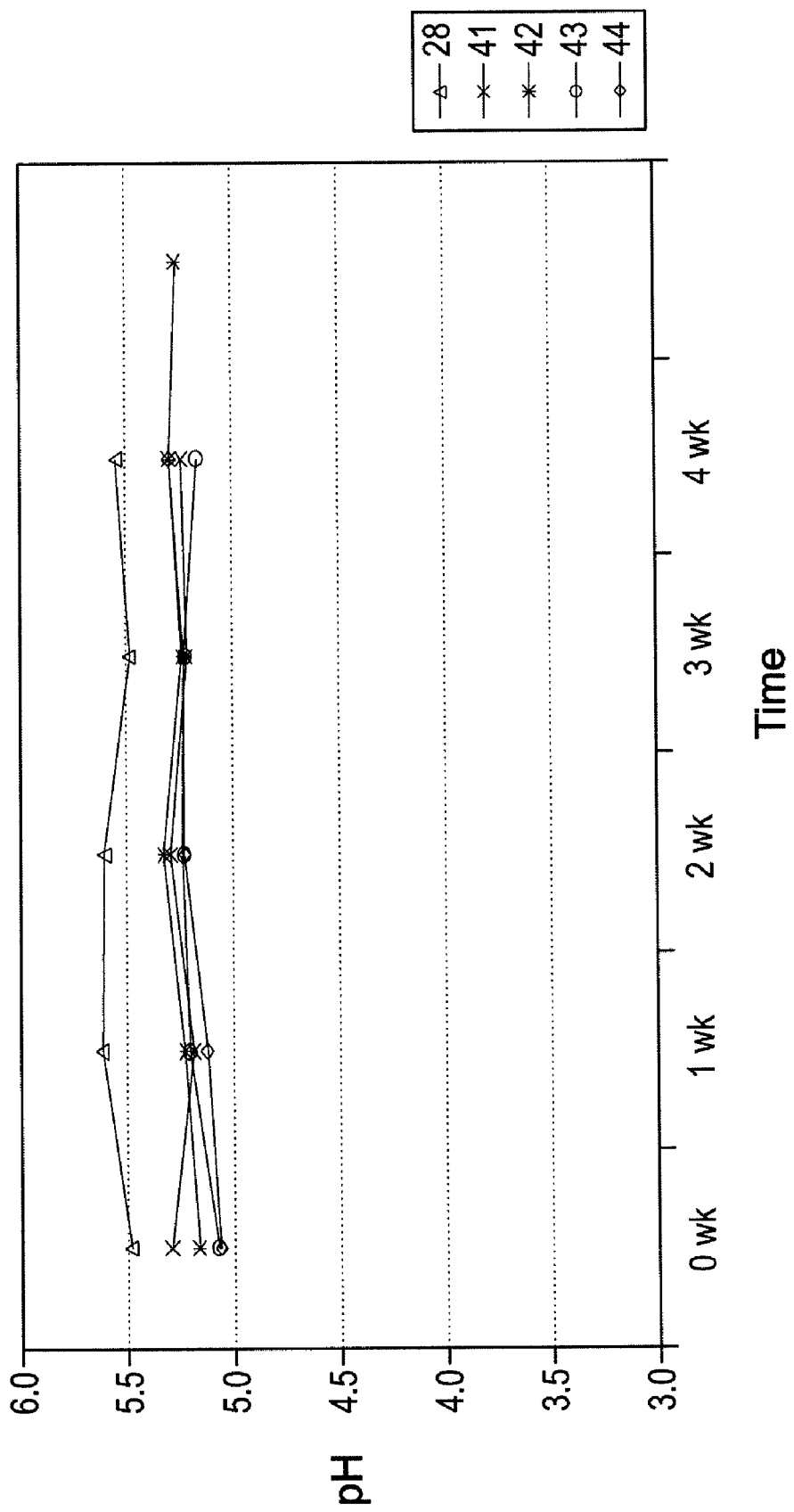
Figure 32:
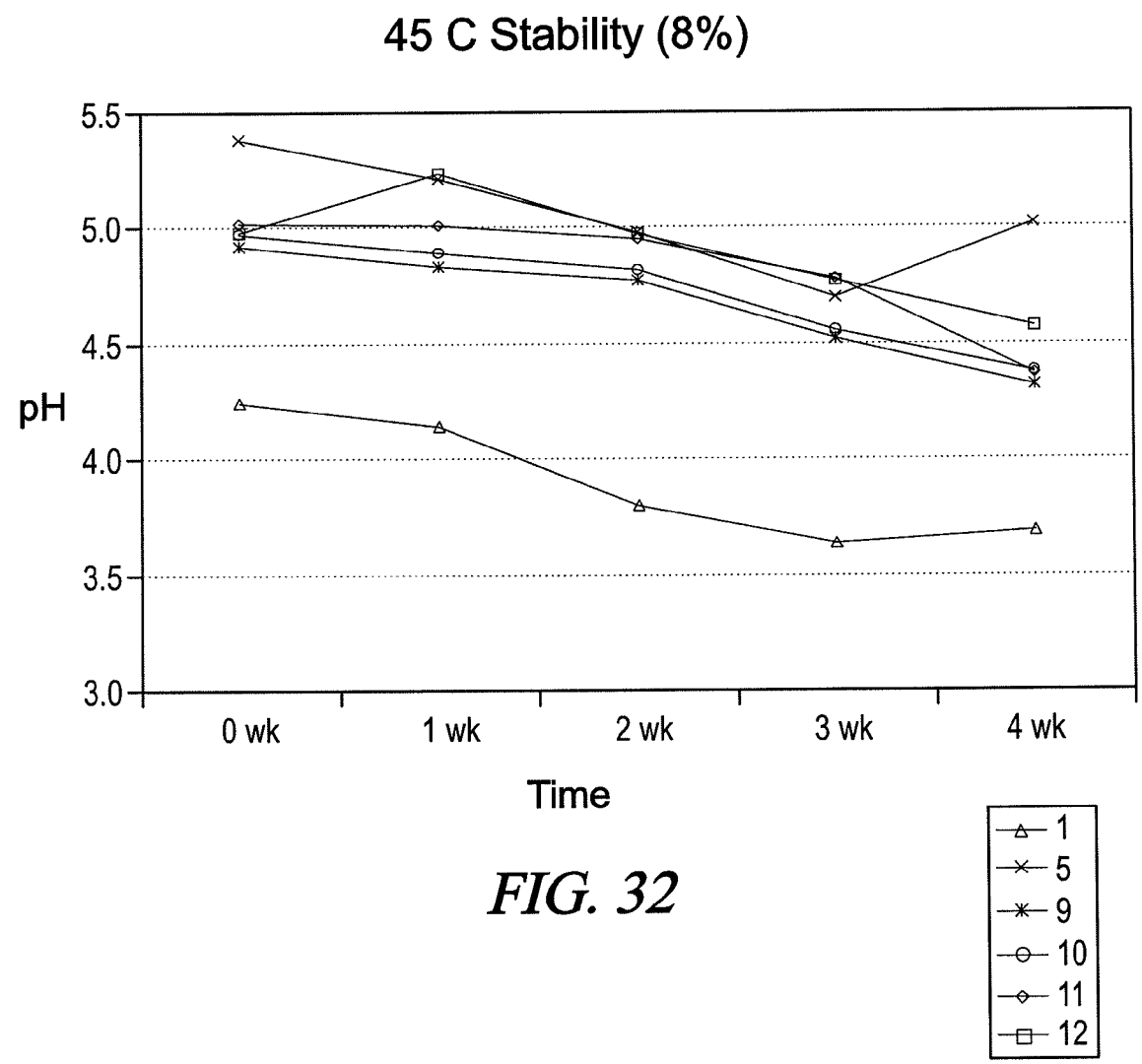
FIGS. 32-39 are graphical representations of the pH changes over time of the formulations of FIG. 14 as evaluated at 45° C.
Figure 33:
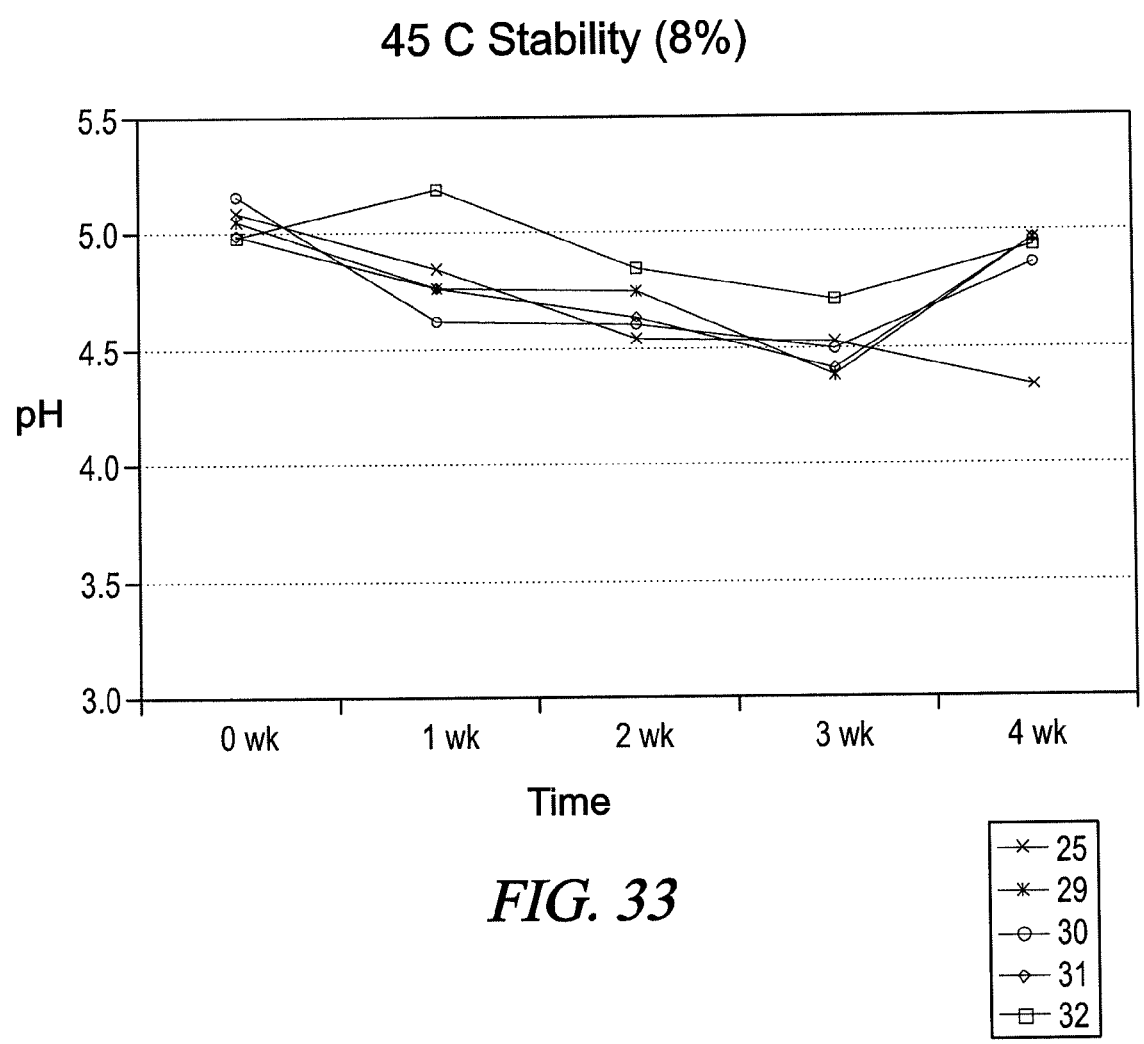
Figure 34:
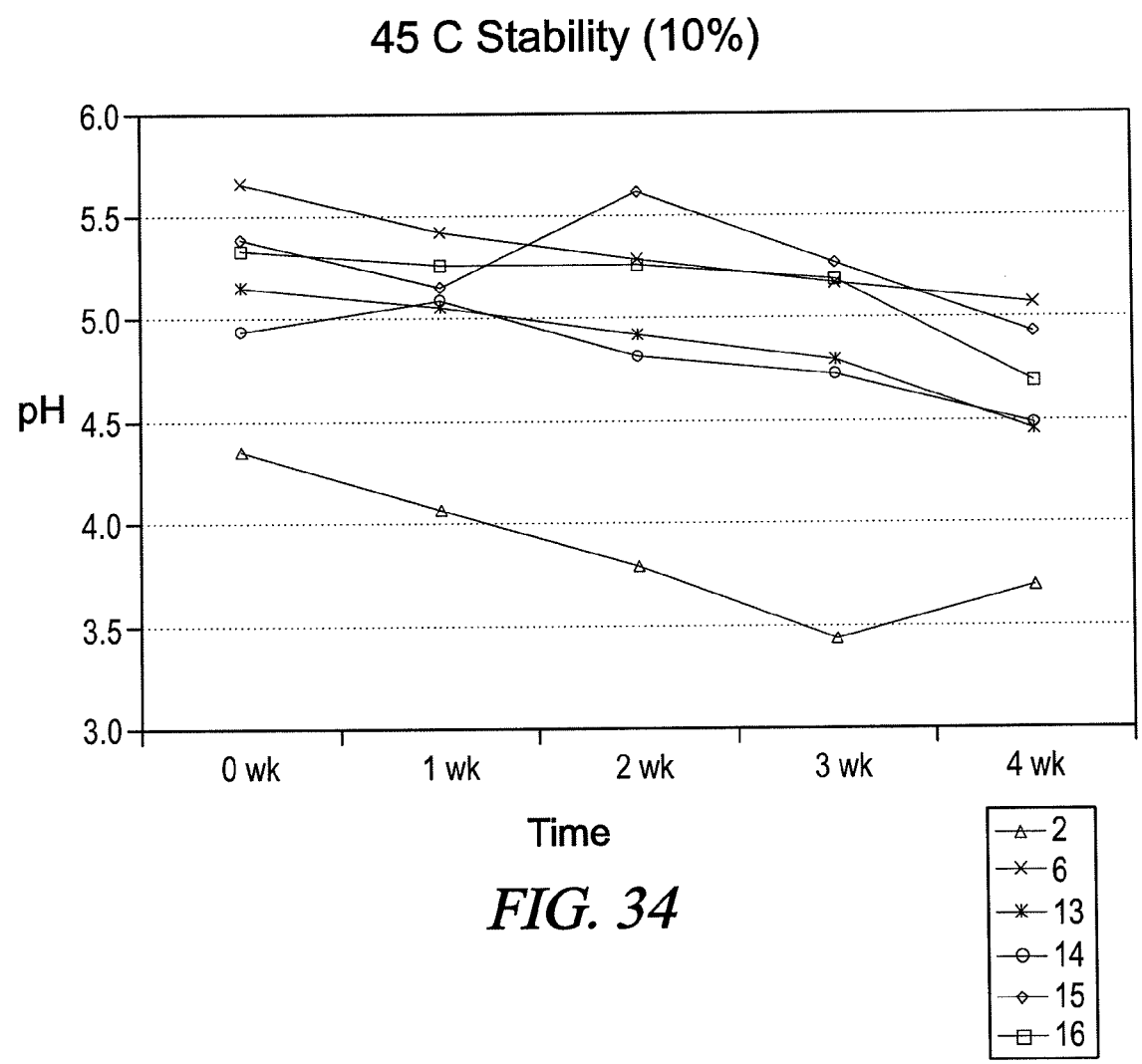
Figure 35:
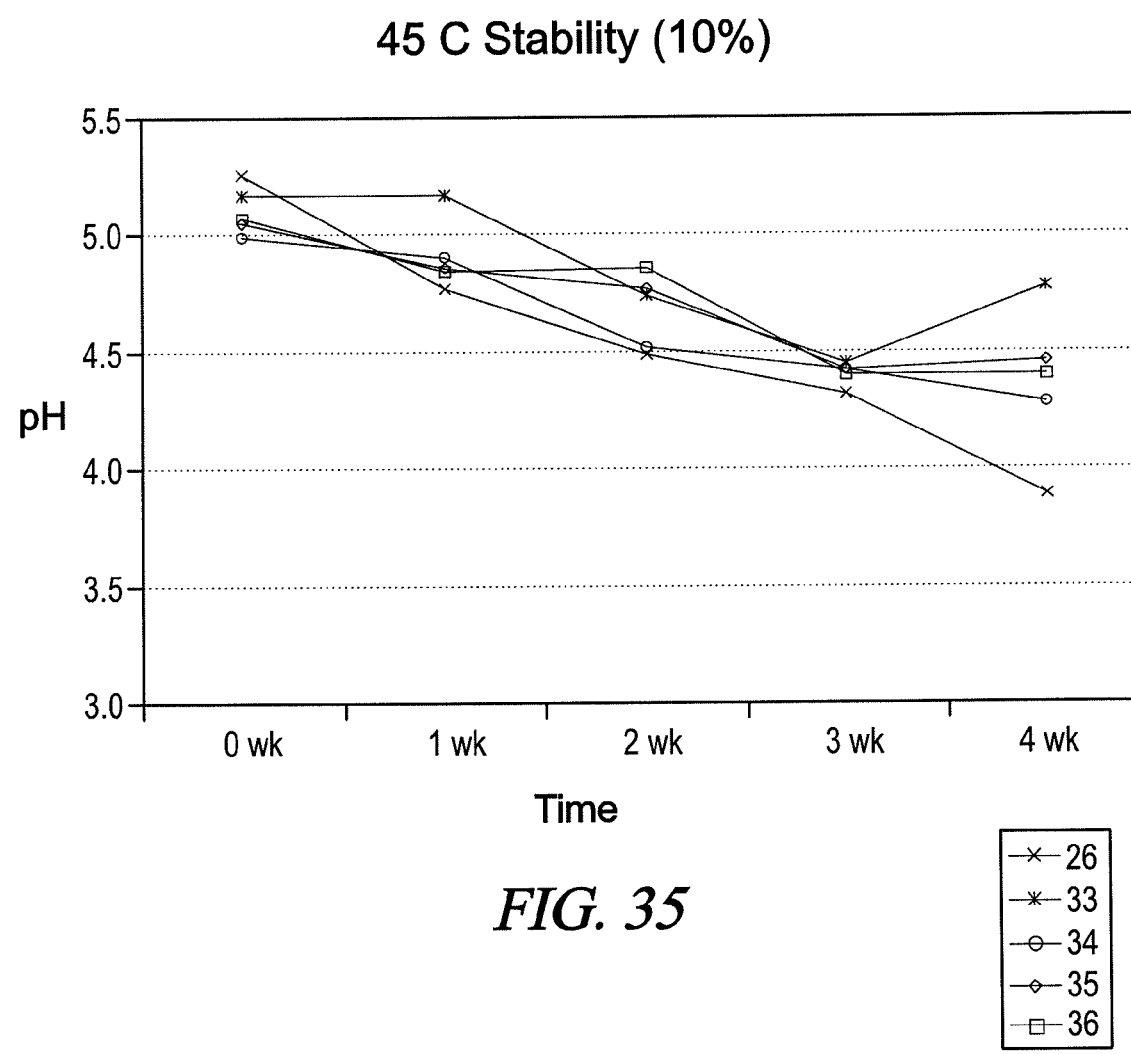
Figure 36:
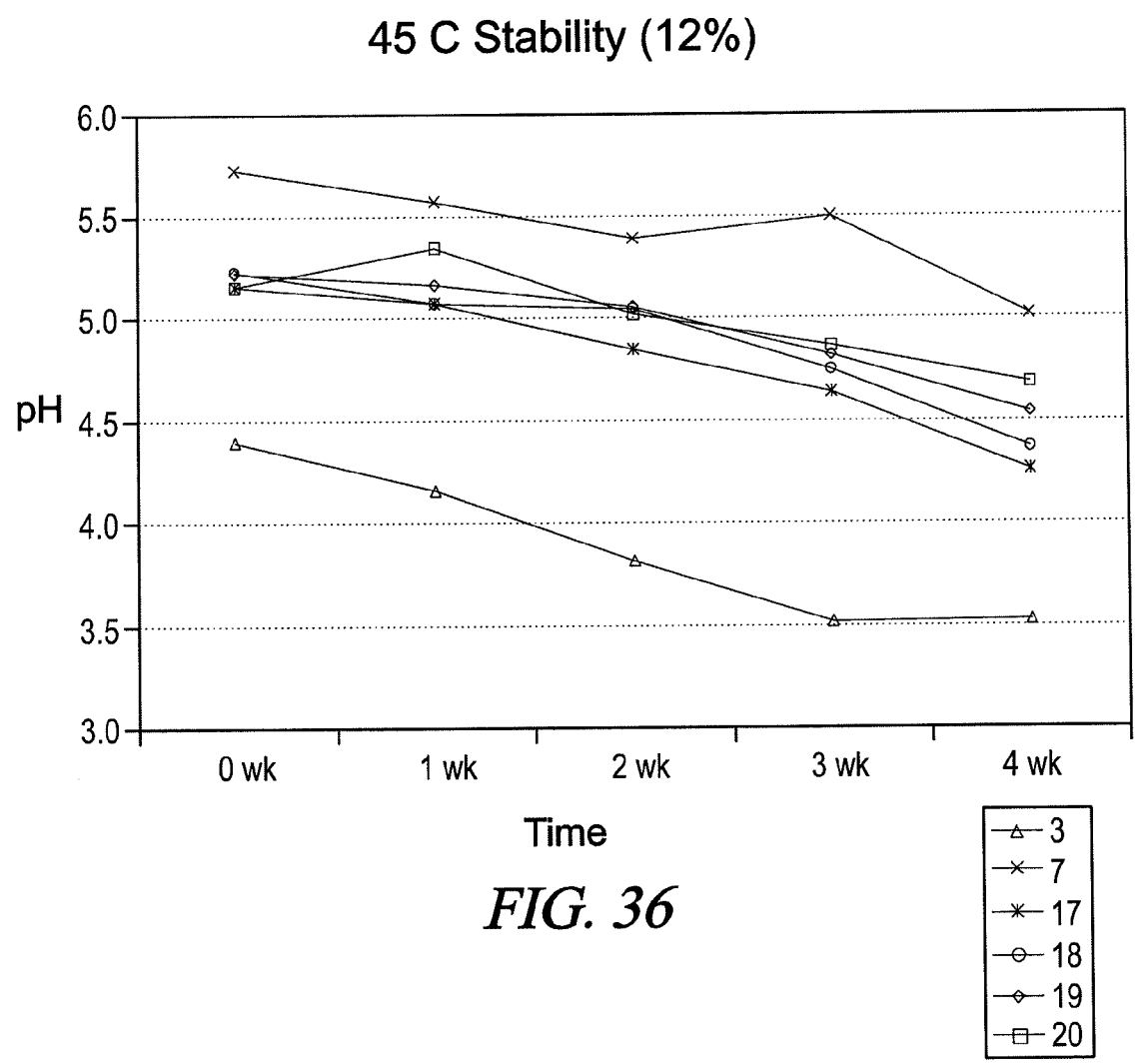
Figure 37:
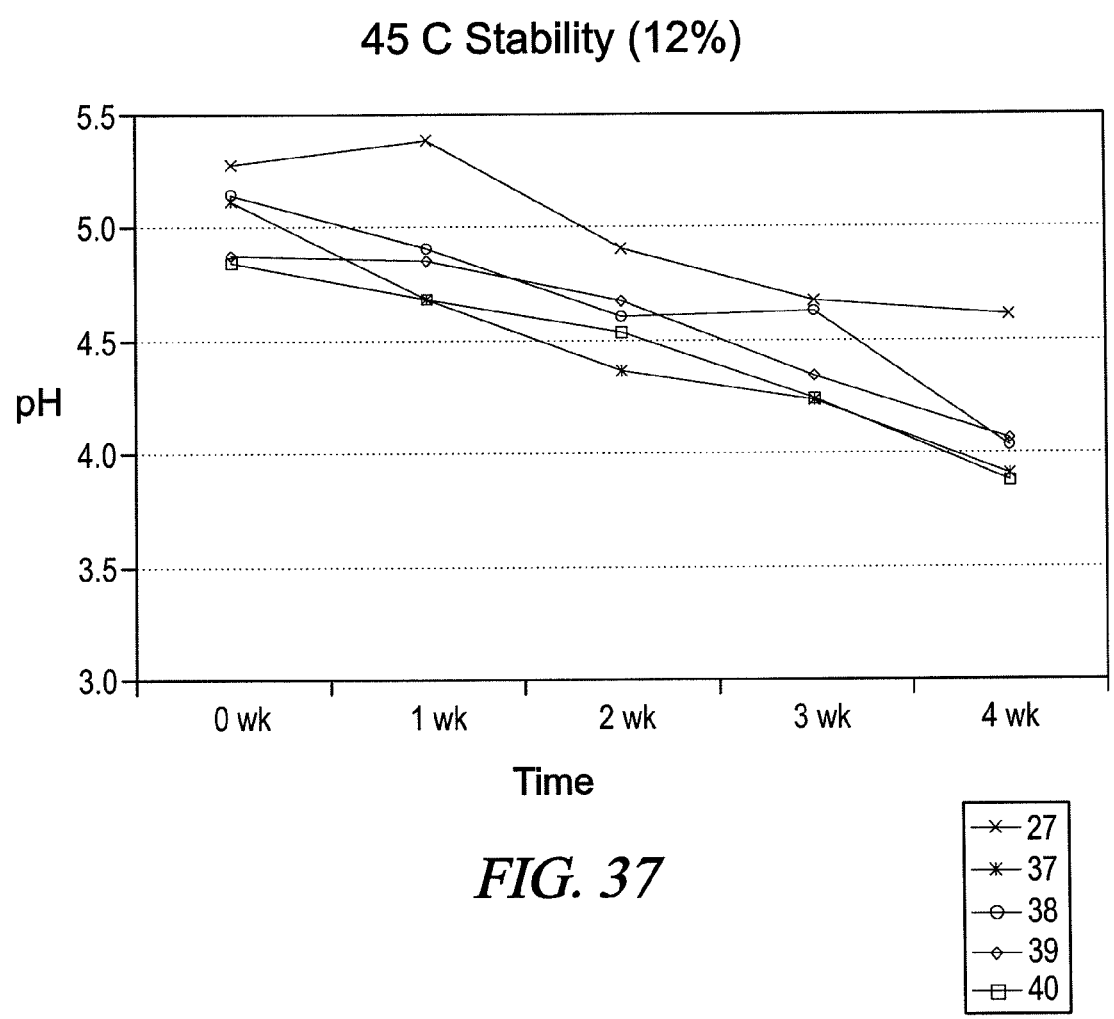
Figure 38:
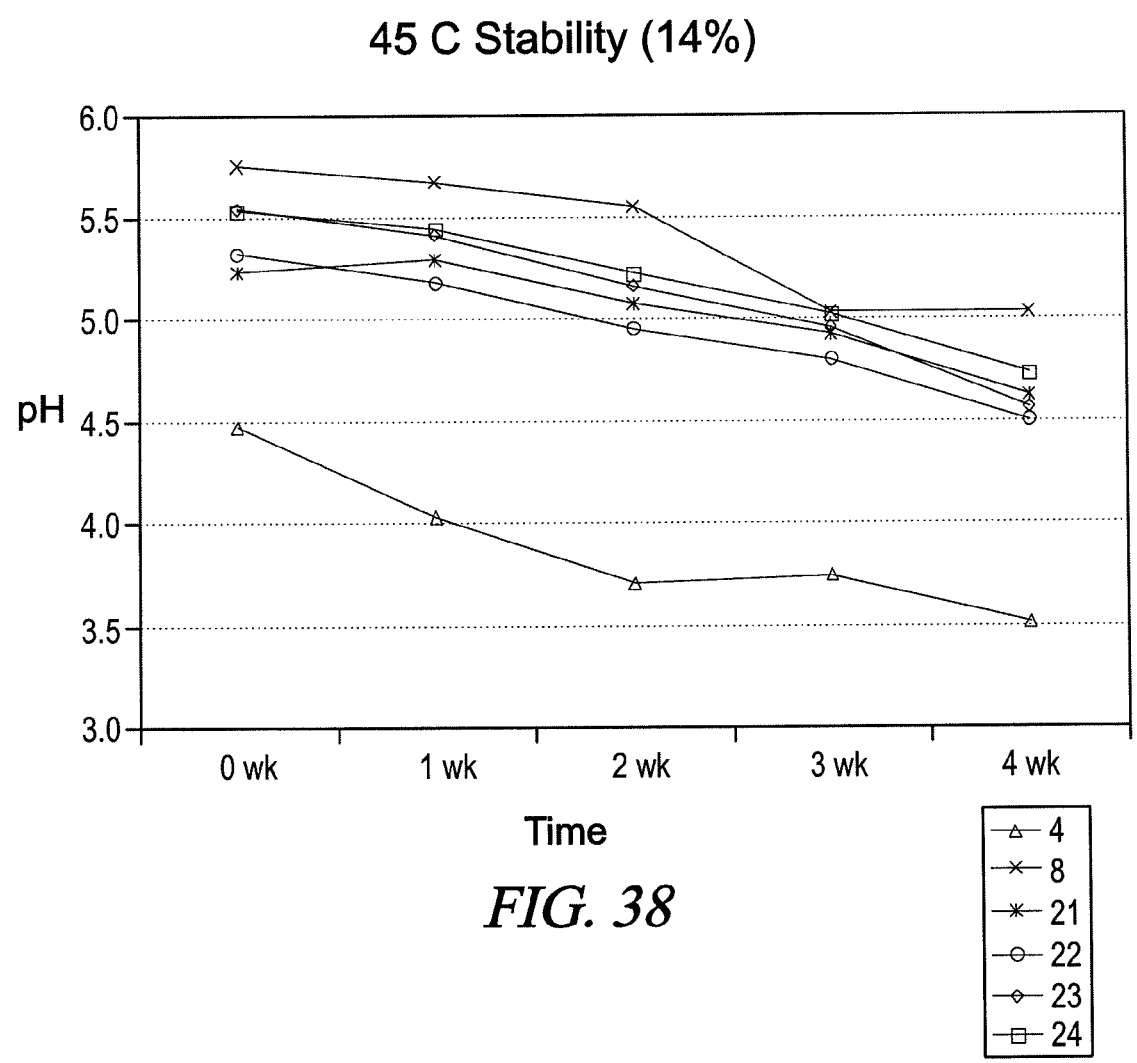
Figure 39:
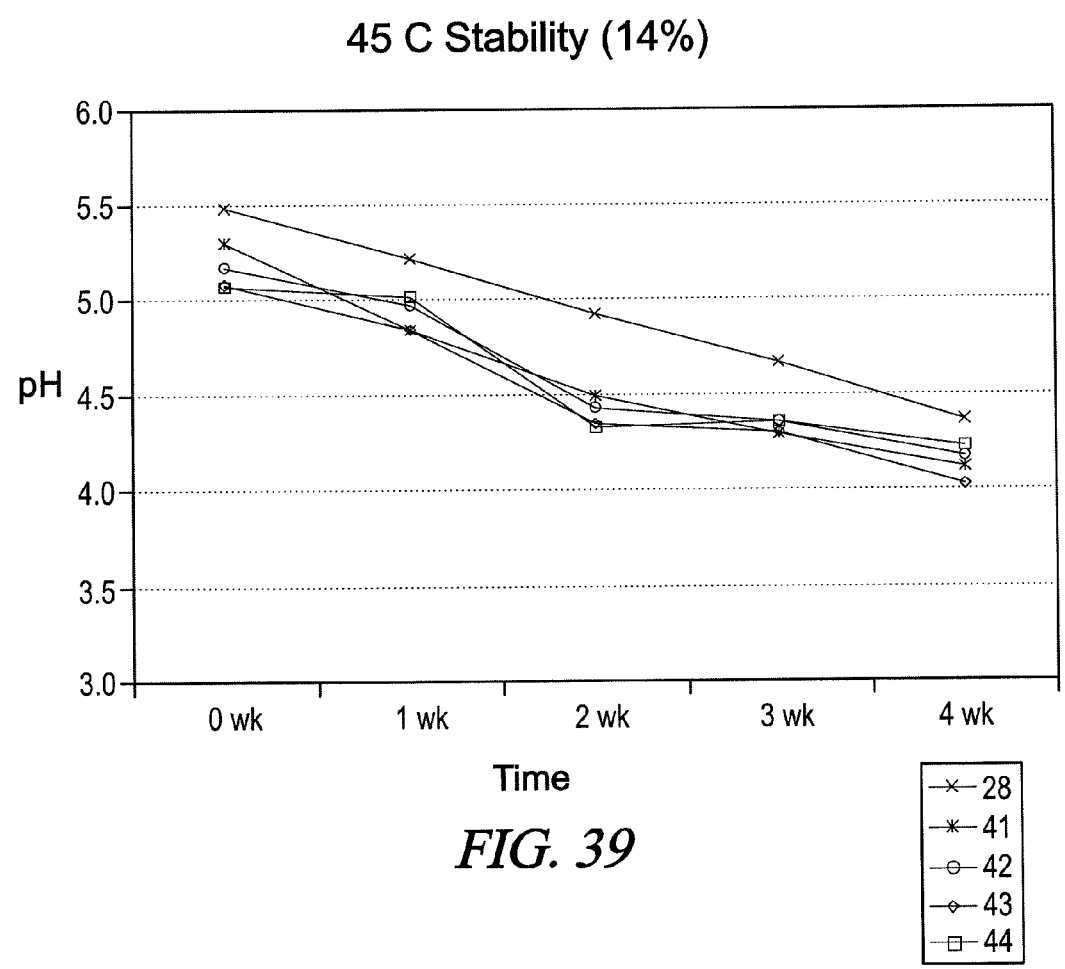
Figure 40:
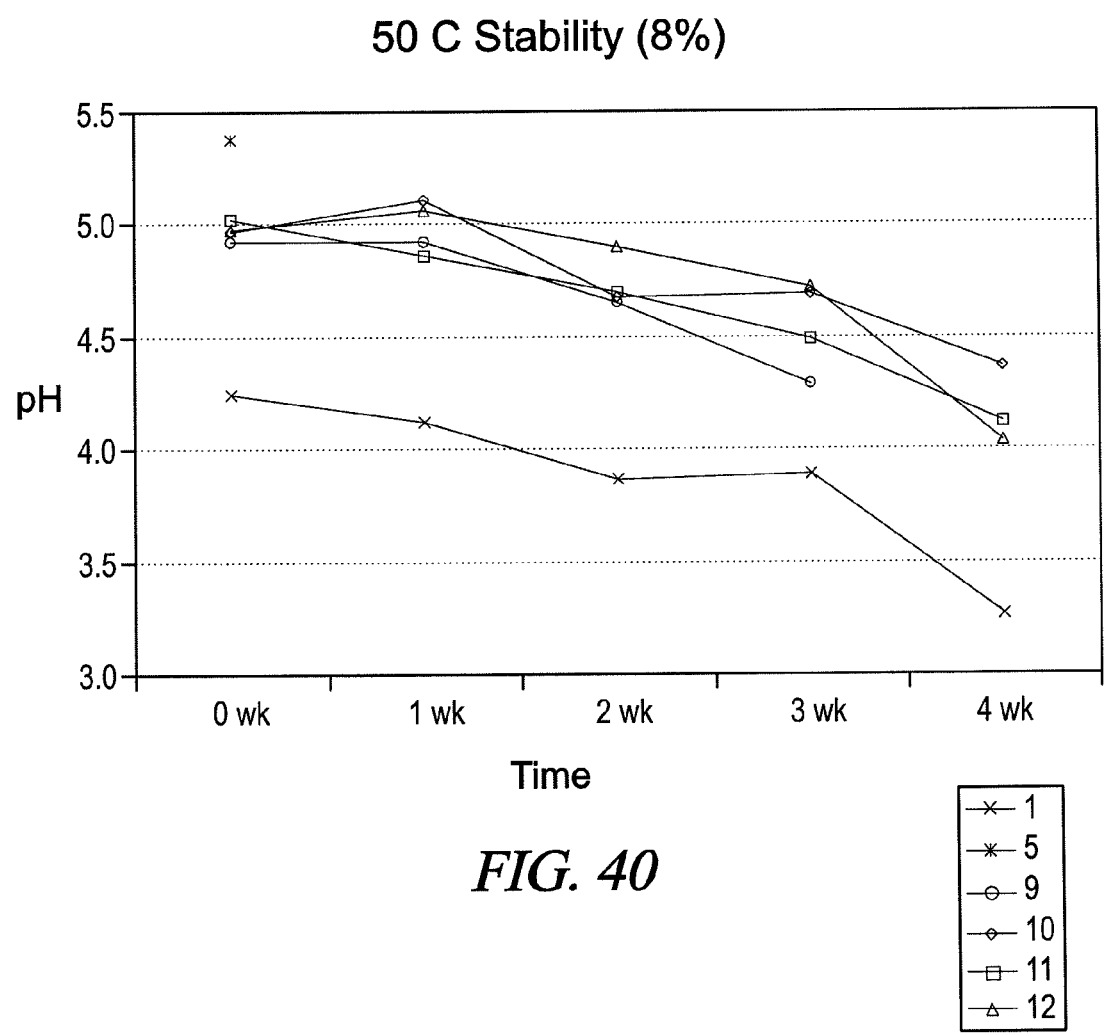
FIGS. 40-47 are graphical representations of the pH changes over time of the formulations of FIG. 14 as evaluated at 50° C.
Figure 41:
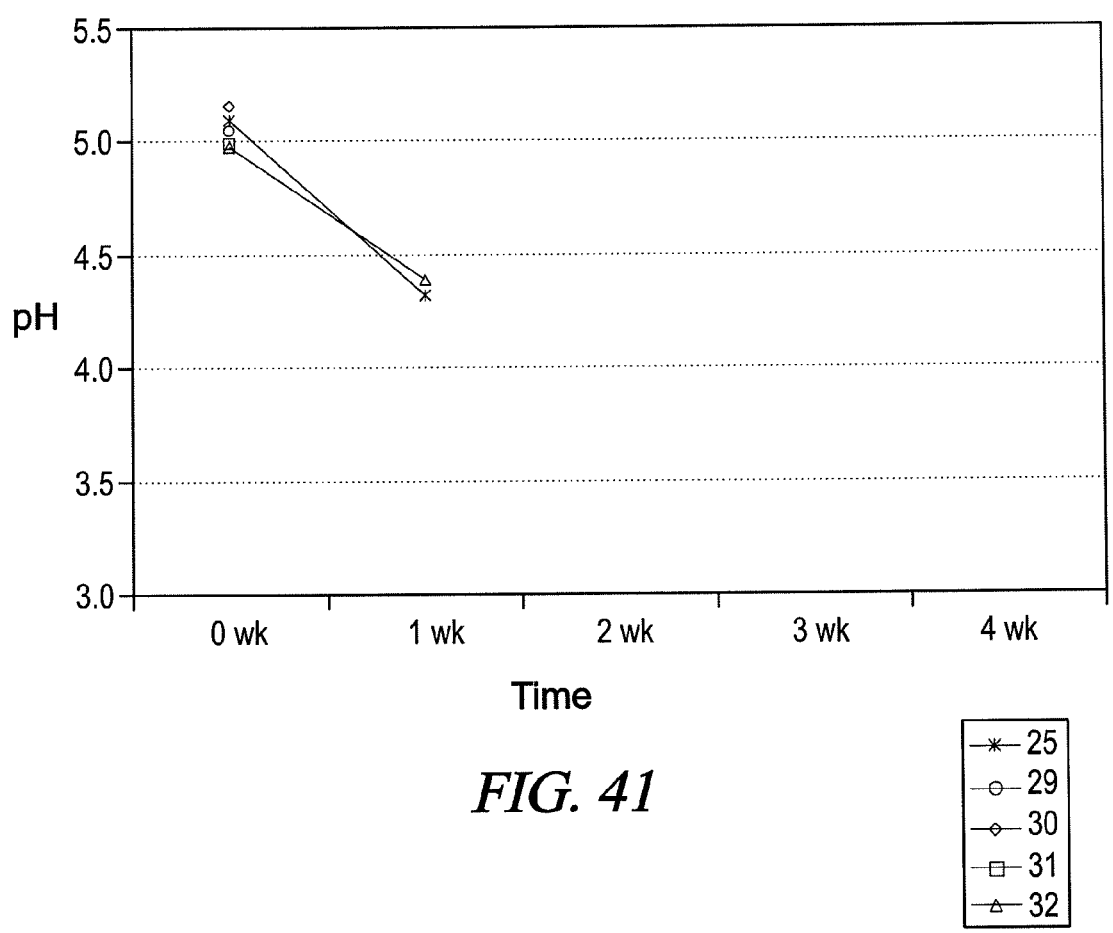
Figure 42:
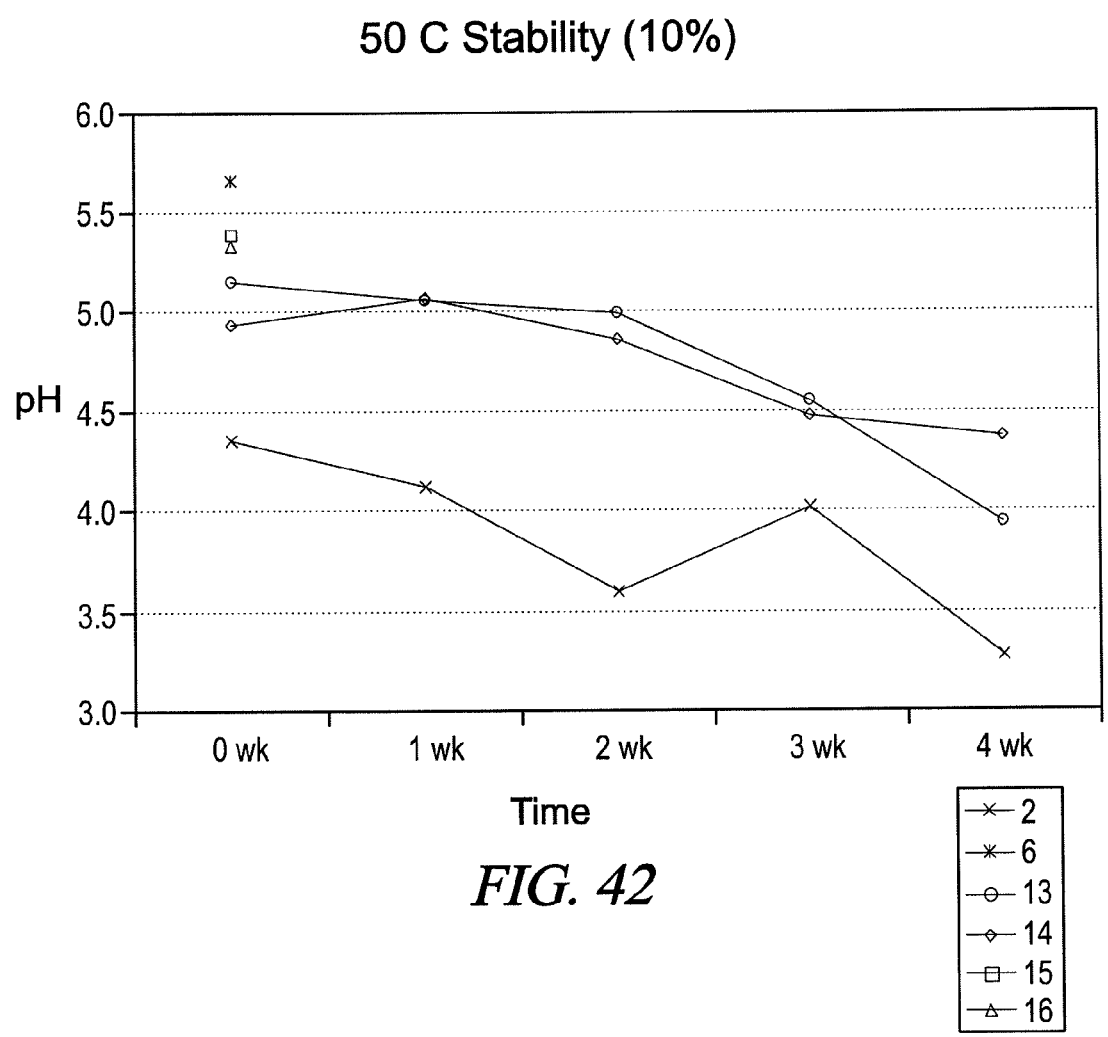
Figure 43:
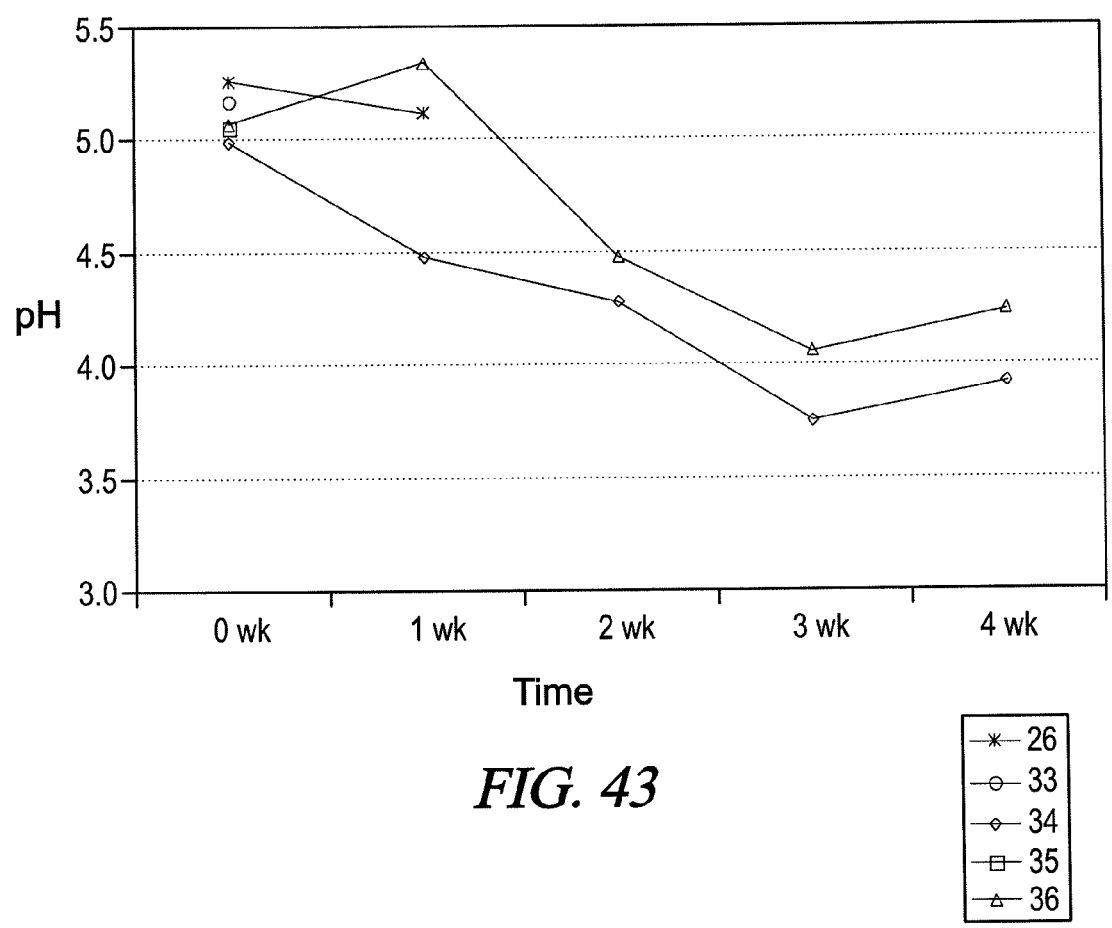
Figure 44:
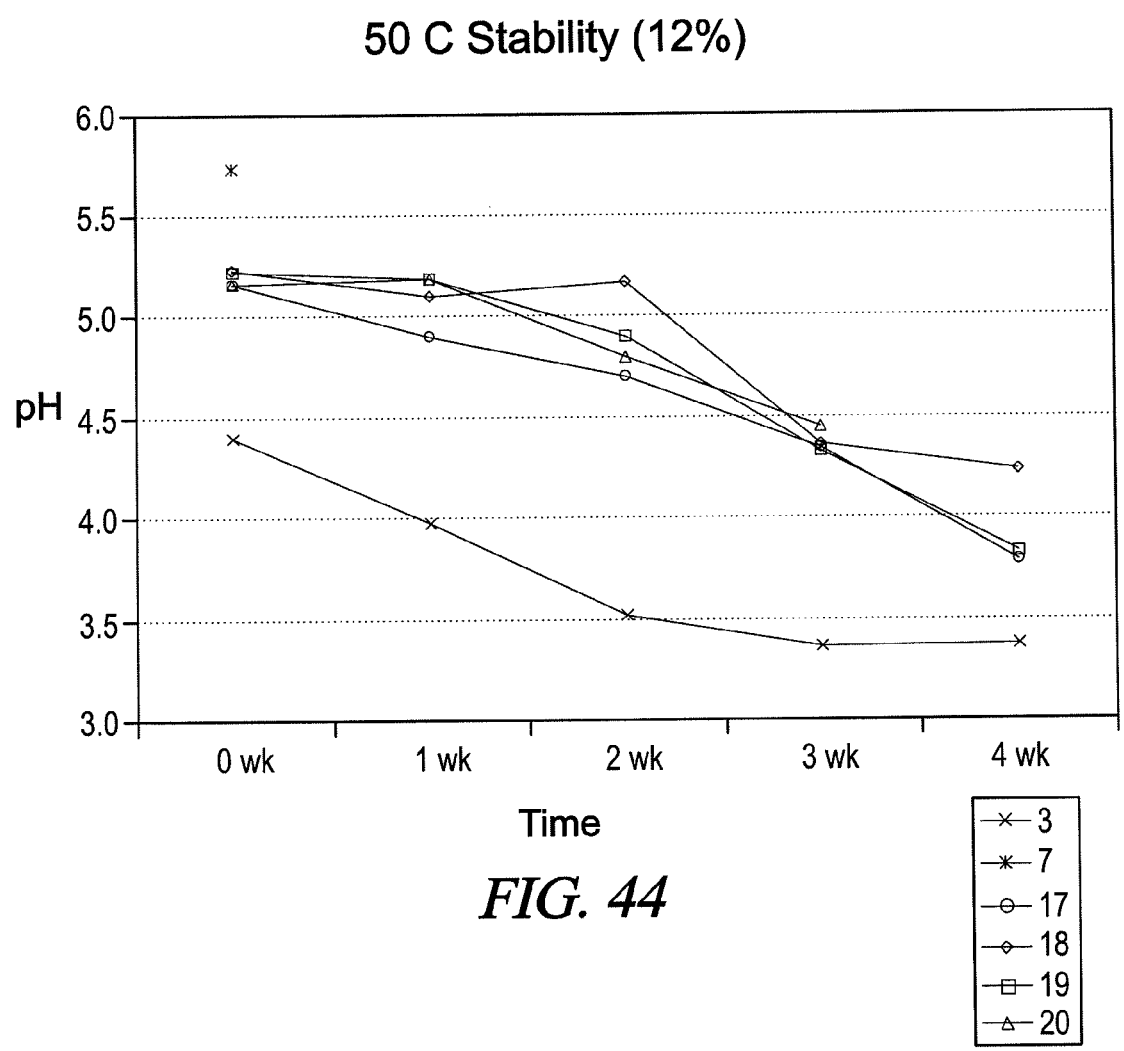
Figure 45:
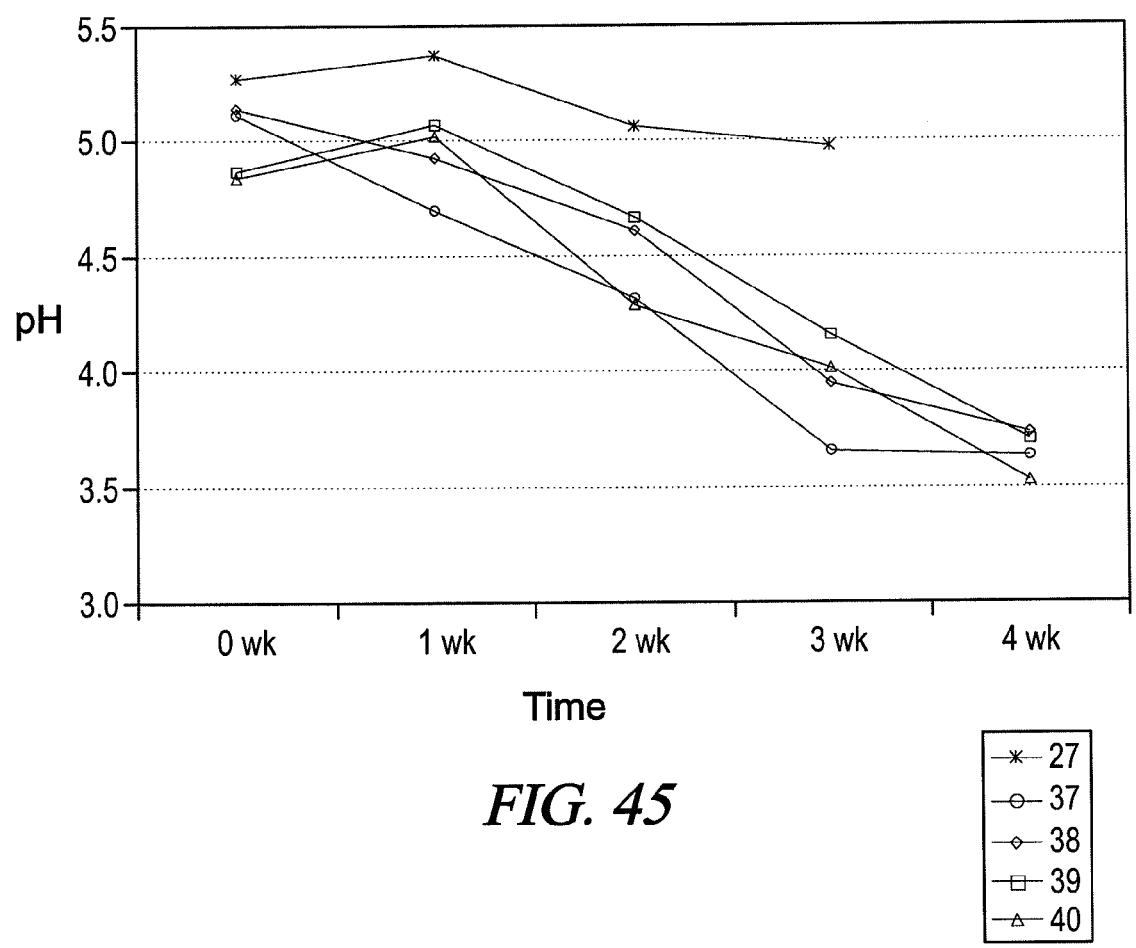
Figure 46:
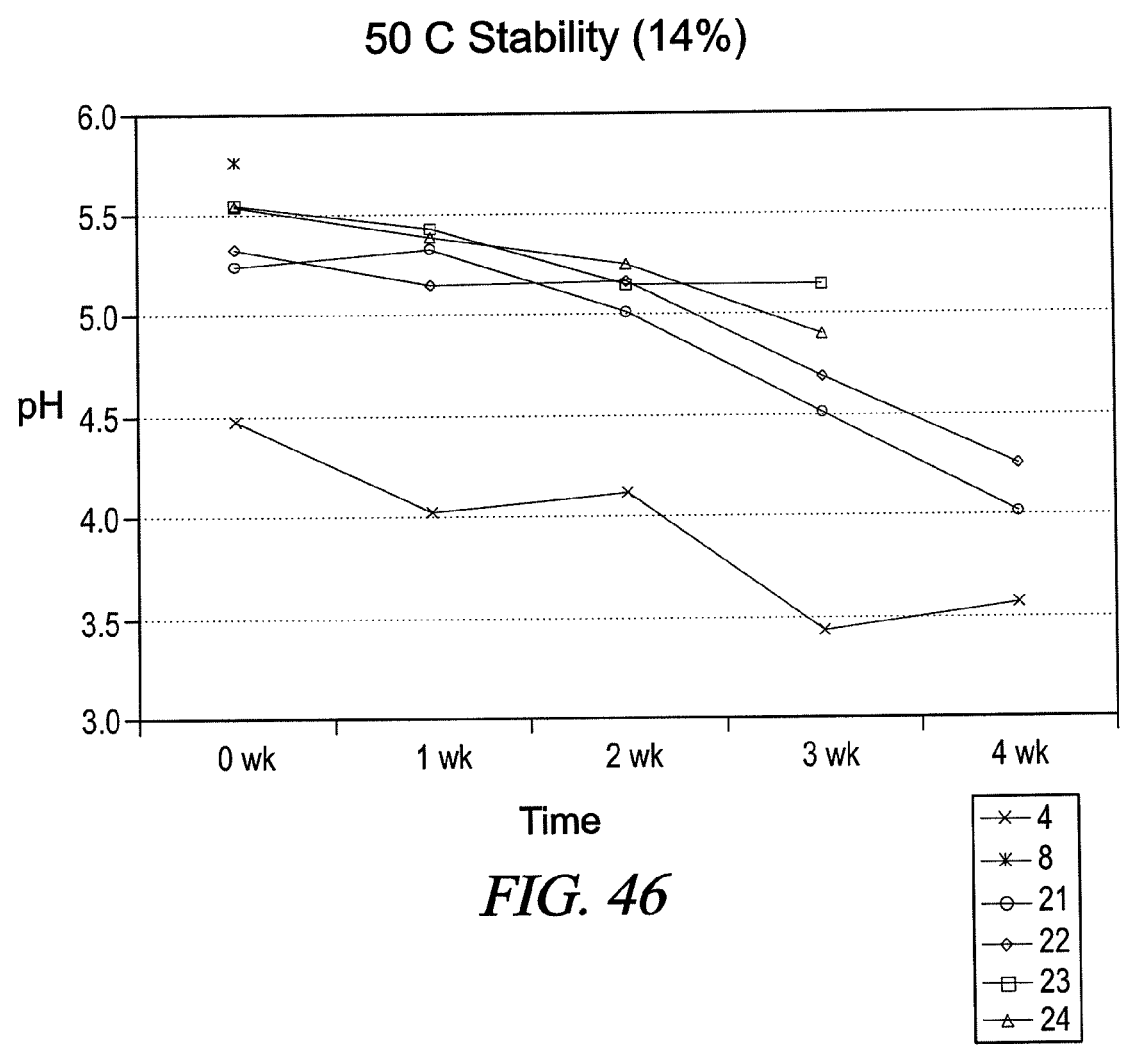
Figure 47:
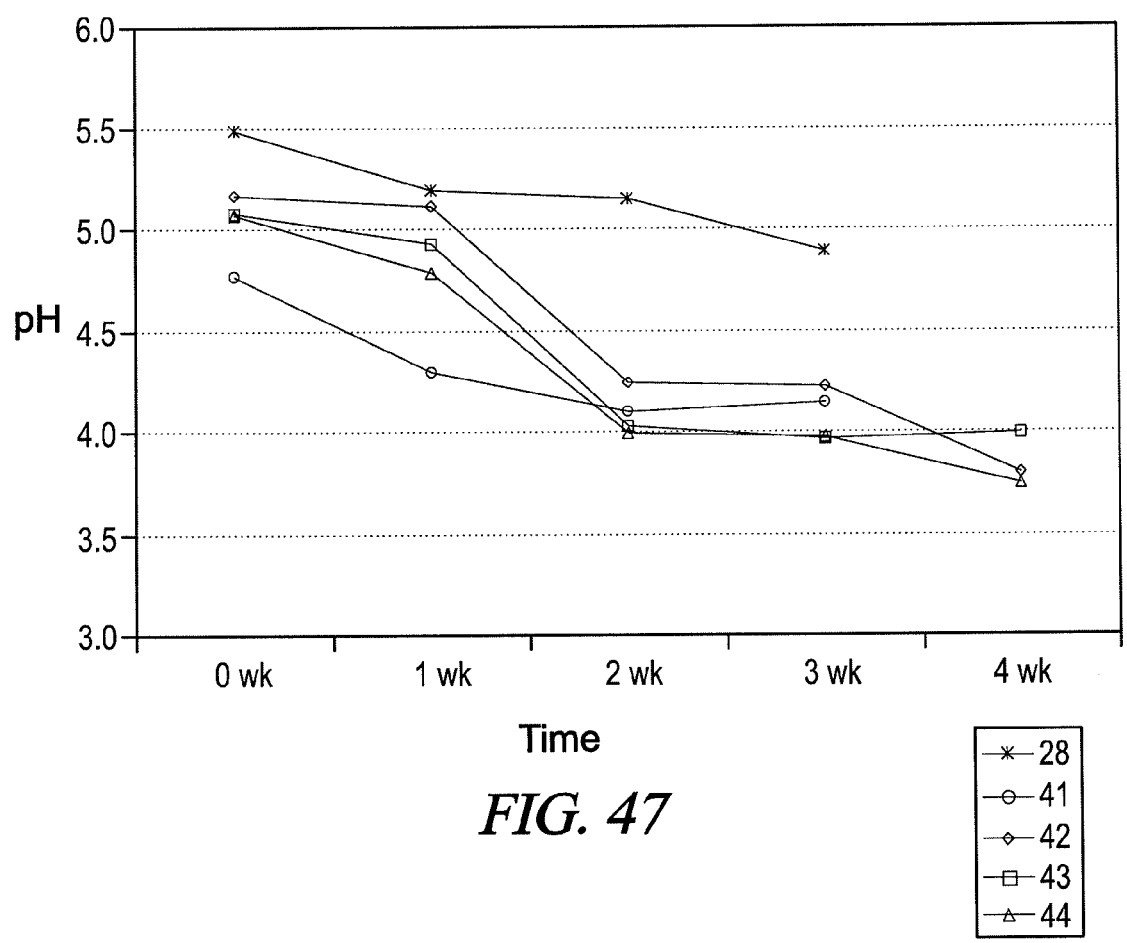

Hair tresses were bleached and treated with CC9, CC1, and CC2, as described in Example 10. The method of Lunn and Evans (JSCC, (1977), 28, 549-569) (the contents of which are incorporated herein by reference) were used to quantify the anti-static benefit. Hair tresses were equilibrated at low humidity and then brushed. An appropriately placed sensor provided real-time measurement of the static build-up. Eight tresses were evaluated per sample. Untreated tresses were also evaluated. The results are shown below and are plotted graphically in FIG. 13.

| Treatment | N | Mean | Std Dev | Std Err Mean | |
|---|---|---|---|---|---|
| Unconditioned Hair | 10 | 1452.0 | 216.6 | 68.48 | A |
| CC1 | 10 | 483.0 | 93.2 | 29.48 | B |
| CC2 | 10 | 148.6 | 47.0 | 14.87 | C |
| CC9 | 10 | 116.4 | 26.5 | 8.38 | C |

Levels not connected by same letter are significantly different

As can been seen from the results, CC9 provides comparable protection against static flyaway as the positive control.

Example 13

Forty-four formulations of the invention were prepared to evaluate longer term shelf stability of the formula. The formulations 1-44 were prepared by mixing together the ingredients as set out in FIG. 14.

In each of formulations 9-24, the ingredient called out as "Base I" is: behenyl alcohol 57.61%, stearyl alcohol 57.61%, isoleucine 14.25%, and ethane sulfonic acid 17.94%. In each of formulations 1-8 and 25-28, the ingredient called out as "Base II" is: Base 133.26%, cetyl alcohol 33.26%, stearyl alcohol 33.26%, and sodium carbonate 0.22%.

The initial physical properties of pH and viscosity for each formulation were evaluated and are shown in FIG. 15. Each formulation was split into several samples, which were maintained at room temperature, 5° C., 45° C. or 50° C. and pH (an indicator of stability) was re-evaluated at time points of various duration. The results are shown graphically in FIGS. 16-47.

While it has been shown and described several embodiments in accordance with the invention and use thereof, it is understood that the same is not limited thereto, but is susceptible to many changes and modifications to one possessing ordinary skill in the art, and therefore we do not wish to be limited to the details shown and described herein, but intend to cover all such modifications as are encompassed by the scope of the appended claims.

I claim:

1. A method of increasing the substantivity of a personal care composition to hair, skin or nails comprising:
   preparing a composition that comprises an aqueous phase, a non-aqueous phase and a neutralized amino acid ester chosen from LIEE, BLIE or a combination thereof; wherein the composition is substantially free of petrochemicals and/or derivates of petrochemical materials, and the aqueous phase and the non-aqueous phase are emulsified by the neutralized amino acid ester; and
   applying the personal care composition to a surface of hair, skin or nails, wherein the composition exhibits increased substantivity on the surface relative to the substantivity of a composition that does not contain the amino acid ester and which is substantially free of petrochemicals and/or derivatives of petrochemical materials.

2. The method of claim 1, wherein an amine group of the amino acid is neutralized by an ethanesulfonic acid that is derived from an ethanol that is derived from fermentation of vegetable matter.

3. The method of claim 1, wherein the amino group of the amino acid is neutralized by an acid chosen from hydrochloric acid, phosphoric acid, sulfuric acid, boric acid, and nitric acid.

4. The method of claim 1, wherein the personal care composition further comprises at least one of a surfactant, a colorant, a pearlizing agent, an acrylate polymer, an antioxidant, an opacifying agent, mica, an oil, a lipid, a protein a pH modifier, a vitamin, a fatty acid, a fatty alcohol, a humectant, and a conditioning agent.

5. The method of claim 1, wherein the composition is chosen from a hair detergent, shampoo, rinse, hair cream conditioner, conditioning shampoo, hair lotions, hair treatment, hair cream, hair spray, hair liquid, hair wax, hair-styling preparation, permanent wave liquids, hair colorant, acidic hair colorant, hair manicure, glaze, skin lotion, milky lotion, face wash, makeup remover, cleansing lotion, emollient lotion, nourishing cream, emollient cream, massage cream, cleansing cream, body shampoo, hand soap, bar soap, shaving creams, sunscreen, sunburn treatment, deodorants, makeup removing gel, moisture gel, moisture essence, UV exposure-preventing essence, shaving foam, face powder, foundation, lipstick, blush, eyeliner, wrinkle and anti-aging cream, eye shadow, eyebrow pencils, mascara, mouthwash, toothpaste, an oral care composition, a skin cleansing composition, a textile cleansing compositions, a dish cleaning composition, a hair or fur cleansing composition, a deodorant or antiperspirant, a cosmetic, a hair styling composition, a skin moisturizer, a skin conditioner, a hair conditioner and a nail conditioner.

6. A method of emulsifying a personal care composition having an aqueous phase and an non-aqueous phase comprising preparing a composition that comprises an aqueous phase, a non-aqueous phase and a neutralized amino acid ester that is chosen from LIEE, BLIE or a combination thereof; and wherein the composition is substantially free of petrochemicals and/or derivatives of petrochemical materials.

7. The method of claim 6, wherein the amine group of the amino acid is neutralized by an ethanesulfonic acid that is derived from an ethanol that is derived from fermentation of vegetable matter.

8. The method of claim 6, wherein an amine group of the amino acid is neutralized by an acid chosen from hydrochloric acid, phosphoric acid, sulfuric acid, boric acid, and nitric acid.

9. The method of claim 6, wherein the personal care composition further comprises at least one of a surfactant, a colorant, a pearlizing agent, an acrylate polymer, an antioxidant, an opacifying agent, mica, an oil, a lipid, a protein, a pH modifier, a vitamin, a fatty acid, a fatty alcohol, a humectant, and a conditioning agent.

10. The method of claim 6, wherein the composition is chosen from a hair detergent, shampoo, rinse, hair cream condition, conditioning shampoo, hair lotions, hair treatment, hair cream, hair spray, hair liquid, hair wax, hair-styling preparation, permanent wave liquids, hair colorant, acidic hair colorant, hair manicure, glaze, skin lotion, milky lotion, face wash, makeup remover, cleansing lotion, emollient lotion, nourishing cream, emollient cream, massage cream, cleansing cream, body shampoo, hand soap, bar soap, shaving creams, sunscreen, sunburn treatment, deodorants, makeup removing gel, moisture gel, moisture essence, UV exposure-preventing essence, shaving foam, face powder, foundation, lipstick, blush, eyeliner, wrinkle and anti-aging cream, eye shadow, eyebrow pencils, mascara, mouthwash, toothpaste, an oral care composition, a skin cleansing composition, a textile cleansing compositions, a dish cleaning composition, a hair or fur cleansing composition, a deodorant or antiperspirant, a cosmetic a hair styling composition, a skin moisturizer, a skin conditioner, a hair conditioner and a nail conditioner.

11. A method of conditioning or lubricating the skin, hair or nails comprising applying a neutralized amino acid ester to a surface of skin, hair or nails, wherein the neutralized amino acid ester is chose from LIEE, BLIE or a combination thereof.

12. The method of claim 11, wherein the neutral amino acid is obtained from vegetable matter.

13. A cationic emulsifier for use in a personal care composition is substantially free of petrochemicals and/or derivatives of petrochemical materials comprising a neutralized amino acid ester chosen from LIEE, BLIE or a combination thereof, and wherein the neutralized amino acid ester also is capable of condition and/or lubricating a hair, skin or nail substrate.

* * * * *